US008530197B2

(12) United States Patent
Li et al.

(10) Patent No.: US 8,530,197 B2
(45) Date of Patent: Sep. 10, 2013

(54) METHOD OF MAKING A PAIRED TAG LIBRARY FOR NUCLEIC ACID SEQUENCING

(75) Inventors: Bin Li, Foster City, CA (US); Lei Xi, Foster City, CA (US); Swati S. Ranade, San Mateo, CA (US); Yangzhou Wang, Foster City, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 670 days.

(21) Appl. No.: 12/350,837

(22) Filed: Jan. 8, 2009

(65) Prior Publication Data
US 2009/0181861 A1    Jul. 16, 2009

Related U.S. Application Data

(60) Provisional application No. 61/109,638, filed on Oct. 30, 2008, provisional application No. 61/020,114, filed on Jan. 9, 2008.

(51) Int. Cl.
*C12P 19/34* (2006.01)
*C12Q 1/68* (2006.01)

(52) U.S. Cl.
USPC .......................... 435/91.2; 435/6.1

(58) Field of Classification Search
USPC ................................. 435/91.2, 6.1
See application file for complete search history.

(56) References Cited

U.S. PATENT DOCUMENTS

| | | | |
|---|---|---|---|
| 6,197,557 B1 | 3/2001 | Makarov et al. | |
| 6,720,179 B1 | 4/2004 | Macevicz | |
| 2006/0024681 A1 | 2/2006 | Smith et al. | |
| 2006/0292611 A1 | 12/2006 | Berka et al. | |
| 2009/0264299 A1* | 10/2009 | Drmanac et al. | 506/3 |

FOREIGN PATENT DOCUMENTS

| | | |
|---|---|---|
| CN | 1950519 | 4/2007 |
| WO | WO 2005/042781 A2 | 5/2005 |
| WO | WO 2005/082098 A2 | 9/2005 |
| WO | WO-2007/044245 | 4/2007 |
| WO | WO 2007/044245 A2 | 4/2007 |
| WO | WO 2007/091077 A1 | 8/2007 |
| WO | PCT/US2009/030490 | 1/2009 |

OTHER PUBLICATIONS

"Tech Summary: ABI's SOLiD (Seq. by Oligo Ligation/Detecion), Updated for v2.0" SEQanswers online forum, found at http://seqanswers.com/forums/showthreat.php?t=10, accessed on Oct. 8, 2008.
Acul. New England BioLabs online catalog. Printed Jun. 24, 2009. available no later than Oct. 29, 2008. found at http://www.neb.com/nebecomm/products/productR0641.asp.
Bcgl. New England BioLabs online catalog. Printed Jun. 24, 2009. available no later than Oct. 29, 2008. found at http://www.neb.com/nebecomm/products/productR0545.asp.
Briggs et al. "Patterns of damage in genomic DNA sequences from a Neandertal" Proc. Nat. Acad. Sci. USA, Sep. 2007, 104(37): 14616-14621.
Hall, Neil. "Advanced Sequencing Technologies and Their Wider Impact in Microbiology" Journal of Experimental Biology 210: 1518-1525 (2007).
Heiter, DF. et al, 2005, J. Mol. Biol., 348, 631-640.
Kent, W.J. et al., Genome Res. 2001, 11: 1541-8.
Korbel et al. "Paired-end mapping reveals extensive structural variation in the human genome" Science, Oct. 2007, 318(5849): 420-426.
Mullikin S. C. et al., Genome Res. 2003, 13: 81-90.
NG et al. "Multiplex sequencing of paired-end ditags (MS-PET) : a strategy for the ultra-high-throughput analysis of trascriptomes and genomes" Nucleic Acids Research, Jul. 2006, 34 (12): e84.
Porecca et al. "Unit 7.8 Polony DNA Sequencing" Current Protocols in Molecular Biology, Nov. 2006, vol. Supplement. 76, pp. 7.8.1-7.8.22.
Restriction Endonucleases Overview. New England Biolabs, printed Jun. 24, 2009. available no later than Oct. 29, 2008, accessed at http://www.neb.com/nebecomm/tech_reference/restriction_enzymes/overview.asp.
Roach J. C. et al., Genomics. 1995, 26: 345-353.
Rigby, P. W. et al. (1977), J. Mol. Biol. 113, 237.
Samuelson, J.C., et al Nar, 32: 3661-3671.
Shendure et al. Accurate Multiplex Polony Sequencing of an Evolved Bacterial Genome. Science Sep. 2005, 309 (5741): 1728-1732.
Shuman, Stewart. "Recombination mediated by vaccinia virus DNA topoisomerase I in *Escherichia coli* is sequence specific", Proc. Natl. Acad. Sci. USA, 88: 10104-10108, Nov. 1991.
Siegel A. F. et al., Genomics. 2000, 68: 237-246.
Zhu, Z. et al. 2004, J. Mol. Biol. 337: 573-583.
International Search Report and Written Opinion dated May 6, 2009, received in International Application No. PCT/US2009/030490.
International Preliminary Report on Patentability mailed Jul. 22, 2010, for International Application No. PCT/US2009/030490, with Notification and Written Opinion.
CN1950519 A, Abstract Translation, Apr. 18, 2007, 1.
CN200980108336.7, First Search Report mailed Oct. 9, 2012 (Translation).

* cited by examiner

*Primary Examiner* — Cynthia Wilder

(57) ABSTRACT

The present disclosure relates to methods and compositions for making paired tags and paired tag libraries.

72 Claims, 29 Drawing Sheets

METHOD OF MAKING A PAIRED TAG LIBRARY FOR NUCLEIC ACID SEQUENCING

RELATED APPLICATIONS

This application claims priority to U.S. Provisional Applications Ser. No. 61/109,638, filed Oct. 30, 2008, and 61/020,114, filed Jan. 9, 2008, hereby incorporated by reference in their entireties.

FIELD

The present disclosure relates to methods and compositions for making and using sequence paired tags and paired tag libraries.

INTRODUCTION

The technique of "paired-end," "pairwise," or "paired tag" sequencing is generally known in the art of molecular biology, particularly in the context of whole-genomic shotgun sequencing (Siegel A. F. et al., Genomics. 2000, 68: 237-246; Roach J. C. et al., Genomics. 1995, 26: 345-353). Paired tag sequencing allows the determination of two "reads" of sequence from two places on a single polynucleotide duplex. In some situations, the paired-end approach allows for more information to be gained from sequencing two stretches of nucleic acid sequences, each "n" bases in length than from sequencing "n" bases from each of two independent nucleic acid sequences in a random fashion. For example, with the use of appropriate software tools for the assembly of sequence information (Millikin S. C. et al., Genome Res. 2003, 13: 81-90; Kent, W. J. et al., Genome Res. 2001, 11: 1541-8) it is possible to make use of the knowledge that the "paired tag" sequences are not completely random, but are known to occur on a single duplex, and are therefore linked or paired in the genome. This information can aid in the assembly of whole genome sequences into a consensus sequence.

SUMMARY

In some embodiments, the present teachings provide methods and products that facilitate making paired tags and paired tag libraries. In some embodiments, these can be used to increase size of the paired tags that are produced and to reduce costs. This extended size can facilitate sequence assembly and improve the accuracy for next-generation DNA sequencing applications such as microbial identification and genetic variation discovery.

In some embodiments, a method for forming a paired tag comprising a first tag sequence and a second tag sequence is provided. The method comprises ligating a first end and a second end of a double stranded polynucleotide of interest to an adaptor thereby forming a circular nucleic acid molecule, wherein the circular nucleic acid molecule comprises a first nick between the first end of the double stranded polynucleotide of interest and the adaptor, and a second nick between the second end of the double stranded polynucleotide of interest and the adaptor, wherein the first nick and the second nick are on different strands of the circular nucleic acid molecule than the second nick; and performing a nick translation reaction wherein at least one nick is translated into the polynucleotide of interest.

In some embodiments, a method of forming a released paired tag from a DNA fragment of interest is provided. The method comprises ligating a first adaptor to a first end of a DNA fragment of interest and ligating a second adaptor to a second end of the DNA fragment of interest, thereby producing an adaptor modified fragment, circularizing the adaptor modified fragment by attaching a third adaptor to the adaptor modified fragment, thereby forming a circular nucleic acid molecule wherein a first nick is present between the third adaptor and the first adaptor and a second nick is present between the second adaptor and the third adaptor, wherein the circular nucleic acid molecule comprises a first strand and a second strand of DNA, and wherein the first nick and the second nick are not present on the same strand of the circular nucleic acid molecule; performing a nick translation reaction wherein a nick on each strand of the circular nucleic acid molecule is translated into the DNA fragment of interest, and cleaving the circular nucleic acid molecule at a position at a translated nick, thereby forming a released paired tag.

In some embodiments a released paired tag library is provided. The released paired tag library comprises two or more released paired tags prepared by a method comprising ligating a first adaptor to a first end of a polynucleotide of interest and ligating a second adaptor to a second end of the polynucleotide of interest, thereby producing an adaptor modified polynucleotide of interest, circularizing the adaptor modified polynucleotide of interest by attaching a third adaptor to the adaptor modified polynucleotide of interest, thereby forming a circular nucleic acid molecule wherein a first nick is present between the third adaptor and the first adaptor and a second nick is present between the second adaptor and the third adaptor, wherein the circular nucleic acid molecule comprises a first strand and a second strand, and wherein the first nick and the second nick are not present on the same strand of the circular nucleic acid molecule; performing a nick translation reaction wherein a nick on a strand of the circular nucleic acid molecule is translated into the polynucleotide of interest, and cleaving the circular nucleic acid molecule at a position at a translated nick, thereby forming a released paired tag.

In some embodiments a released paired tag is provided. The released paired tag comprises a first tag sequence, wherein the first tag sequence comprises a first end of a polynucleotide of interest, wherein the first tag sequence is greater than 27 nucleotides in length; a first adaptor covalently bonded to the first tag sequence, wherein the first adaptor comprises a binding moiety; and a second tag sequence covalently bonded to the first adaptor, wherein the second tag sequence comprises a second end of the polynucleotide of interest, and wherein the second tag sequence is greater than 27 nucleotides in length.

In some embodiments a solution is provided. The solution comprises a circular nucleic acid molecule, the circular nucleic acid molecule comprises: a double stranded polynucleotide of interest comprising a first end and a second end; and at least one adaptor. The at least one adaptor can be covalently bonded to the first end and the second end of the double stranded polynucleotide of interest, thereby forming a circularized nucleic acid molecule. The circular nucleic acid molecule further comprises a first nick between the first end of the double stranded polynucleotide of interest and the adaptor, and a second nick between the second end of the double stranded polynucleotide of interest and the adaptor. The first nick is on a different strand of the circular nucleic acid molecule than the second nick or gap. The solution can also include a nick translation enzyme. In some embodiments, the solution further comprises a second circular nucleic acid molecule, the second circular nucleic acid molecule comprises a double stranded polynucleotide of interest comprising a first end and a second end and the at least one adaptor covalently bonded to the first end and the second end of the double stranded polynucleotide of interest, thereby forming a second circularized nucleic acid molecule. The second circular nucleic acid molecule comprises a third nick, wherein the third nick is more than 27 nucleotides away from the location between the first end of the double stranded polynucleotide of interest and the adaptor, and a fourth nick, wherein the fourth nick is more than 27 nucleotides away from the location between the second end of the double stranded polynucleotide of interest and the adaptor, and wherein the third nick is on a different strand of the circular nucleic acid molecule than the fourth nick.

In some embodiments, a method of forming a paired tag is provided. The paired tag comprises a first tag sequence and a second tag sequence that together comprise at least part of a polynucleotide of interest. The method comprises ligating a first end of a double stranded polynucleotide of interest to at least one adaptor and ligating a second end of the double stranded polynucleotide of interest to at least one adaptor. The method further comprises forming a circular nucleic acid molecule comprising the double stranded polynucleotide of interest, a first nick comprising a first 3' end on a first strand of the circular nucleic acid molecule and a second nick comprising a second 3' end on a second strand of the circular nucleic acid molecule. The first nick and the second nick are on different strands of the circular nucleic acid molecule. The method further comprises extending the first 3' end of the first strand of the circular nucleic acid molecule into a sequence of the double stranded polynucleotide of interest and extending the second 3' end of the second strand of the circular nucleic acid molecule into a sequence of the double stranded polynucleotide of interest.

In some embodiments, a nicked linking polynucleotide is provided. The nicked linking polynucleotide comprises a first adaptor comprising a first adaptor strand that is hybridized to a second adaptor strand. The first adaptor strand lacks a phosphate group on its 5' end. The nicked linking polynucleotide further comprises a second adaptor comprising a third adaptor strand that is hybridized to a fourth adaptor strand. The third adaptor strand lacks a phosphate group on its 5' end. The nicked polynucleotide further comprises a linking polynucleotide comprising a first linking strand hybridized to a second linking strand. The linking polynucleotide comprises a first end and a second end. The first adaptor is attached to the first end of the linking polynucleotide such that a nick is present where the first adaptor strand lacks a phosphate group on its 5' end. The second linking strand is attached to the second adaptor strand. The second adaptor is attached to the second end of the linking polynucleotide such that a nick is present where the third adaptor strand of the second adaptor lacks a phosphate group on its 5' end. The second strand of the linking polynucleotide is attached to the fourth adaptor strand.

In some embodiments, a nicked linking polynucleotide is provided. The nicked linking polynucleotide comprises a first double stranded adaptor, a double stranded linking polynucleotide, and a second double stranded adaptor attached to a second end of the double stranded linking polynucleotide. The first double stranded adaptor is attached to a first end of a double stranded linking polynucleotide. There is a first nick separating a first strand of the first adaptor and a first strand of the double stranded vector and a second nick separating a second strand of the second adaptor and a first strand of the double stranded vector. The first nick and second nick are on different strands of the nicked vector.

In some embodiments, a method of preparing a paired tag is provided. The method comprises providing a nicked linking polynucleotide comprising a first adaptor comprising a first adaptor strand that is hybridized to a second adaptor strand, wherein the first adaptor strand lacks a phosphate group on its 5' end; a second adaptor comprising a third adaptor strand that is hybridized to a fourth adaptor strand, wherein the third adaptor strand lacks a phosphate group on its 5' end; and a linking polynucleotide comprising a first linking strand hybridized to a second linking strand. The linking polynucleotide comprises a first end and a second end. The first adaptor is attached to the first end of the linking polynucleotide such that a nick is present where the first adaptor strand lacks a phosphate group on its 5' end. The second linking strand is attached to the second adaptor strand. The second adaptor is attached to the second end of the linking polynucleotide such that a nick is present where the third adaptor strand of the second adaptor lacks a phosphate group on its 5' end. The second strand of the linking polynucleotide is attached to the fourth adaptor strand. The method further comprises ligating a first end of a double stranded polynucleotide of interest to the first adaptor, ligating a second end of the double stranded polynucleotide of interest to the second adaptor, and moving the first and second nicks into the double stranded polynucleotide of interest.

In some embodiments, methods of preparing paired tags, and the paired tags themselves are provided. In some embodiments, the methods allow for the production of paired tags that are not size constrained. In some embodiments, the invention comprises a linear paired tag. The linear paired tag can comprise a first tag sequence. The first tag sequence comprises a first end of a polynucleotide of interest. The linear paired tag can further comprise a first adaptor covalently bonded to the first tag sequence and a second tag sequence covalently bonded to the first adaptor. The second tag sequence comprises a second end of the polynucleotide of interest. The linear paired tag lacks a type IIs restriction site and lacks a type III restriction site.

In some embodiments, a method of forming a paired tag comprising a first tag sequence and a second tag sequence that together comprise at least part of a polynucleotide of interest is provided. The method can comprise ligating a first end and a second end of a double stranded polynucleotide of interest to an adaptor thereby forming a circular nucleic acid molecule, wherein the circular nucleic acid molecule comprises a first nick between the first end of the double stranded polynucleotide of interest and the adaptor, and a second nick between the second end of the double stranded polynucleotide of interest and the adaptor, wherein the first nick and the second nick are on different strands of the circular nucleic acid molecule than the second nick, and performing a nick translation reaction wherein at least one nick is translated into the polynucleotide of interest. In some embodiments, the method can further comprise allowing the nick translation reaction to proceed for a specific time; and terminating the nick translation reaction. In some embodiments, the first end and the second end of the double stranded polynucleotide of interest lack 5' phosphate residues. In some embodiments, the method further comprises terminating the nick translation reaction before the first nick and the second nick are translated past each other. In some embodiments, the first nick and the second nick are translated more than 10 bases. In some embodiments, the method further comprises the step of cleaving the circular nucleic acid molecule at the first nick and at the second nick. In some embodiments, the first nick and the second nick are translated less than 500 bases. In some embodiments, the first nick and the second nick are translated less than 200 bases. In some embodiments, the first nick and the second nick are translated less than 100 bases. In some embodiments, the first nick and the second nick are translated between about 20 bases to about 50 bases. In some embodiments, at least one nick is translated less than 500 bases. In some embodiments, at least one nick is translated more than 27 bases and less than 500 bases. In some embodiments, at least one nick is translated less than 200 bases. In some embodiments, at least one nick is translated from 28 bases to about 50 bases. In some embodiments, the circular nucleic acid molecule comprises a first gap between the first end of the double stranded polynucleotide of interest and the adaptor. In some embodiments, the circular nucleic acid molecule comprises a second gap between the second end of the double stranded polynucleotide of interest and the adaptor. In some embodiments, the circular nucleic acid sequence comprises a gap that is filled in with nucleotides when the nick translation reaction is performed, thereby resulting in a nick. In some embodiments, the polynucleotide of interest comprises from 50 to 2500 nucleotides. In some embodiments, the polynucleotide of interest is subjected to a size selection technique to select for polynucleotides comprising from 50 to 2500 nucleotides prior to the ligating step. In some embodiments, the adaptor comprises a binding moiety. In some embodiments, the nick translation reaction is performed using an enzyme selected from the group consisting of *E. Coli* DNA polymerase I, Taq DNA polymerase, Vent DNA polymerase, Klenow DNA polymerase I, and phi29 DNA polymerase and any combination thereof. In some embodiments, the nick translation reaction is performed using a DNA polymerase having 5' to 3' exonuclease activity. In some embodiments, the nick translation reaction comprises removal of nucleotides by 5' to 3' exonuclease activity. In some embodiments, the nick translation reaction occurs by strand displacement. In some embodiments, the method further comprises cleaving the circular nucleic acid molecule at a first translated nick, thereby forming a linear polynucleotide comprising a first tag sequence and a second tag sequence separated by the adaptor, wherein the first tag sequence and the second tag sequence are derived from the polynucleotide of interest. In some embodiments, the method further comprises cleaving the circular nucleic acid molecule at a second translated nick. In some embodiments, the circular nucleic acid molecule is cleaved by an enzyme selected from the group consisting of S1 nuclease, mung bean nuclease, nuclease P1, nuclease BAL-31, and any combination thereof. In some embodiments, the method further comprises amplifying the linear polynucleotide. In some embodiments, the adaptor comprises a binding moiety that comprises biotin. In some embodiments, the method further comprises the step of using streptavidin to purify the paired tag. In some embodiments, the method further comprises treating the polynucleotide of interest with an alkaline phosphatase prior to ligation, wherein a 5'-phosphate is removed from both the first end and the second end of the polynucleotide of interest. In some embodiments, the alkaline phosphatase is selected from the group consisting of calf intestinal alkaline phosphatase, bacterial alkaline phosphatase, shrimp alkaline phosphatase, and some combination thereof. In some embodiments, the circular nucleic acid molecule further comprises a second adaptor, wherein the second adaptor is positioned adjacent to the first adaptor. In some embodiments, one strand of the first adaptor and one strand of the second adaptor lack a 5' phosphate. In some embodiments, each step is performed in the order listed.

In some embodiments, a method of forming a released paired tag from a DNA fragment of interest is provided. The method can comprise ligating a first adaptor to a first end of a DNA fragment of interest and ligating a second adaptor to a second end of the DNA fragment of interest, thereby producing an adaptor modified fragment, circularizing the adaptor modified fragment by attaching a third adaptor to the adaptor modified fragment, thereby forming a circular nucleic acid molecule wherein a first nick is present between the third adaptor and the first adaptor and a second nick is present between the second adaptor and the third adaptor, wherein the circular nucleic acid molecule comprises a first strand and a second strand of DNA, and wherein the first nick and the second nick are not present on the same strand of the circular nucleic acid molecule; performing a nick translation reaction wherein a nick on each strand of the circular nucleic acid molecule is translated into the DNA fragment of interest, and cleaving the circular nucleic acid molecule at a position at a translated nick, thereby forming a released paired tag. In some embodiments, the method further comprises allowing the nick translation reaction to proceed for a specific time, and terminating the nick translation reaction. In some embodiments, the method further comprises terminating the nick translation reaction prior to cleaving the polynucleotide strand at each position at a translated nick. In some embodiments, the method further comprises attaching primer adaptors to the ends of the paired tag. In some embodiments, the method further comprises amplifying the paired tag with primers for the primer adaptors. In some embodiments, the amplification is a clonal amplification. In some embodiments, the clonal amplification comprises emulsion polymerase chain reaction (emulsion PCR). In some embodiments, the clonal amplification comprises bridge polymerase chain reaction (bridge PCR). In some embodiments, the third adaptor comprises a binding moiety, and further comprising binding the binding moiety to a solid support. In some embodiments, the solid support is an array. In some embodiments, the method further comprises sequencing a portion of the paired tag.

In some embodiments, a released paired tag library comprising two or more released paired tags that are prepared by a method is provided. The method can comprise ligating a first adaptor to a first end of a polynucleotide of interest and ligating a second adaptor to a second end of the polynucleotide of interest, thereby producing an adaptor modified polynucleotide of interest, circularizing the adaptor modified polynucleotide of interest by attaching a third adaptor to the adaptor modified polynucleotide of interest, thereby forming a circular nucleic acid molecule wherein a first nick is present between the third adaptor and the first adaptor and a second nick is present between the second adaptor and the third adaptor, wherein the circular nucleic acid molecule comprises a first strand and a second strand, and wherein the first nick and the second nick are not present on the same strand of the circular nucleic acid molecule; performing a nick translation reaction wherein a nick on a strand of the circular nucleic acid molecule is translated into the polynucleotide of interest, and cleaving the circular nucleic acid molecule at a position at a translated nick, thereby forming a released paired tag. In some embodiments, the polynucleotide of interest is prepared from an organism selected from the group consisting of a plasmid, a virus, a prokaryotic cell, an archaebacterial cell, a bacterial artificial chromosome, a eukaryotic cell, a cell line, a protozoan, a plant, an alga, a bacterium, a fungus, an insect, a reptile, a fish, an amphibian, a bird, and a mammal. In some embodiments, the polynucleotide of interest is subjected to a size selection technique. In some embodiments, the size selection technique is used to select for polynucleotides comprising from 2000 to 3000 nucleotides prior to the ligating step.

In some embodiments, a released paired tag is provided. The released paired tag comprises a first tag sequence, wherein the first tag sequence comprises a first end of a polynucleotide of interest, and wherein the first tag sequence is at least 27 nucleotides in length; a first adaptor covalently bonded to the first tag sequence; and a second tag sequence covalently bonded to the first adaptor, wherein the second tag sequence comprises a second end of the polynucleotide of interest, and wherein the second tag sequence is at least 27 nucleotides in length. In some embodiments, the first adaptor further comprises a binding moiety. In some embodiments, wherein the first tag sequence is at least 40 nucleotides in length. In some embodiments, the second tag sequence is at least 40 nucleotides in length.

In some embodiments, a solution is provided. The solution can comprise a circular nucleic acid molecule, the circular nucleic acid molecule comprising: a double stranded polynucleotide of interest comprising a first end and a second end; and at least one adaptor, wherein the at least one adaptor is covalently bonded to the first end and the second end of the double stranded polynucleotide of interest, thereby forming a circularized nucleic acid molecule, wherein the circular nucleic acid molecule further comprises a first nick between the first end of the double stranded polynucleotide of interest and the adaptor, and a second nick between the second end of the double stranded polynucleotide of interest and the adaptor, and wherein the first nick is on a different strand of the circular nucleic acid molecule than the second nick or gap; and a nick translation enzyme. In some embodiments, the nick translation enzyme comprises DNA polymerase I. In some embodiments, the solution further comprises a nick cleavage enzyme and wherein the nick translation enzyme is heat inactivated. In some embodiments, the solution further comprises a second circular nucleic acid molecule, the second circular nucleic acid molecule comprising: the double stranded polynucleotide of interest comprising the first end and the second end; and the at least one adaptor, covalently bonded to the first end and the second end of the double stranded polynucleotide of interest, thereby forming a second circularized nucleic acid molecule, wherein the second circular nucleic acid molecule comprises a third nick, wherein the third nick is more than 27 nucleotides away from the location between the first end of the double stranded polynucleotide of interest and the adaptor, and a fourth nick, wherein the fourth nick is more than 27 nucleotides away from the location between the second end of the double stranded polynucleotide of interest and the adaptor, and wherein the third nick is on a different strand of the circular nucleic acid molecule than the fourth nick. In some embodiments, the third nick is at least 50 nucleotides away from the location between the first end of the double stranded polynucleotide of interest and the adaptor. In some embodiments, the fourth nick is at least 50 nucleotides away from the location between the second end of the double stranded polynucleotide of interest and the adaptor. In some embodiments, the solution further comprises a nick cleavage enzyme, wherein the nick translation enzyme is heat inactivated.

In some embodiments, a method of forming a paired tag comprising a first tag sequence and a second tag sequence that together comprise at least part of a polynucleotide of interest is provided. The method can comprising ligating a first end of a double stranded polynucleotide of interest to at least one adaptor; ligating a second end of the double stranded polynucleotide of interest to at least one adaptor; forming a circular nucleic acid molecule comprising the double stranded polynucleotide of interest, a first nick comprising a first 3' end on a first strand of the circular nucleic acid molecule and a second nick comprising a second 3' end on a second strand of the circular nucleic acid molecule, wherein the first nick and the second nick are on different strands of the circular nucleic acid molecule; extending the first 3' end of the first strand of the circular nucleic acid molecule into a sequence of the double stranded polynucleotide of interest; and extending the second 3' end of the second strand of the circular nucleic acid molecule into a sequence of the double stranded polynucleotide of interest. In some embodiments, prior to extending the first 3' end, the first nick is located between the first end of the double stranded polynucleotide of interest and the at least one adaptor and the second nick is located between the second end of the double stranded polynucleotide of interest and the at least one adaptor. In some embodiments, the first and second ends of the double stranded polynucleotide of interest are connected to a same adaptor. In some embodiments, the adaptor comprises a first and a second adaptor, wherein the first adaptor is located on the first end of the double stranded polynucleotide of interest and wherein the second adaptor is located on the second end of the double stranded polynucleotide of interest upon formation of the circular nucleic acid molecule. In some embodiments, the first adaptor is connected to the second adaptor through a linking polynucleotide. In some embodiments, upon formation of the circular nucleic acid molecule, the first nick is located at an end of the first adaptor that is distal to an end of the first adaptor that is connected to the double stranded polynucleotide of interest and the second nick is located at an end of the second adaptor that is distal to an end of the second adaptor that is connected to the double stranded polynucleotide of interest. In some embodiments, the adaptors are ligated to a linking polynucleotide before the adaptors are ligated to the double stranded polynucleotide of interest. In some embodiments, the method further comprises digesting at least a part of the first strand of the circular nucleic acid molecule and digesting at least a part of the second strand of the circular nucleic acid molecule, wherein the digesting results in at least a portion of the double stranded polynucleotide of interest becoming single stranded, wherein the digesting occurs before the extending of the first and second 3' ends. In some embodiments, a 5' to 3' exonuclease is used to digest said nicked circular nucleic acid molecule. In some embodiments, the digestion is halted before the double stranded polynucleotide of interest becomes single stranded in its entirety. In some embodiments, the entire double stranded polynucleotide of interest is digested to a single stranded polynucleotide of interest. In some embodiments, a DNA polymerase is used to extend said nicked circular nucleic acid molecule. In some embodiments, the method further comprises digesting at least a part of the first strand of the circular nucleic acid molecule and digesting at least a part of the second strand of the circular nucleic acid molecule, wherein the digesting results in at least a portion of the double stranded polynucleotide of interest becoming single stranded, wherein the digesting occurs at the same time as the extending of the first and second 3' ends. In some embodiments, the digesting and the extending take place in the same reaction tube. In some embodiments, the extending of the first 3' end of the first strand of the circular nucleic acid molecule into a sequence of the double stranded polynucleotide of interest is achieved by nick translation. In some embodiments, the extending of the second 3' end of the second strand of the circular nucleic acid molecule into a sequence of the double stranded polynucleotide of interest is achieved by nick translation. In some embodiments, the first and second nicks are expanded into a first gap and second gap respectively. In some embodiments, an exonuclease is used to expand the first and second nicks into the first gap and second gap respectively. In some embodiments, the exonuclease comprises a T7 exonuclease. In some embodiments, the method further comprises performing a single strand dependent digest to release the paired DNA tag.

In some embodiments, a nicked linking polynucleotide is provided. The nicked linking polynucleotide can comprise a first adaptor comprising a first adaptor strand that is hybridized to a second adaptor strand, wherein the first adaptor strand lacks a phosphate group on its 5' end; a second adaptor comprising a third adaptor strand that is hybridized to a fourth adaptor strand, wherein the third adaptor strand lacks a phosphate group on its 5' end; and a linking polynucleotide comprising a first linking strand hybridized to a second linking strand, wherein the linking polynucleotide comprises a first end and a second end, wherein the first adaptor is attached to the first end of the linking polynucleotide such that a nick is present where the first adaptor strand lacks a phosphate group on its 5' end, wherein the second linking strand is attached to the second adaptor strand, wherein the second adaptor is attached to the second end of the linking polynucleotide such that a nick is present where the third adaptor strand of the second adaptor lacks a phosphate group on its 5' end, wherein the second strand of the linking polynucleotide is attached to the fourth adaptor strand. In some embodiments, the nicked linking polynucleotide further comprises a phosphate group on a 5' end of the second adaptor strand. In some embodiments, the nicked linking polynucleotide further comprises a phosphate group on a 5' end of the fourth adaptor strand. In some embodiments, there is no phosphate group on the further comprising a phosphate group on a 3' end of the second adaptor strand.

In some embodiments, a nicked linking polynucleotide is provided. The nicked linking polynucleotide can comprises a first double stranded adaptor; a double stranded linking polynucleotide, wherein the first double stranded adaptor is attached to a first end of a double stranded linking polynucleotide; and a second double stranded adaptor attached to a second end of the double stranded linking polynucleotide, wherein there is a first nick separating a first strand of the first adaptor and a first strand of the double stranded vector and a second nick separating a second strand of the second adaptor and a first strand of the double stranded vector, wherein the first nick and second nick are on different strands of the nicked vector.

In some embodiments, a method of preparing a paired tag is provided. The method can comprise providing a nicked linking polynucleotide comprising: a first adaptor comprising a first adaptor strand that is hybridized to a second adaptor strand, wherein the first adaptor strand lacks a phosphate group on its 5' end; a second adaptor comprising a third adaptor strand that is hybridized to a fourth adaptor strand, wherein the third adaptor strand lacks a phosphate group on its 5' end; and a linking polynucleotide comprising a first linking strand hybridized to a second linking strand, wherein the linking polynucleotide comprises a first end and a second end, wherein the first adaptor is attached to the first end of the linking polynucleotide such that a nick is present where the first adaptor strand lacks a phosphate group on its 5' end, wherein the second linking strand is attached to the second adaptor strand, wherein the second adaptor is attached to the second end of the linking polynucleotide such that a nick is present where the third adaptor strand of the second adaptor lacks a phosphate group on its 5' end, wherein the second strand of the linking polynucleotide is attached to the fourth adaptor strand. The method can further comprise ligating a first end of a double stranded polynucleotide of interest to the first adaptor and ligating a second end of the double stranded polynucleotide of interest to the second adaptor; and moving the first and second nicks into the double stranded polynucleotide of interest. In some embodiments, the method further comprises a single strand dependent digest to linearize the nicked linking polynucleotide. In some embodiments, the method further comprises ligating an internal adaptor into the linearized nicked linking polynucleotide. In some embodiments, the method further comprises amplifying at least one strand of the double stranded polynucleotide of interest. In some embodiments, the amplification is a PCR based amplification.

In some embodiments, a linear paired tag is provided. The linear paired tag can comprise a first tag sequence, wherein the first tag sequence comprises a first end of a polynucleotide of interest; a first adaptor covalently bonded to the first tag sequence; and a second tag sequence covalently bonded to the first adaptor, wherein the second tag sequence comprises a second end of the polynucleotide of interest, and wherein said linear paired tag lacks a type IIs restriction site and lacks a type III restriction site.

BRIEF DESCRIPTION OF THE DRAWINGS

The skilled artisan will understand that the drawings, described below, are for illustration purposes only. The drawings are not intended to limit the scope of the present teachings in any way.

DESCRIPTION OF VARIOUS EMBODIMENTS

Various embodiments disclosed herein are generally directed towards compositions and methods for making paired tags and paired tag libraries. A DNA "paired tag" is a length of nucleic acid sequence that includes two tags (nucleic acid sequences) that are generated from a polynucleotide of interest. Generally, each tag is a separate part of the polynucleotide of interest, allowing (but not limited to) the use of short read sequencing techniques on the separate tags, but still allowing one to associate the sequences of the two tags together during later sequence analysis because the tags are ultimately derived from the same polynucleotide fragment.

At present, there are a limited number of techniques that exist for making paired tags and paired tag libraries. The various techniques often have problems that can lead to short sequence reads and high cost. Until now, next-generation sequencing strategies have generally utilized type III restriction enzymes, such as EcoP15I (AB SOLiD™ sequencing) and MmeI (454 Life Sciences) to generate DNA paired tags. These strategies limit the length of the tags since EcoP15I and MmeI only generate 27 bp and 18 bp sequence tags respectively. Some of the embodiments described herein overcome this and other limitations.

Figure 1:
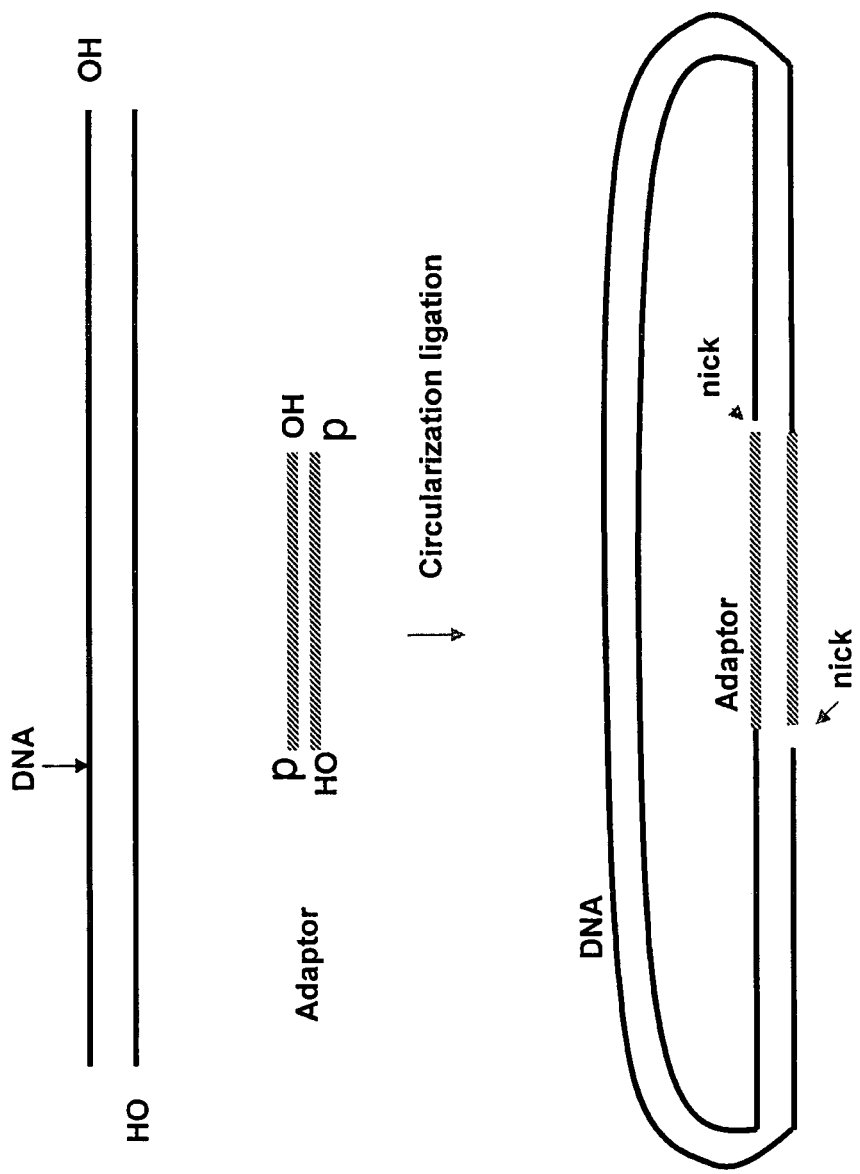
FIG. 1 depicts an embodiment for forming a nicked circular nucleic acid molecule.
Figure 2:
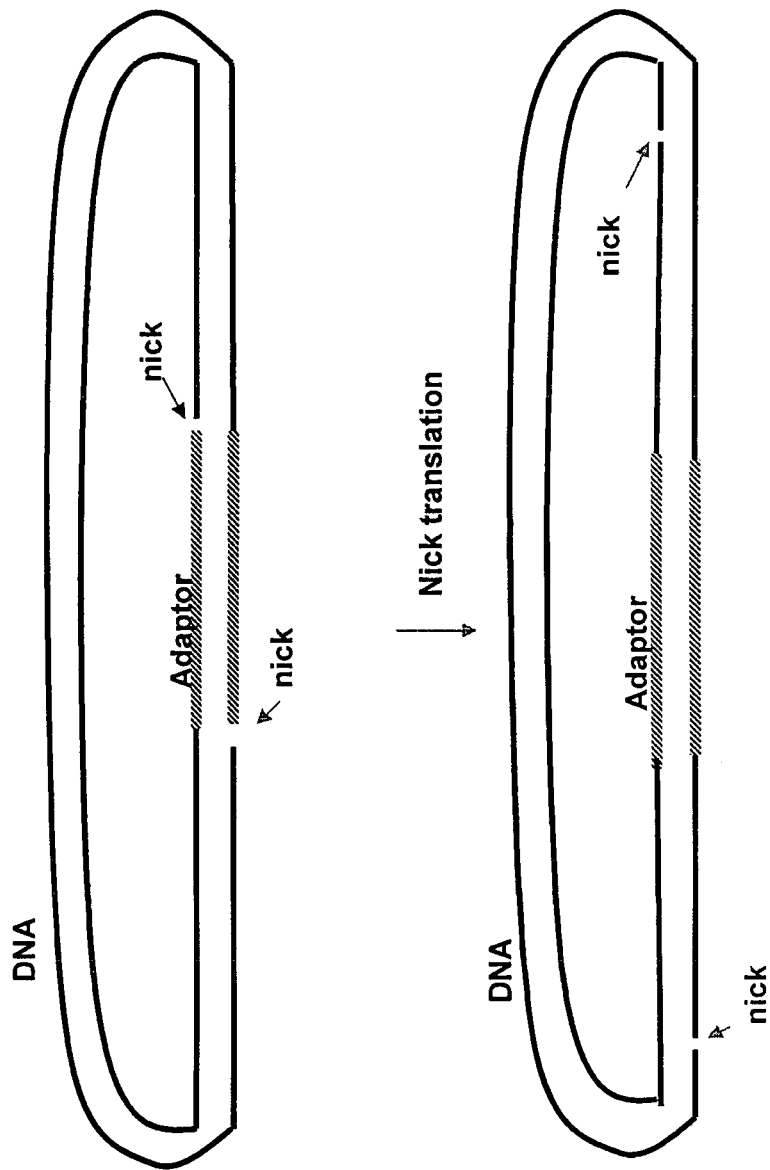
FIG. 2 depicts an embodiment for carrying out the nick translation step.

Some of the present embodiments involve methods that produce paired tag clones. One such embodiment is generally outlined in FIGS. 1 and 2. In FIG. 1, a double stranded polynucleotide of interest DNA fragment (denoted "DNA") is ligated at both ends to an adaptor to form a circular nucleic acid molecule. In the depicted embodiment, the double stranded polynucleotide of interest DNA fragment lacks a 5' phosphate residue at both the 5' end and the 3' end. The resulting circular nucleic acid molecule has a nick between the 5' end of the double stranded polynucleotide of interest DNA fragment and the adaptor, and a nick between the second end of the double stranded polynucleotide of interest DNA fragment and the adaptor. As shown schematically in FIG. 1, the nicks can be on different strand of the circular nucleic acid molecule. Next, as shown in FIG. 2, a nick translation reaction is performed. As shown schematically in FIG. 2, the nicks are moved in the 5' to 3' direction on each strand of the circular nucleic acid molecule into a position within the double stranded polynucleotide of interest DNA fragment. At this point, the paired tag clone can be released by cleaving the polynucleotide strand at the position that is opposite the nicks as shown schematically in FIG. 5.

The length of the nick translation reaction product, i.e., the distance the nick is moved, depends on the reaction conditions, such as reaction time, reaction temperature, the polymerase used, etc. As will be appreciated by one of skill in the art, the reaction conditions can be varied to control the length of the nick translation product. Thus, in some embodiments, one can control the length of the sequence tag produced. Additionally, in some embodiments, a binding moiety can be coupled to the adaptor, allowing one to attach the paired tag clone to, for example, a solid support. Furthermore, as shown schematically in FIG. 6, in some embodiments, primer adaptors can be attached to the ends of the paired tag clone. The primer adaptors can be used to amplify the paired tag clone using, for example, clonal amplification. The primer adaptors can also be used in sequencing reactions to sequence a portion of the paired tag clone.

In addition to the above, alternative techniques that simply extend a 3' end into a polynucleotide of interest are also disclosed herein. Thus, 3' extension can also be used, and nick translation itself is not required. In addition, various nicked linking polynucleotides are also disclosed herein that simplify the addition of nicks outside of and into a polynucleotide of interest.

As will be appreciated by one of skill in the art, the ability to make paired tags having a longer sequence tag can have great benefit, especially for large sequencing projects, such as genome sequencing.

The above and additional embodiments are discussed in mote detail below, after a brief discussion of the definitions some of the terms used in the specification.

DEFINITIONS AND EMBODIMENTS

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the invention.

Unless otherwise defined, scientific and technical terms used in connection with the invention described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques of described herein are those well known and commonly used in the art.

As utilized in accordance with the embodiments provided herein, the following terms, unless otherwise indicated, shall be understood to have the following meanings:

"Nucleotide" refers to a phosphate ester of a nucleoside, as a monomer unit or within a nucleic acid. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group can include sulfur substitutions for the various oxygens, e.g. .alpha.-thio-nucleotide 5'-triphosphates. For a review of nucleic acid chemistry, see: Shabarova, Z. and Bogdanov, A. Advanced Organic Chemistry of Nucleic Acids, VCH, New York, 1994.

The term "nucleic acid" refers to natural nucleic acids, artificial nucleic acids, analogs thereof, or combinations thereof.

As used herein, the terms "polynucleotide" and "oligonucleotide" are used interchangeably and mean single-stranded and double-stranded polymers of nucleotide monomers (nucleic acids), including, but not limited to, 2'-deoxyribonucleotides (nucleic acid) and ribonucleotides (RNA) linked by internucleotide phosphodiester bond linkages, e.g. 3'-5' and 2'-5', inverted linkages, e.g. 3'-3' and 5'-5', branched structures, or analog nucleic acids. Polynucleotides have associated counter ions, such as $H^+$, $NH_4^+$, trialkylammonium, $Mg^{2+}$, $Na^+$ and the like. A polynucleotide can be composed entirely of deoxyribonucleotides, entirely of ribonucleotides, or chimeric mixtures thereof. Polynucleotides can be comprised of nucleobase and sugar analogs. Polynucleotides typically range in size from a few monomeric units, e.g. 5-40 when they are more commonly frequently referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine.

Polynucleotides are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also can be said to have 5' and 3' ends.

A "first end" and a "second end" of a polynucleotide refer to the 5' end or the 3' end of the polynucleotide. Either the first end or second end of a polynucleotide can be the 5' end or the 3' end of the polynucleotide; the terms "first" and "second" are not meant to denote that the end is specifically the 5' end or the 3' end.

The term "end region" as used herein refers the region of a polynucleotide located at the 5' end or the 3' end.

"DNA fragment of interest," "polynucleotide of interest," "target polynucleotide," "DNA template" or "template polynucleotide" denotes the DNA fragment or polynucleotide that one is interested in identifying, characterizing or manipulating. As used herein, the term "template" and "polynucleotide of interest" refers to nucleic acid that is acted upon, such as, for example, nucleic acid that is to be mixed with polymerase. In some embodiments, the polynucleotide of interest is a double stranded polynucleotide of interest ("DSPI").

The phrases "different strand of a polynucleotide" and "different strand of a nucleic acid molecule" as used herein refer to a nucleic acid strand of a duplex polynucleotide that is not from the same side as another strand of the duplex polynucleotide.

As used herein "tag," "sequence tag" or "tag sequence" refer to a subsequence of a polynucleotide of interest.

A "paired tag," also known as a "PT," "tag mate pair," "mate pair," "MP," or "paired-end" contains two tags (each a nucleic acid sequence) that are from each end region of a polynucleotide of interest. Thus, a paired tag includes sequence fragment information from two parts of a polynucleotide. In some embodiments, this information can be combined with information regarding the polynucleotide's size, such that the separation between the two sequenced fragments is known to at least a first approximation. This information can be used in mapping where the sequence tags came from.

Figure 5:
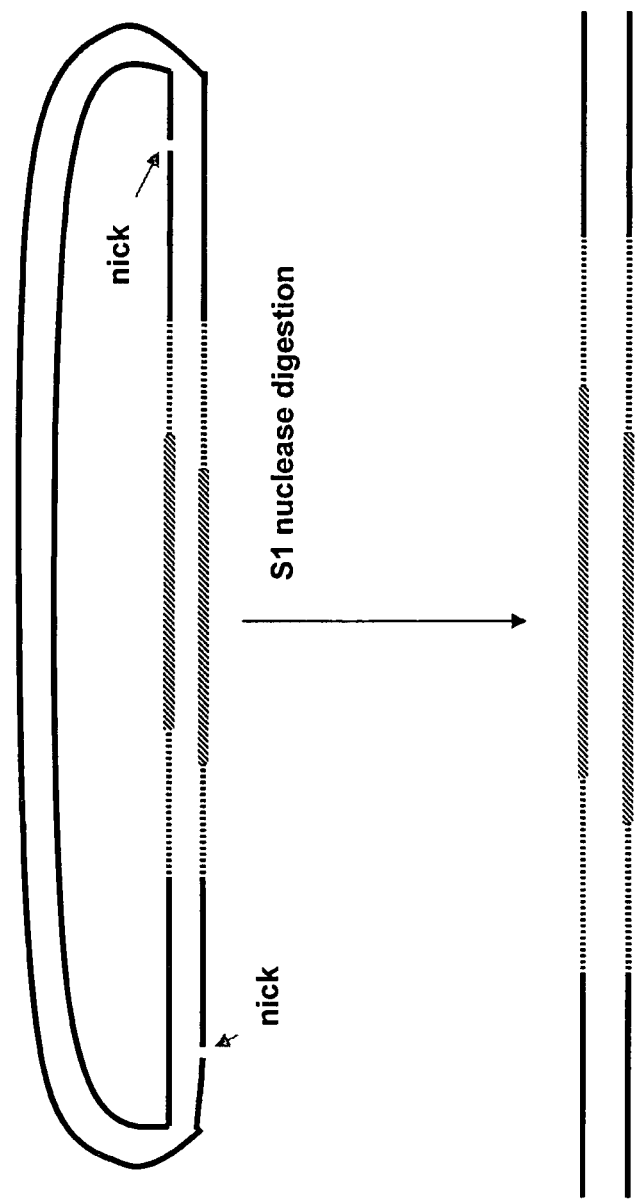
FIG. 5 depicts an embodiment for linearizing the circular nucleic acid molecule.

A paired tag is "released" or is part of a "released paired tag" when the paired tag is linear. An example of this is shown in FIG. 5. As will be appreciated by one of skill in the art, the released paired tag can be formed by cleavage of one or both of the nicks after the nick translation. In some embodiments, where nick translation is allowed to proceed until completion (the meeting of both nicks on the circular nucleic acid molecule), linearization (i.e., paired tag release) can occur without the need of additional enzymes. As will be appreciated by one of skill in the art, the "paired tag" can be part of a larger structure, such as the circularized nucleic acid molecule, before it is released.

A "paired tag clone" refers to a cloned polynucleotide containing a paired tag. This simply denotes that the paired tag is derived from some manipulation of the starting polynucleotide. In some embodiments, a paired tag clone comprises a first tag sequence and a second tag sequence separated by an adaptor. In some embodiments, the clone is derived from a single starting polynucleotide molecule.

As used herein the term "paired tag library" refers to a collection of paired tag clones that includes all or part of the genetic material of an organism.

"Circular nucleic acid molecule" denotes a nucleic acid molecule that is in a loop. In some embodiments, the loop can contain one or more nicks or gaps. In preferred embodiments, the loop can contain a nick or gap on each strand of the duplex polynucleotide.

As used herein, "starting polynucleotide" denotes the original polynucleotide from that the polynucleotide of interest can be derived from. For example, a sample from a cell, where the starting polynucleotide is fragmented into acceptable sizes to serve as polynucleotides of interest. Of course, the options and variations of the starting polynucleotide are at least as broad as the options for the polynucleotide of interest.

As used herein, the terms "nick" refers to a point in a double stranded polynucleotide where there is no phosphodiester bond between adjacent nucleotides of one strand of the polynucleotide. The term "nick" encompasses both nicks and gaps. A nick and/or gap can be described as comprising a 3' end and a 5' end and/or sides. These sides or ends comprise the nucleotide on the very 3' end of one polynucleotide and the nucleotide on the very 5' end of a second polynucleotide. As noted above, there is no phosphodiester bond between these two nucleotides. The second strand, which is hybridized to the two polynucleotides described above, does include one or more phosphodiester bond(s) and 0 or more nucleotide(s) between the corresponding nucleotides that lack the phosphodiester on the first strand.

As used herein, the phrase "cleaving the circular nucleic acid molecule at a first translated nick" denotes that the nucleic acid strand that is hybridized to the nicked strand is cleaved at a position based upon the presence of the nick. In some embodiments, the nucleic acid strand that is hybridized to the nicked strand is cleaved at a position opposite the nick.

As used herein, the terms "gap" refers to a region of a double stranded polynucleotide where one strand is missing one or more nucleotide resides. In some embodiments, the nucleotide residue at the 3' end of the gap can lack a 5' phosphate residue.

The term "nick translation" as used herein refers to a coupled polymerization/degradation or strand displacement process that is characterized by a coordinated 5' to 3' DNA polymerase activity and a 5' to 3' exonuclease activity or 5' to 3' strand displacement. As will be appreciated by one of skill in the art, a "nick translation," as the term is used herein, can occur on a nick or to a gap. As will be appreciated by one of skill in the art, in some embodiments, the "nick translation" of a gap entails the insertion of appropriate nucleotides in order to form a traditional nick that simply lacks a phosphodiester bond, which is then translated.

As used herein, the phrases "nick is translated into the DNA fragment of interest" and "nick is translated into the polynucleotide of interest" refers to the translocation of a nick to a position in the strand that includes the nick that is within the DNA fragment or polynucleotide of interest.

Figure 14:
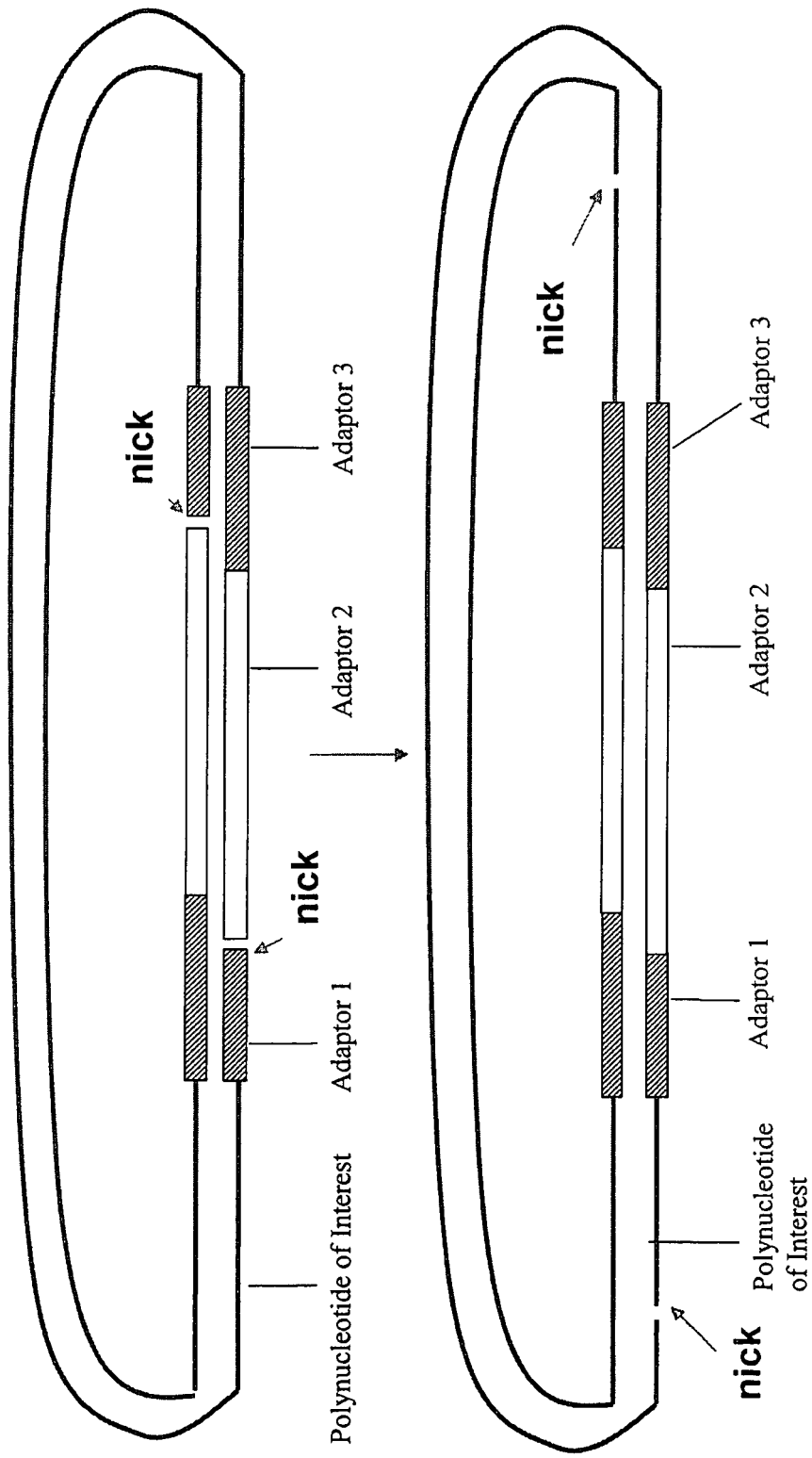
FIG. 14 depicts an embodiment involving a nick translation step.
Figure 17:
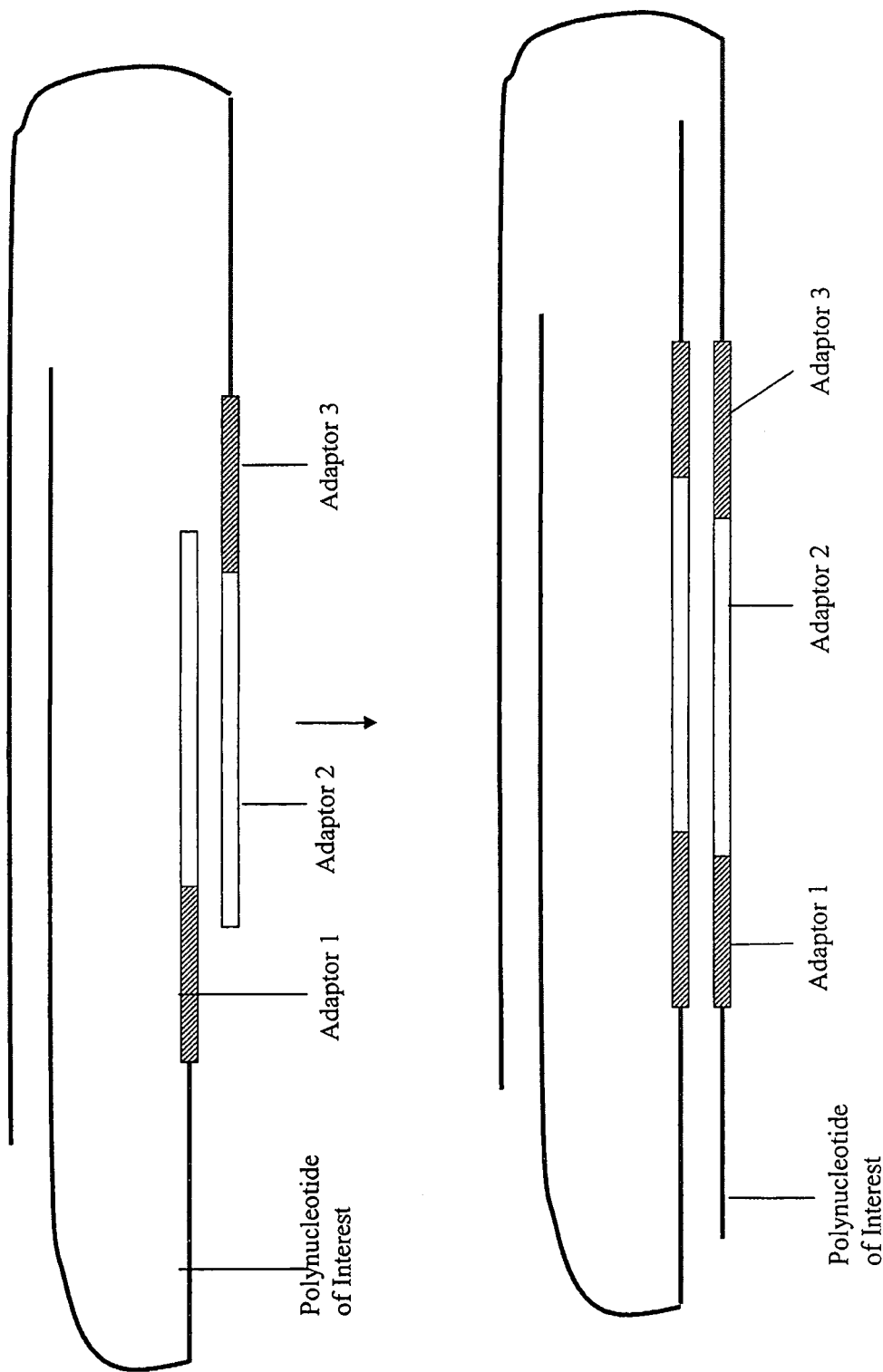
FIG. 17 depicts an alternative embodiment for forming paired tags continued from FIG. 16.
Figure 20:
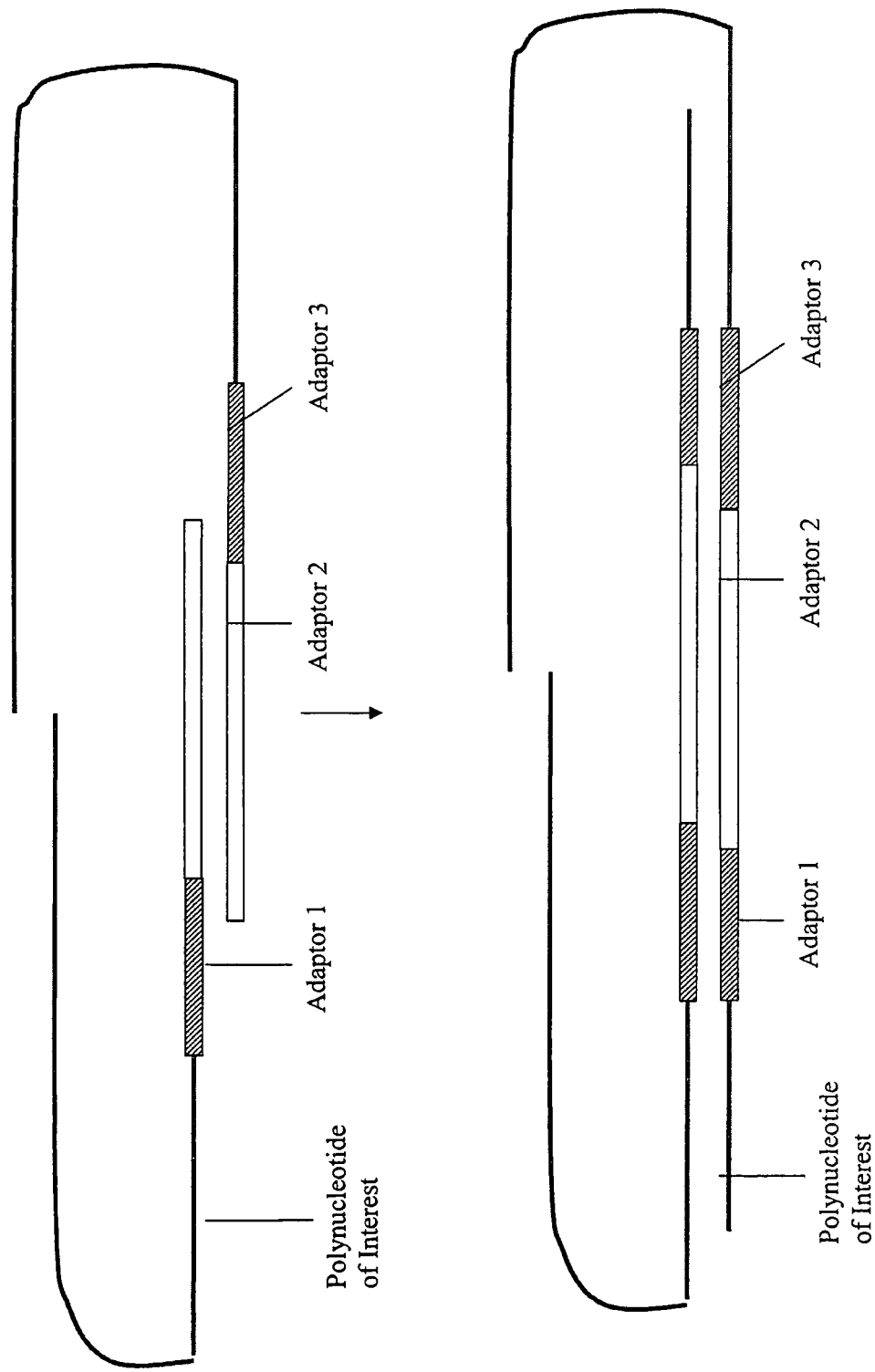
FIG. 20 depicts an alternative embodiment for forming paired tags continued from FIG. 19.

As used herein, the phrase "extending the first 3' end of the first strand of the circular nucleic acid molecule" or "moving the first and second nicks" into a sequence of the double stranded polynucleotide of interest denotes that the 3' end is extended at least to the point that its sequence is complementary to one of the strands of the polynucleotide of interest. Examples of an extension of the 3' ends are shown in FIG. 14, FIG. 17, and FIG. 20. Simple nick translations that move or extend a 3' end into a sequence such that the created sequence has a sequence that is complementary to the polynucleotide of interest will also qualify as being moved or extended.

As used herein, the phrases "into a sequence of the double stranded polynucleotide of interest" or "into a sequence of the double stranded polynucleotide of interest" denotes that an end or nick has been moved or extended such that the extended portion is complementary to a section of one strand of the polynucleotide of interest. As will be appreciated by one of skill in the art, the "double stranded" polynucleotide of interest, need not be double stranded just before the 3' end is moved or extended into it (even when the phrase "into a sequence of the double stranded polynucleotide of interest" is employed). In some embodiments, e.g., when nick translation is used, the polynucleotide of interest will primarily remain double stranded, although the nick will effectively transfer the nucleotides from being associated with the double stranded polynucleotide of interest to the strand that is covalently linked to the adaptor.

A "nicked linking polynucleotide" denotes a linking polynucleotide that comprises a nick and at least one adaptor. In some embodiments, the linking polynucleotide is or is derived from a vector or plasmid; however, this is not a requirement.

As used herein, the term "adaptor" denotes a molecule that can be used for manipulation of a polynucleotide of interest. In some embodiments, the adaptors can be used for circularization of a nucleic acid. In some embodiments, the adaptor can be used to introduce a nick. In some embodiments, the adaptors can be used for amplification of a paired tag clone. In some embodiments, the adaptors can be used in sequencing reactions for sequencing a portion of a paired tag clone. In some embodiments, the adaptor can have one or more ends that lack a 5' phosphate residue. In some embodiments, the adaptor comprises a nucleic acid. In some embodiments, an adaptor can comprise, consist, or consist essentially of at least one priming site. In some embodiments, the priming site can be useful in PCR processes. In some embodiments, the designation of an adaptor as "P1" or "P2" denotes an adaptor that can include a priming site. In addition, such adaptors can be referred to as "primer" adaptors. Of course, not all adaptors require a priming site. As will be appreciate by one of skill in the art, embodiments disclosed herein involving a "primer adaptor" can also be practiced using a generic adaptors. That is, in some embodiments, the primer adaptors are replaced with simple adaptors, that need not include priming sites.

"Bar code sequence" and "identifying code sequence" denote a nucleic acid sequence that is sufficient to allow for the identification of an adaptor, a gene, or sequence of interest. The bar code sequence can be, but need not be, a small section of the original nucleic acid sequence on which the identification is to be based. In some embodiments the bar code is 5-30 nucleic acids long. In some embodiments, the bar code is comprised of analog nucleotides, such as L-DNA, LNA, PNA, etc.

A nucleic acid sequence, fragment, or paired tag clone having "compatible ends" means that the ends are compatible with joining to another nucleic acid sequence, fragment or paired tag clone as provided herein. Compatible ends can be "sticky ends" having a 5' and/or 3' overhang, or alternatively, compatible ends can be "blunt ends" having no 5' and/or 3' overhang. In generally, sticky ends can permit sequence-dependent ligation, whereas blunt ends can permit sequence-independent ligation. Compatible ends can be produced by any known methods that are standard in the art. For example, compatible ends of a nucleic acid sequence can be produced by restriction endonuclease digestion of the 5' and/or 3' end.

As used herein, the terms "restriction endonucleases" and "restriction enzymes" refer to bacterial enzymes, each of which cut double-stranded DNA at or near a specific nucleotide sequence.

As used herein, "nick cleavage enzymes" refer to enzymes that can cleave through a remaining nucleic acid strand at or near a nick. Examples of such enzymes include, without limitation, S1 nuclease, mung bean nuclease, nuclease P1, and nuclease BAL-31. As the term nick also encompasses gaps, enzymes that also cleave single stranded polynucleotides also fall into the category of nick cleavage enzymes. For example, single strand specific endonucleases are also included in this group. In addition, single strand specific exonucleases are also included in this term in embodiments in which the ends of the polynucleotides of interest are single stranded (e.g., FIG. 21).

The terms type IIs and type III restriction endonuclease encompass restriction endonucleases that cleave outside of their recognition sequence. Thus, the terms encompass restriction endonucleases that may technically be categorized as other than type III or type IIs, for example, type IV enzymes (e.g., AcuI).

As used herein "3' tailing" refers to the addition of one or more nucleotides to the 3' ends of a polynucleotide.

The term "immobilized" is art-recognized and, when used with respect to a nucleic acid, refers to a condition in which the nucleic acid is attached to a surface with an attractive force stronger than attractive forces that are present in the intended environment of use of the surface, and that act on the species.

As used herein, the term "nucleic acid sequence" or "nucleobase sequence" is any section of a polymer that comprises nucleobase-containing subunits. Non-limiting examples of suitable polymers or polymer segments include oligonucleotides, oligoribonucleotides, peptide nucleic acids and analogs and chimeras thereof.

An "analog" nucleic acid is a nucleic acid that is not normally found in a host to which it is being added or in a sample that is being tested. For example, the target sequence will not comprise an analog nucleic acid. This includes an artificial, synthetic, or combination thereof, nucleic acid. Thus, for example, in one embodiment, PNA is an analog nucleic acid, as is L-DNA and LNA (locked nucleic acids), iso-C/iso-G, L-RNA, O-methyl RNA, or other such nucleic acids. In one embodiment, any modified nucleic acid will be encompassed within the term analog nucleic acid. In another embodiment an analog nucleic acid can be a nucleic acid that will not substantially hybridize to native nucleic acids in a system, but will hybridize to other analog nucleic acids; thus, PNA would not be an analog nucleic acid, but L-DNA would be an analog nucleic acid. For example, while L-DNA can hybridize to PNA in an effective manner, L-DNA will not hybridize to D-DNA or D-RNA in a similar effective manner. Thus, nucleotides that can hybridize to a probe or target sequence but lack at least one natural nucleotide characteristic, such as susceptibility to degradation by nucleases or binding to D-DNA or D-RNA, are analog nucleotides in some embodiments. Of course, the analog nucleotide need not have every difference.

The term "organism" is used herein to indicate any living or nonliving entity that comprises nucleic acid that is capable of being replicated and is of interest for sequence determination. It includes, without limitation, plasmids, viruses, prokaryotic, archaebacterial and eukaryotic cells, cell lines, fungi, protozoa, plants, animals, etc.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but can alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "nucleic acid sequencing chemistry" as used herein refers to a type of chemistry and associated methods used to sequence a polynucleotide to produce a sequencing result. A wide variety of sequencing chemistries are known in the art. Examples of various types of sequencing chemistries useful in various embodiments disclosed herein include, but are not limited to, Maxam-Gilbert sequencing, chain termination methods, dye-labeled terminator methods, sequencing using reversible terminators, sequencing of nucleic acid by pyrophosphate detection ("pyrophosphate sequencing" or "pyrosequencing") and sequencing by ligation. Such sequencing chemistries and corresponding sequencing reagents are described, for example, in U.S. Pat. Nos. 7,057,026, 5,763,594, 5,808,045, 6,232,465, 5,990,300, 5,872,244, 6,613,523, 6,664,079, 5,302,509, 6,255,475, 6,309836, 6,613,513, 6,841,128, 6,210,891, 6,258,568, 5,750,341, 6,306,597, PCT Publication Nos. WO91/06678A1, WO93/05183A1, WO6074351A2, WO03054142A2, WO03004690A2, WO07002204A2, WO07002204A2, WO06084132A2 and WO06073504A2, which are incorporated by reference in their entireties.

As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a polynucleotide of interest sequence in a mixture of genomic DNA without cloning or purification. This process for amplifying the polynucleotide of interest sequence consists of introducing a large excess of two oligonucleotide primers to the DNA mixture containing the desired polynucleotide of interest sequence, followed by a precise sequence of thermal cycling in the presence of a DNA polymerase. The two primers are complementary to their respective strands of the double stranded polynucleotide of interest sequence. To effect amplification, the mixture is denatured and the primers then annealed to their complementary sequences within the polynucleotide of interest molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired polynucleotide of interest. The length of the amplified segment of the desired polynucleotide of interest is determined by the relative positions of the primers with respect to each other, and therefore, this length is a controllable parameter. By virtue of the repeating the process, the method is referred to as the "polymerase chain reaction" (hereinafter "PCR"). Because the desired amplified segments of the polynucleotide of interest sequence become the predominant sequences (in terms of concentration) in the mixture, they are said to be "PCR amplified".

With PCR, it is possible to amplify a single copy of a specific polynucleotide of interest in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient polynucleotides of interest for subsequent PCR amplifications.

As used herein, the terms "PCR product," "PCR fragment" and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid polynucleotide of interest and the amplification enzyme. Typically, amplification reagents along with other reaction components are placed and contained in a reaction vessel (test tube, microwell, etc.).

"Clonal amplification" refers to the generation of many copies of an individual molecule. Various methods known in the art can be used for clonal amplification. For example, emulsion PCR is one method, and involves isolating individual DNA molecules along with primer-coated beads in aqueous bubbles within an oil phase. A polymerase chain reaction (PCR) then coats each bead with clonal copies of the isolated library molecule and these beads are subsequently immobilized for later sequencing. Emulsion PCR is used in the methods published by Marguilis et al. and Shendure and Porreca et al. (also known as "polony sequencing", commercialized by Agencourt and recently acquired by Applied Biosystems). Margulies, et al. (2005) *Nature* 437: 376-380; Shendure et al., *Science* 309 (5741): 1728-1732. Another method for clonal amplification is "bridge PCR," where fragments are amplified upon primers attached to a solid surface. These methods, as well as other methods of clonal amplification, both produce many physically isolated locations that each contain many copies derived from a single molecule polynucleotide fragment.

"Binding moiety" is a molecule that can bind to a purifying moiety under appropriate conditions. The interaction between the binding moiety and purifying moiety is strong enough to allow enrichment and/or purification of the binding moiety and a molecule associated with it, for example, a paired tag clone. Biotin is an example of a binding moiety. In some embodiments, by coupling a binding moiety to an adaptor, binding of the binding moiety to a purifying moiety target allows purification of the paired tag clone. In some embodiments, the purifying moiety can be present on a solid support.

A "purifying moiety" is a molecule that binds to the binding molecule. An exemplary purifying moiety for biotin is streptavidin.

The term "solid support" refers to any solid phase material upon which an oligonucleotide is synthesized, attached or immobilized. Solid support encompasses terms such as "resin", "solid phase", and "support". A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as, for example, glass, silica, controlled-pore-glass (CPG), or reverse-phase silica. The configuration of a solid support can be in the form of beads, spheres, particles, granules, a gel, a surface, or combinations thereof. Surfaces can be planar, substantially planar, or non-planar. Solid supports can be porous or non-porous, and can have swelling or non-swelling characteristics. A solid support can be configured in the form of a well, depression or other container, vessel, feature or location or position. A plurality of solid supports can be configured in an array at various locations, e.g. positions, addressable for robotic delivery of reagents, or by detection means including scanning by laser illumination and confocal or deflective light gathering.

"Array" or "microarray" encompasses an arrangement of polynucleotides present on a solid support or in an arrangement of vessels. Certain array formats are referred to as a "chip" or "biochip" (M. Schena, Ed. Microarray Biochip Technology, BioTechnique Books, Eaton Publishing, Natick, Mass. (2000)). An array can comprise a low-density number of addressable locations, e.g. 1 to about 12, medium-density, e.g. about a hundred or more locations, or a high-density number, e.g. a thousand or more. Typically, the array format is a geometrically-regular shape that allows for fabrication, handling, placement, stacking, reagent introduction, detection, and storage. The array can be configured in a row and column format, with regular spacing between each location. Alternatively, the locations can be bundled, mixed, or homogeneously blended for equalized treatment and/or sampling. An array can comprise a plurality of addressable locations configured so that each location is spatially addressable for high-throughput handling, robotic delivery, masking, and/or sampling of reagents and/or by detection means including scanning by laser illumination and confocal and/or deflective light gathering. The array can comprise one or more "addressable locations," e.g. "addressable positions," that is, physical locations that comprise a known type of molecule.

The following passages describe different embodiments of the various embodiments in greater detail. Each step or feature of the various embodiments can be combined with any other step or feature unless clearly indicated to the contrary.

Exemplary Embodiments

As noted above, a paired-end sequencing approach can provide more information from sequencing two stretches each of "n" bases from a single polynucleotide of interest than from sequencing "n" bases from each of two independent polynucleotides of interest in a random fashion. However, until now, read lengths have been limited by short sequence tag lengths. For example, previous strategies for making paired tags using type III restriction enzymes only generated up to 27 bp sequence tags. The two tag sequences on a given mate pair clone may be of different lengths or the same length.

In some embodiments, one can use circularization and nick translation in order to control and/or increase the length of sequence tags in paired tag clones. In some embodiments, the disclosed methods can be used to prepare paired tag clones from a nucleic acid molecule of interest.

One such embodiment is depicted in FIG. 1 and FIG. 2. As shown in FIG. 1, an adaptor is attached to a double stranded polynucleotide of interest so as to allow circularization of the double stranded polynucleotide of interest. Importantly, after the circularization, there is at least one nick or gap present in the circularized nucleic acid sequence, and in some embodiments, there are two nicks or gaps, one on each strand of the circularized nucleic acid sequence. As shown in FIG. 1, one nick or gap is initially located between a first end of the adaptor and a first end of the double stranded polynucleotide of interest on one strand, while a second nick or gap is located between a second end of the adaptor and the second end of the double stranded polynucleotide of interest. Next, as shown in FIG. 2, a nick translation reaction is carried out via a nick translation enzyme. This moves at least one nick into the double stranded polynucleotide of interest. The desired distance that the nick is moved can vary depending upon the goals of the user; however, in some embodiments, one allows the nick translation reaction to occur until the nick has moved more than 10, 20, or 27 nucleotides into the double stranded polynucleotide of interest. Following this, the circularized nucleic acid sequence can be linearized at or near a nick location via an enzyme that cleaves at or near a nick, such as a single-strand specific nuclease, resulting in a released paired tag. Enzymes for linearizing the circularized nucleic acid at a nick location include, for example without limitation, S1 nuclease, nuclease P1, nuclease BAL31, nuclease from *Neurospora crassa*, nuclease from *Ustilago maydis*, and mung bean nuclease.

Figure 3:
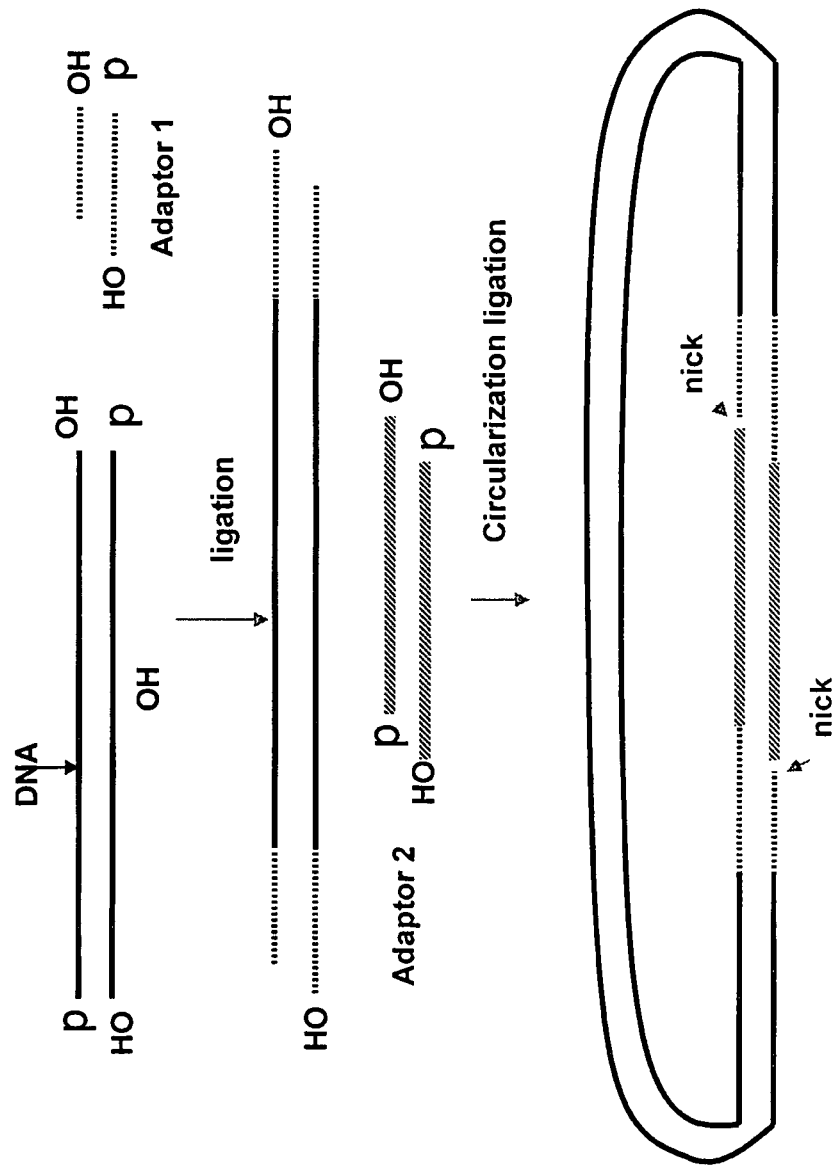
FIG. 3 depicts an embodiment for forming a nicked circular nucleic acid.
Figure 4:
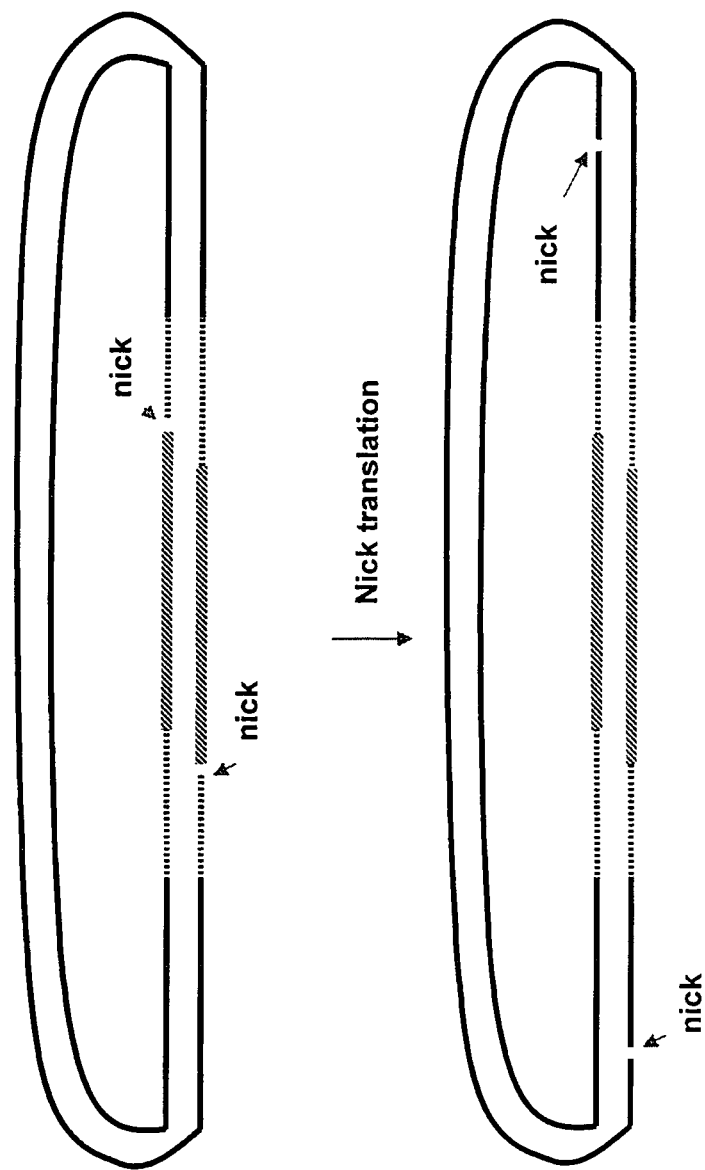
FIG. 4 depicts an embodiment for carrying out the steps of an embodiment of the invention.

Another embodiment is depicted in FIG. 3, FIG. 4, and FIG. 5. In this embodiment, multiple adaptors can be employed. In a first step, one can attach a first type of adaptor, having a sticky end (or a blunt end in some embodiments), to both the first and second ends of the double stranded polynucleotide of interest. Following this, one can add a second type of adaptor that will have an appropriate overhang to allow it to be ligated into the overhang present in the first adaptor and also serve to circularize the molecule. As noted in the first example, at least one, if not two nicks or gaps will be present after the circularization ligation event via the second adaptor. As before (and as demonstrated in FIG. 4), this will allow for the nicks to be translated via a nick translation enzyme at least partially into the double stranded polynucleotide of interest, as shown in FIG. 5. This translated circularized nucleic acid sequence can then be linearized by any suitable enzyme, as shown in FIG. 5, thereby resulting in the paired tag.

Figure 10:
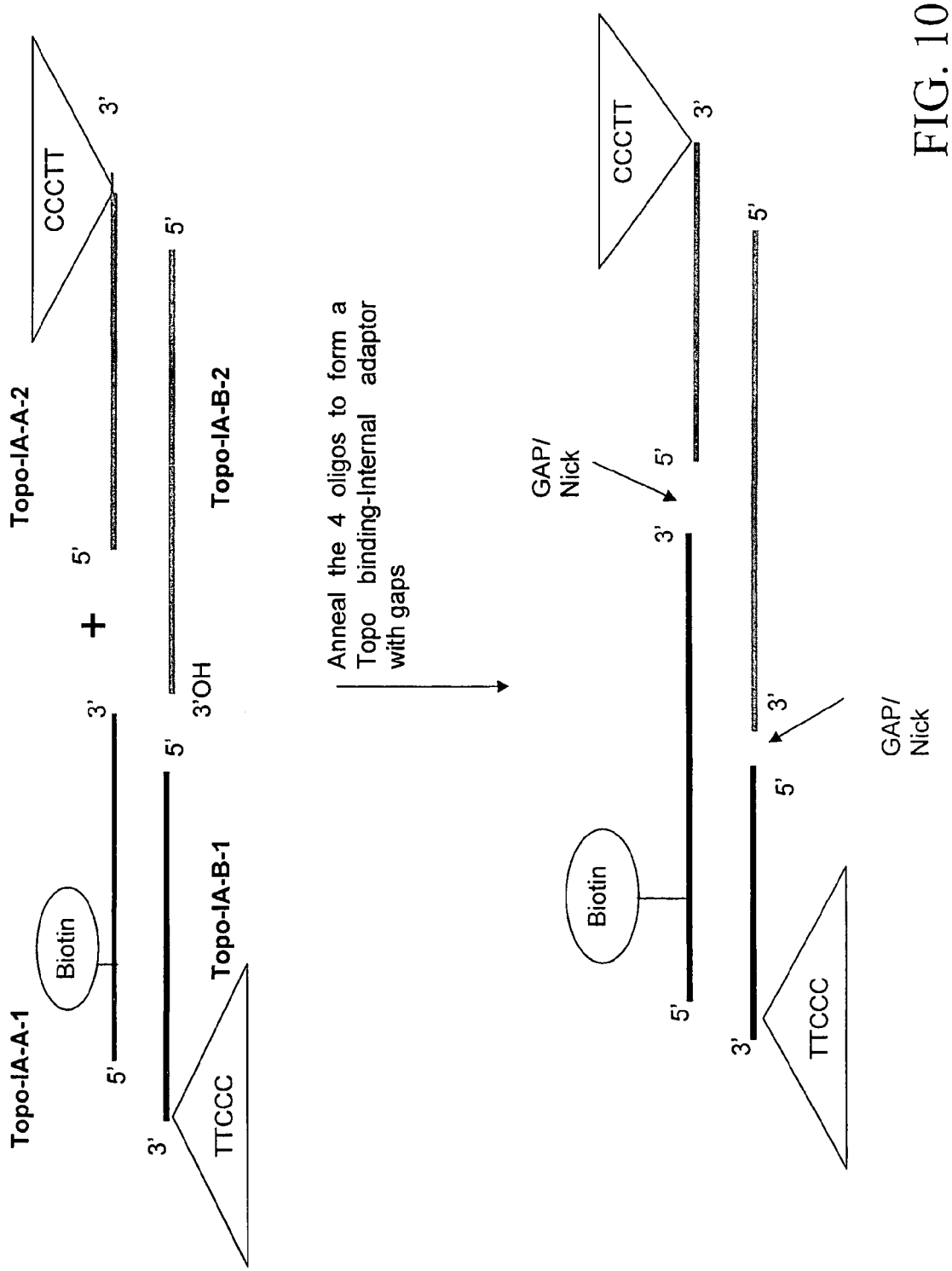
FIG. 10 depicts an embodiment for forming an adaptor having Topoisomerase I binding sites and nicks. The triangles indicate the location of the Topoisomerase I recognition sites.
Figure 11:
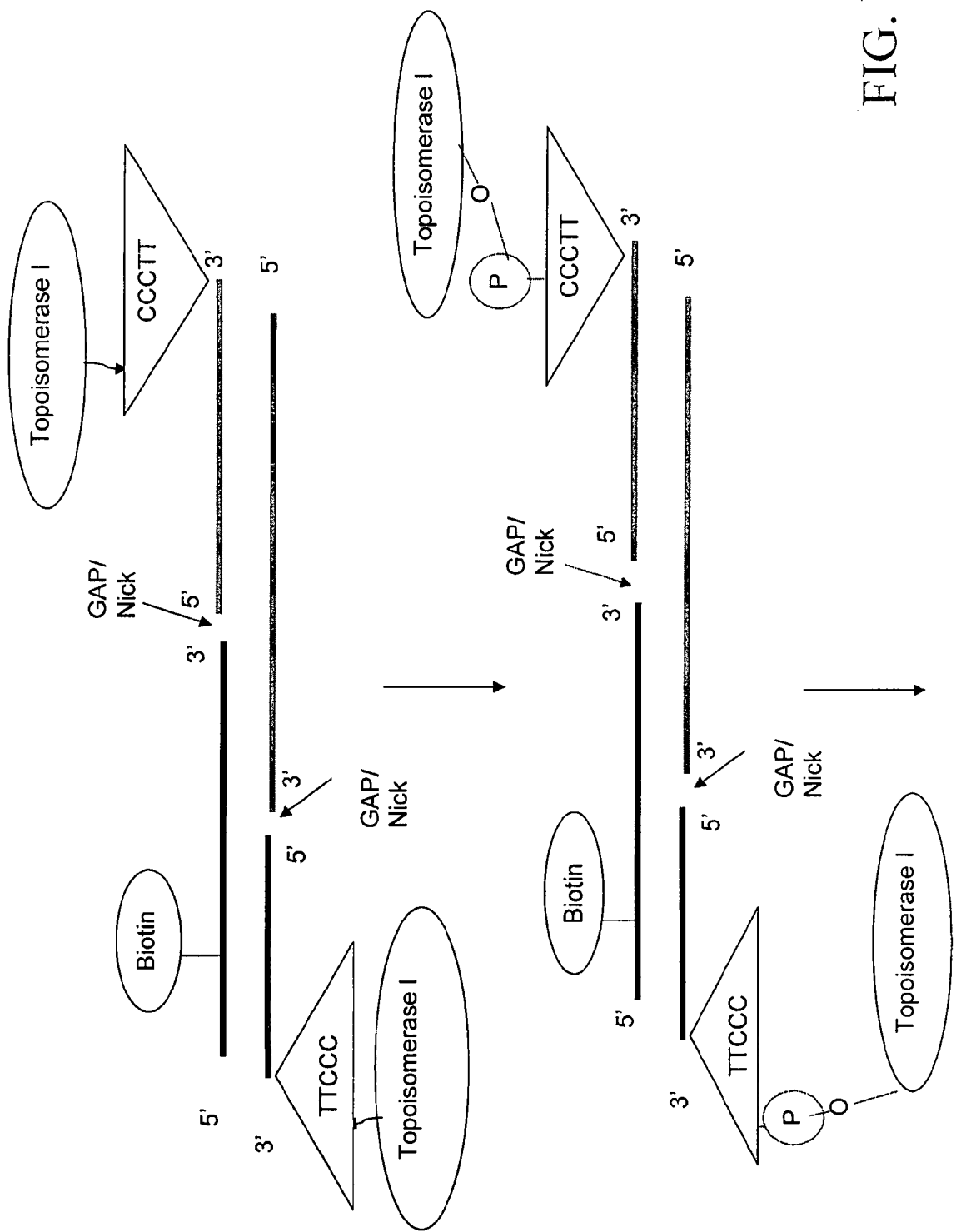
FIG. 11 depicts an embodiment for forming a Topoisomerase I-adaptor complex.
Figure 12:
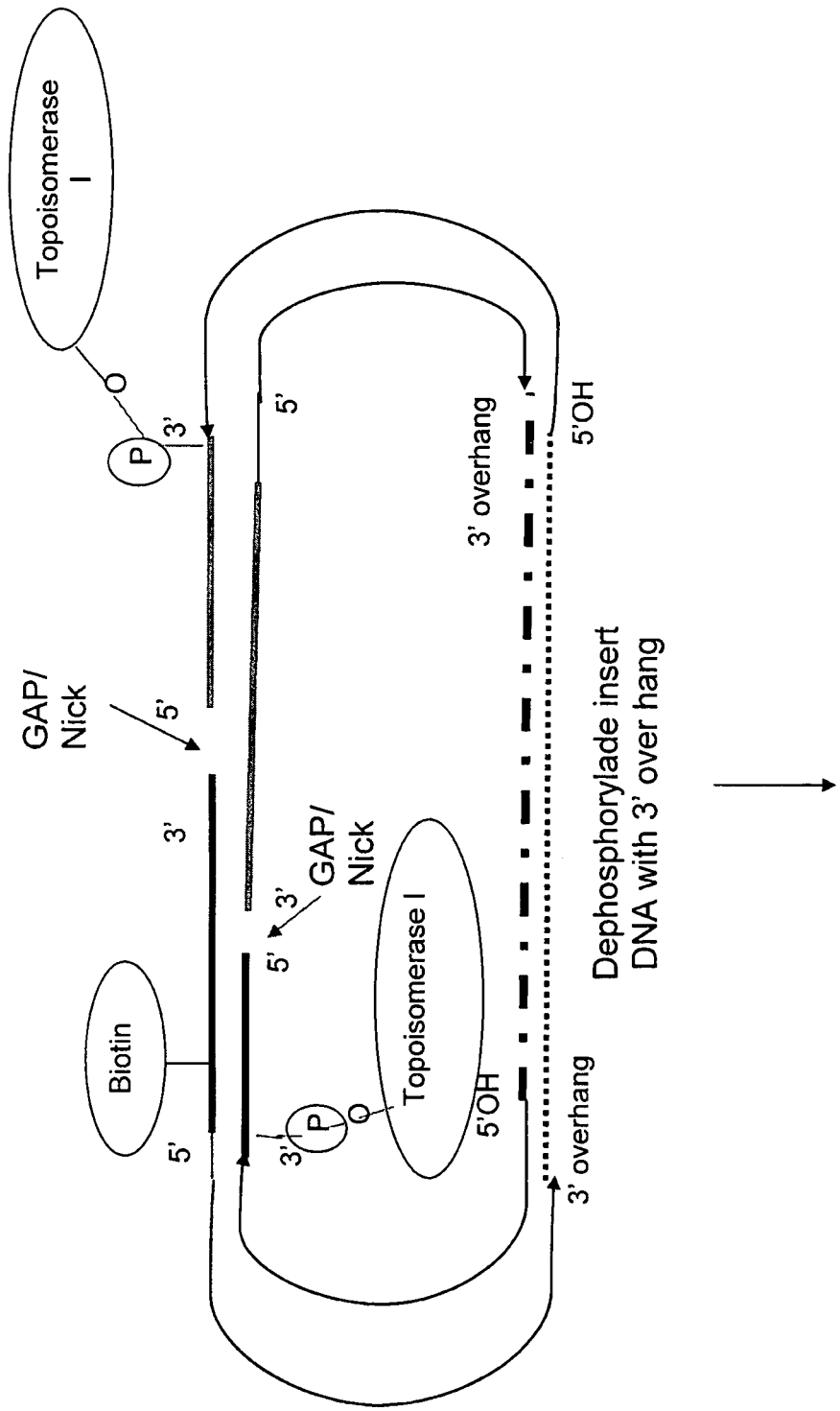
FIG. 12 depicts an embodiment for forming a nicked circular nucleic acid molecule.
Figure 13:
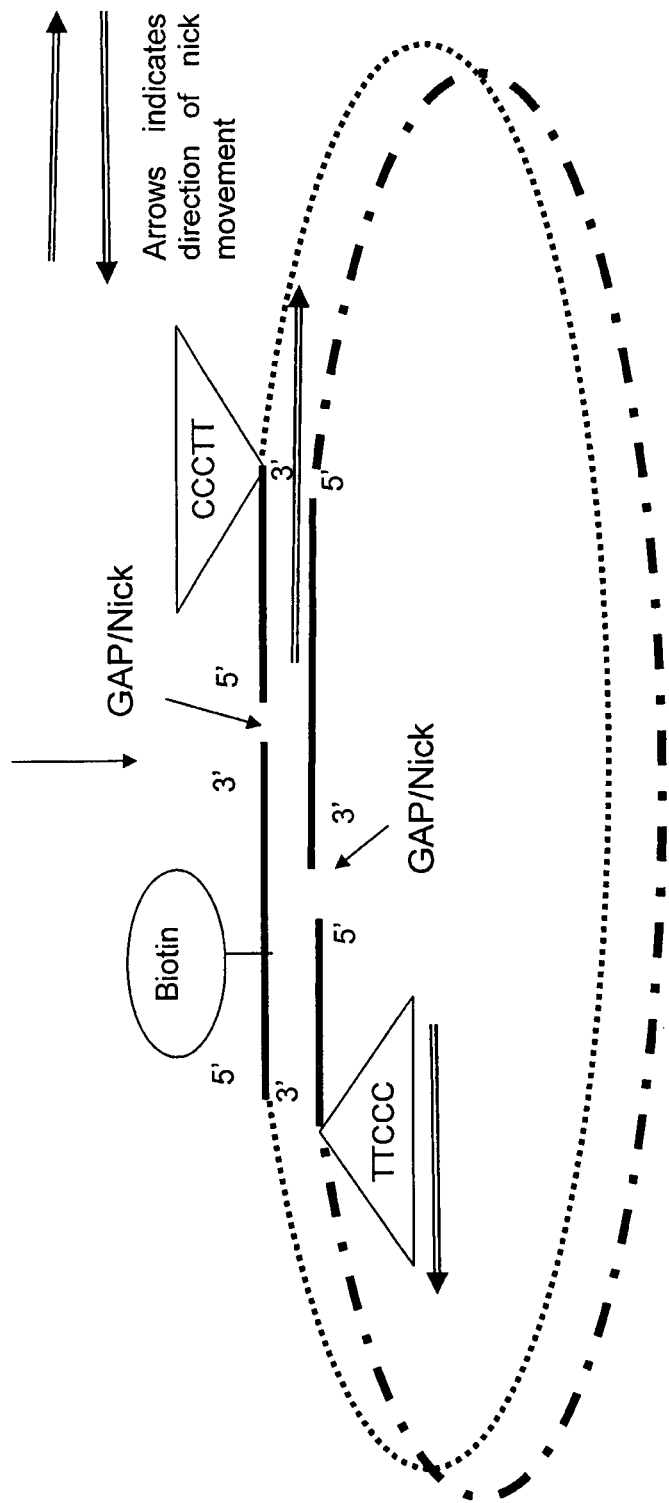
FIG. 13 depicts an embodiment of a nicked circular nucleic acid molecule.

Another embodiment is depicted in FIG. 10, FIG. 11, FIG. 12 and FIG. 13. In this embodiment, adaptors having a Topoisomerase I (Topo) binding site CCCTT can be employed (Topo binding adaptors). In a first step, one can form an adaptor having 2-3 bp Gaps on opposite strands and Topo binding sites at the 3' end of both the top and bottom strands (FIG. 10). Following this, one can add Topoisomerase I to form a Topoisomerase I-adaptor complex (FIG. 11). The phosphotyrosil bond formed between the Topoisomerase 1 molecules and the adaptor can be subsequently attacked by the 5' hydroxyl group of a dephosphorylated double stranded polynucleotide of interest (FIG. 12), resulting in the formation of circularized nucleic acid molecules (FIG. 13). Following circularization the nicks at the junction of adaptors and DNA are sealed with T4ligase. In such an embodiment, the use of a topoisomerase I based circularization approach can provide superior circularization efficiency for long paired-tag creation.

Figure 6:
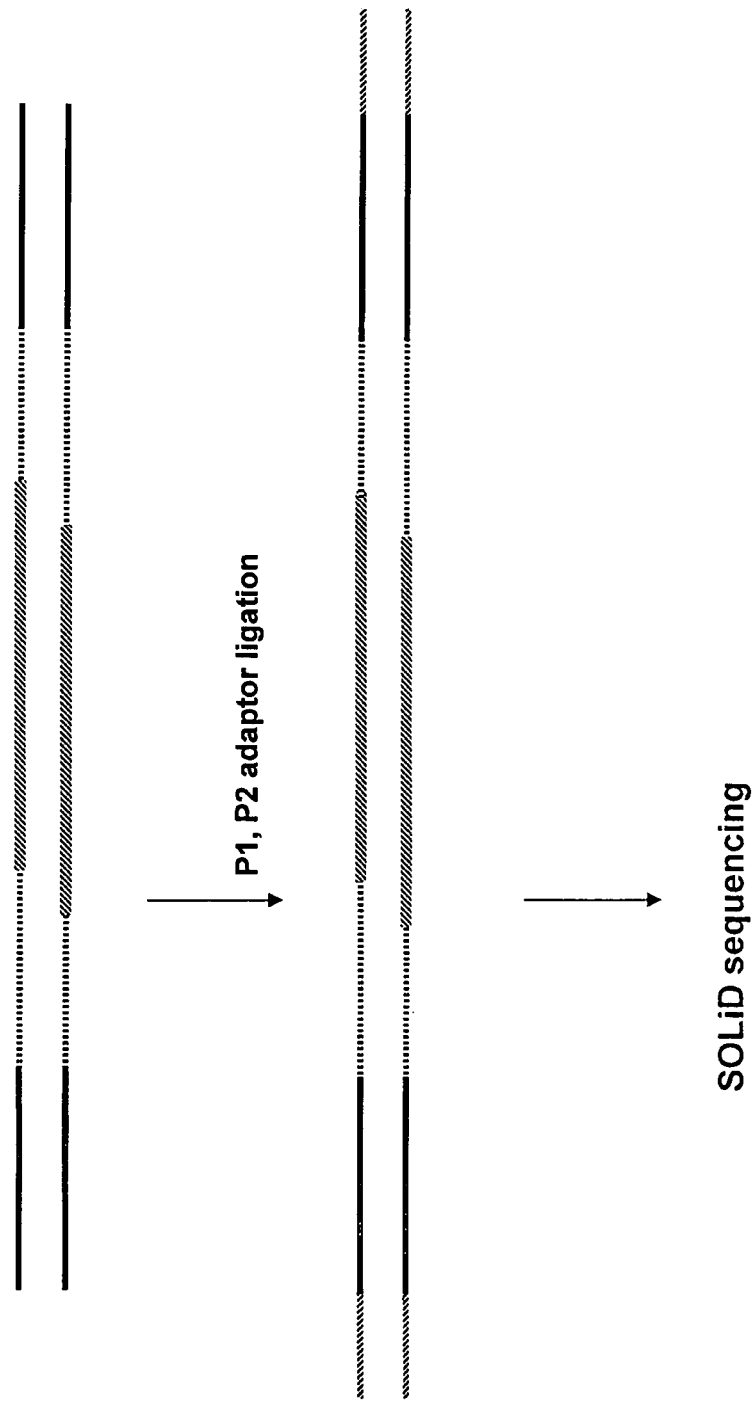
FIG. 6 depicts an embodiment for attaching primer adaptors to a paired tag for sequencing.

In some embodiments, further primers can be added to the paired tag, such as P1 and P2 primer adaptors, as shown in FIG. 6. In such an embodiment, the addition of the P1 and P2 primer adaptors can be useful for various sequencing techniques, such as, for example, SOLiD™ type sequencing.

Figure 15:
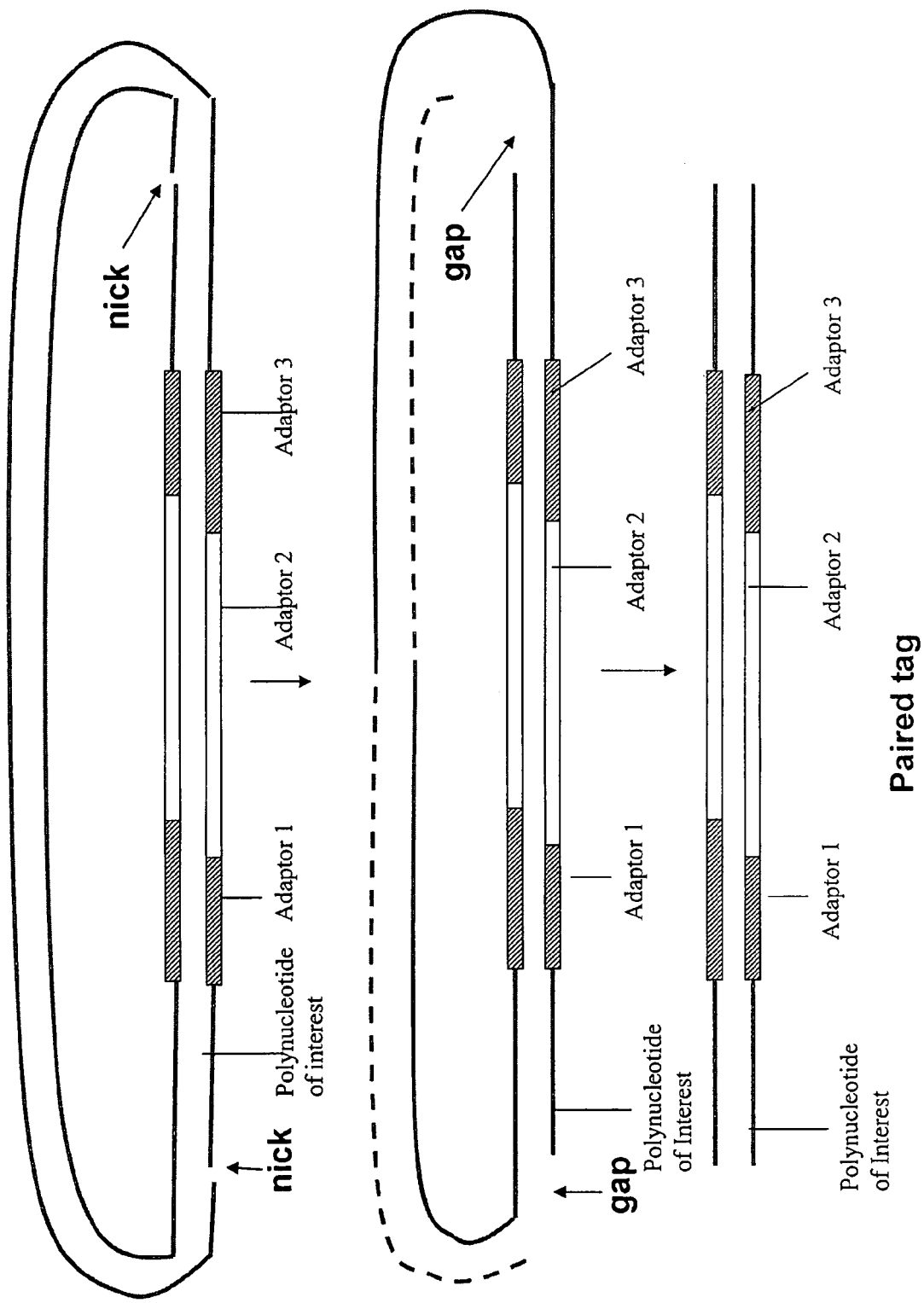
FIG. 15 depicts some embodiments for forming paired tags by gap formation.

In some embodiments, the polynucleotides of interest can be circularized by ligating the polynucleotides of interest to one or more adaptors (for example, as shown in FIG. 3). The resulting nicked circular DNA can be nick translated (FIG. 14). The nicked circular DNA can be digested with exonucleases, such as, for example, T7 exonuclease, lambda exonuclease, and/or *E coli* exonuclease III (FIG. 15). The nicks are thus opened and become gaps that are relatively more readily digested by single strand specific endonucleases. Following this, the paired tag can be released from the gapped double stranded polynucleotide of interest by using a single strand specific endonuclease (such as a S1 nuclease). Such single strand specific endonucleases include, for example, S1 nuclease, mung bean nuclease, P1 nuclease, and/or BAL31 nuclease. The T7 exonuclease reaction can either be partial (shown as the "gap" in the middle panel) or complete (depicted in the middle panel by the dashed sections which are absent when there is a complete exonuclease reaction).

Figure 16:
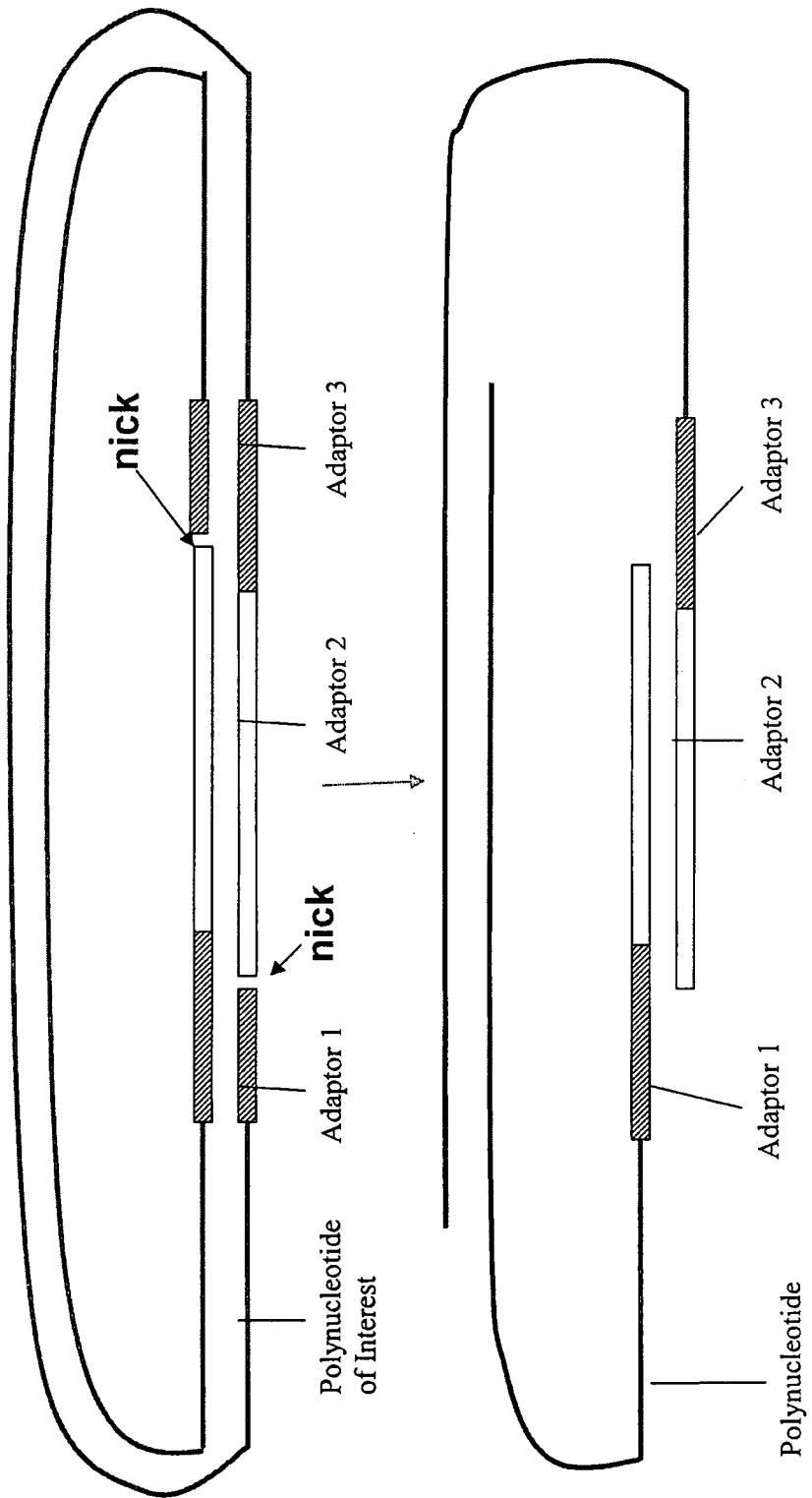
FIG. 16 depicts an alternative embodiment for forming paired tags.
Figure 18:
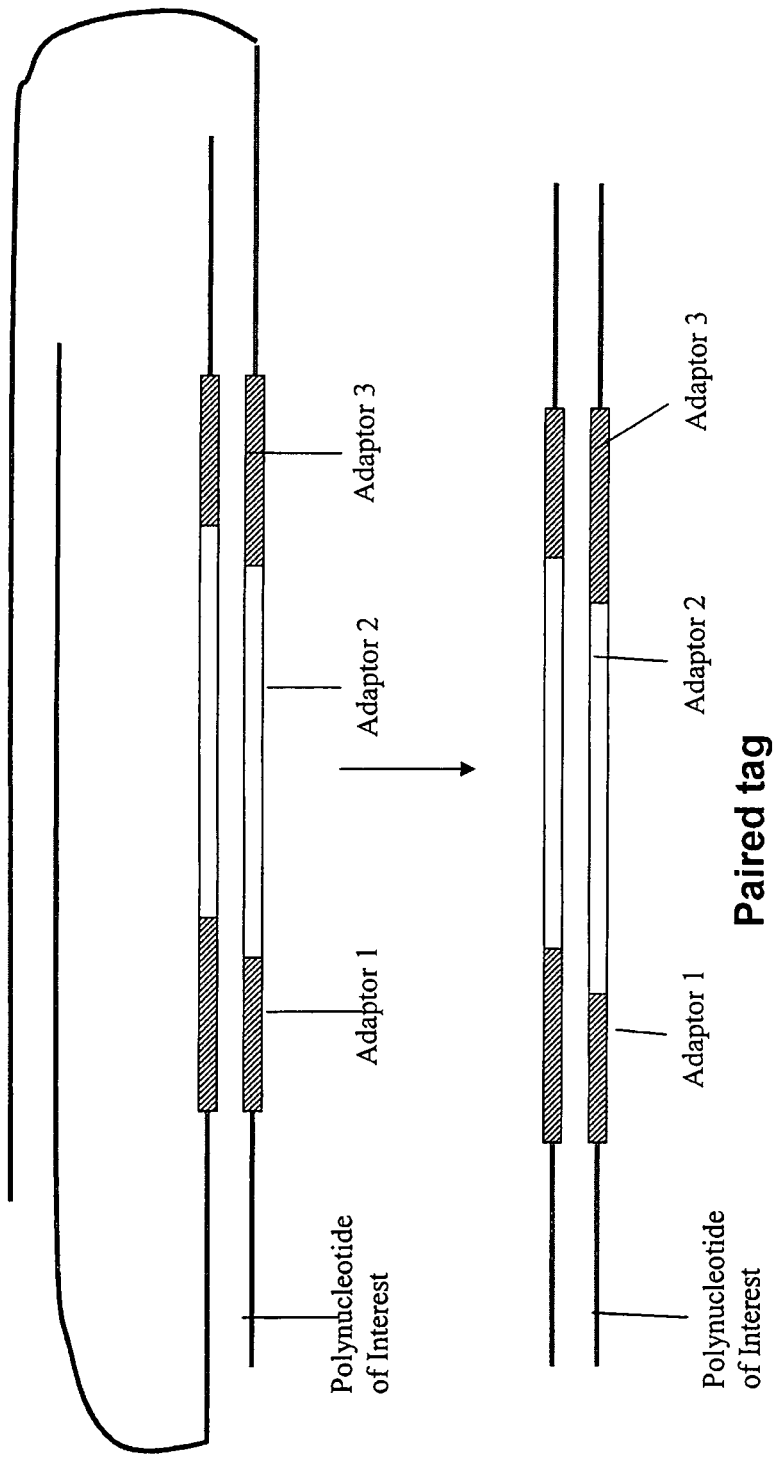
FIG. 18 depicts an alternative embodiment for forming paired tags continued from FIG. 17.

In some embodiments, nick translation need not actually occur, but rather the extension of the 3' end of the adaptor can be used to create a paired tag. An example of this is shown in FIGS. 16-18. In some embodiments, the polynucleotide of interest can be circularized by ligation to one or more adaptors. In some embodiments, the circular nucleic acid will include a nick. The circular nucleic acid molecule can then be digested with 5' to 3' exonuclease, such as T7 exonuclease and/or lambda exonuclease (FIG. 16). The resulting digested circular nucleic acid molecule can then have its 3' ends extended with, for example, a DNA polymerase (FIG. 17). Any DNA polymerase can work for this purpose. Effectively, this step can allow for the sequence with the adaptor to be extended into the polynucleotide of interest. Following this, the extended digested circular nucleic acid molecule can be digested with single strand specific endonucleases to release the paired tag. As above, any single strand specific enzyme and/or cleaving process can be used, such as S1 nuclease, mung bean nuclease, P1 nuclease, and/or BAL 31 nuclease to release the paired DNA tags.

Figure 19:
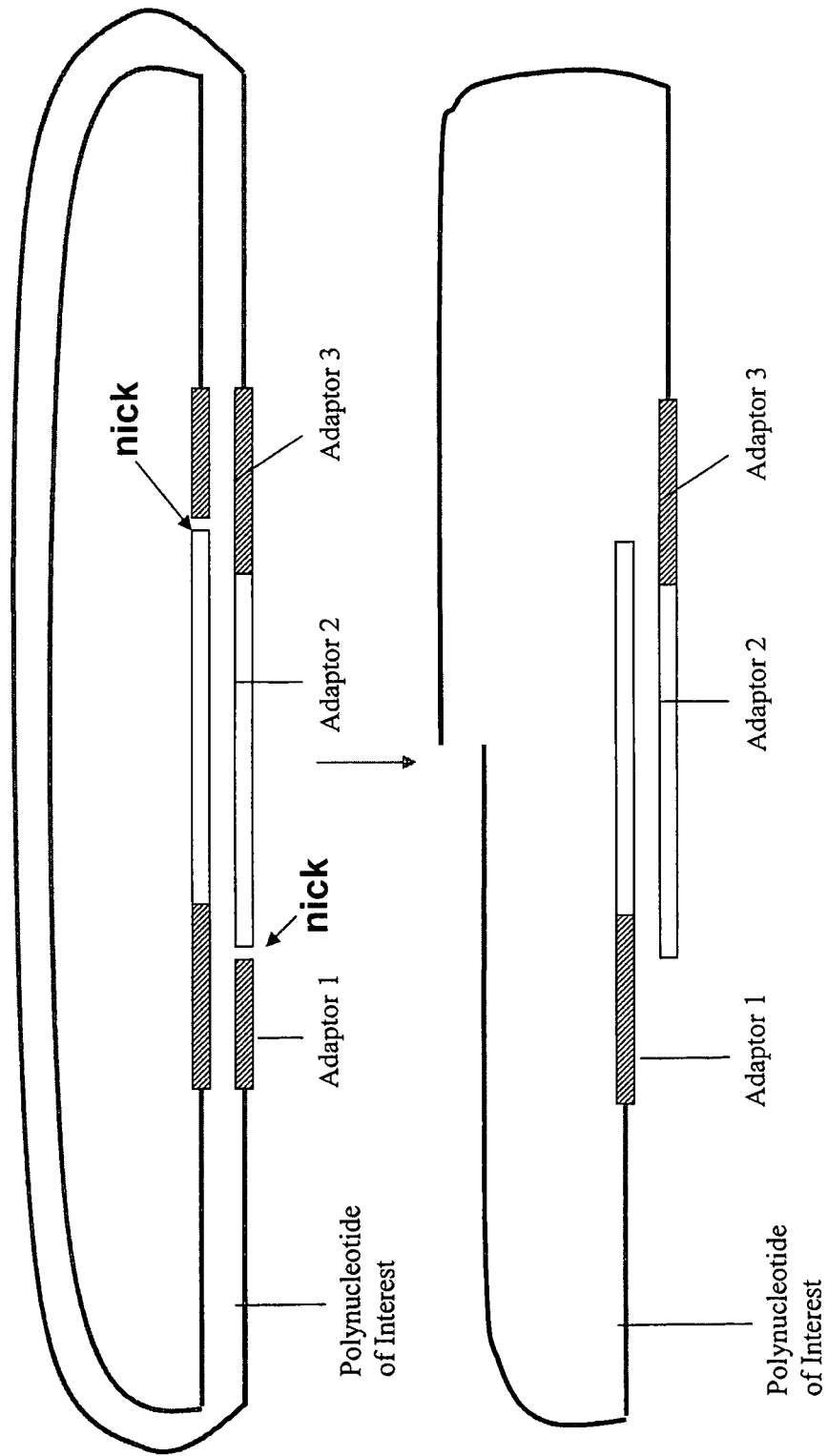
FIG. 19 depicts an alternative embodiment for forming paired tags.
Figure 21:
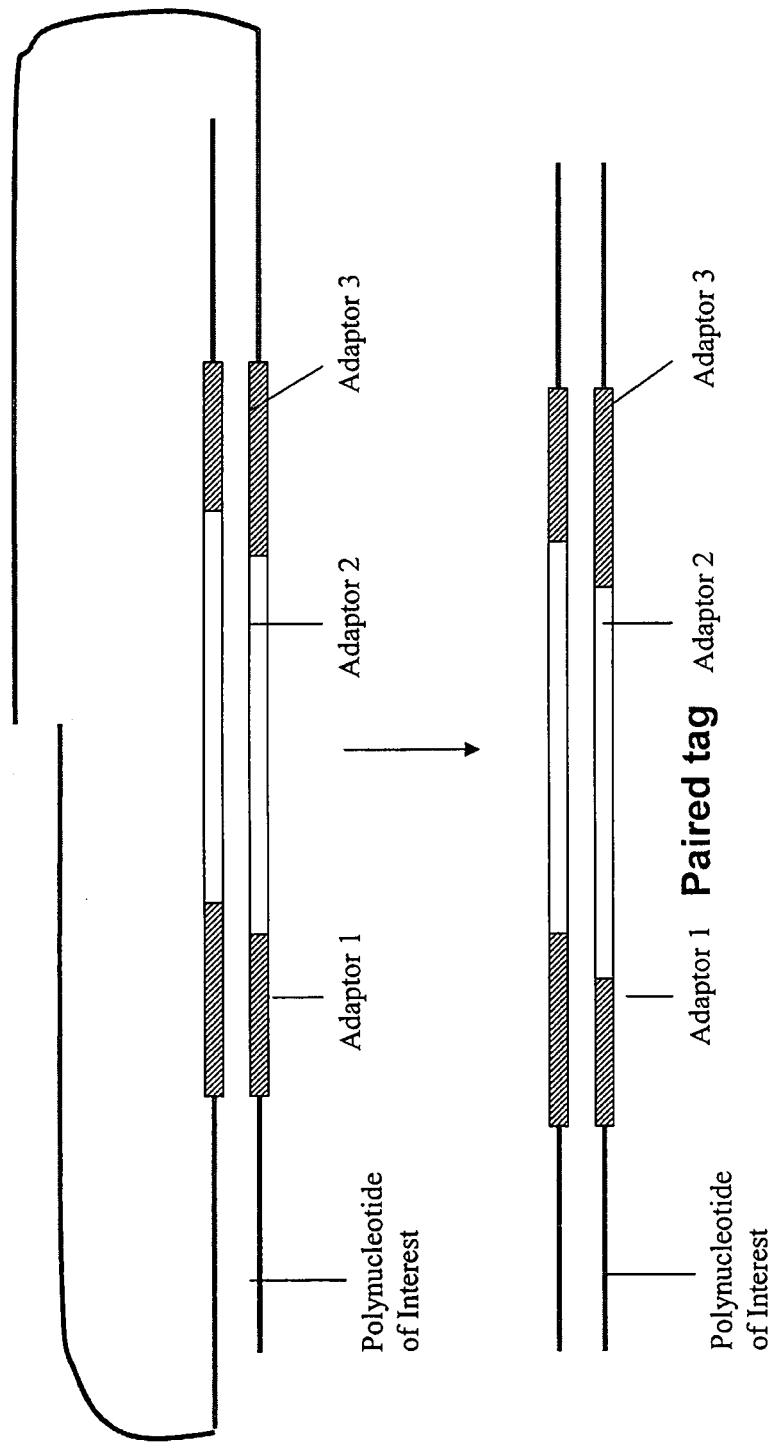
FIG. 21 depicts an alternative embodiment for forming paired tags continued from FIG. 20.

FIGS. 19-21 depict another embodiment in which a paired tag is formed without the need for nick translation per se. As above, in some embodiments, the polynucleotide of interest can be circularized by ligation to one or more adaptors. In some embodiments, the circular nucleic acid molecule will include a nick. The circular nucleic acid molecule can then be digested with a 5' to 3' exonuclease, such as T7 exonuclease and/or lambda exonuclease (FIG. 19). In some embodiments, the digest is allowed to remove a large amount of the double stranded section of the polynucleotide of interest. While the example outlined in FIGS. 16-18 demonstrate that the digest can be partial, as shown in FIG. 19, the digest can also be allowed to occur to completion. As will be appreciated by one of skill in the art, as this results in making the entire polynucleotide of interest single stranded. Thus, in some embodiments, all of the polynucleotide of interest is single stranded following the 5' to 3' digest. In some embodiments, this will result in the digested "circular" nucleic acid becoming linearized; however, for simplicity, the molecule can still be referred to as a "digested circular nucleic acid molecule," even though it is linear. When the linear nature of such an embodiment is specifically described, it will be referred to as a "digested circular nucleic acid molecule that has been digested to a linear state." As above, the resulting digested circular nucleic acid molecule can then have its 3' ends extended with, for example, a DNA polymerase (FIG. 20). Following this, the extended digested circular nucleic acid molecule can be digested with a single strand specific exonuclease and/or endonuclease to release the paired tag. As above, any single strand specific enzyme and/or cleaving process can be used. By digesting the circular nucleic acid to the state shown in FIG. 20, one can employ an exonuclease to remove any remaining parts of the single stranded polynucleotide of interest. Of course, an endonuclease can still be employed as well. As will be appreciated by one of skill in the art, while the above techniques have been described with regard to the initial embodiment in FIG. 3, the embodiments in FIGS. 14-20 are not limited to such a starting arrangement and can be used in combination with any of the other embodiments described herein, as appropriate.

While some embodiments employ a nick between the adaptor and the polynucleotide of interest, the nick and/or gap need not be located at this position. In some embodiments, there are further advantages to locating the nick and/or gap elsewhere. In some embodiments, the method can employ a linking polynucleotide that already includes a nick. In some embodiments, the linking polynucleotide will have an adaptor on each end of the linking polynucleotide with a nick between each adaptor and the linking polynucleotide. This can allow the incorporation of the nicks with a polynucleotide of interest via the initial construct itself. For the sake of simplicity, this construct can be referred to as a "nicked vector" or "nicked linking polynucleotide." In some embodiments, the nicked linking polynucleotide can reduce the time and steps involved in current paired tag workflow. In some embodiments, the nicked linking polynucleotide includes a linearized vector to capture the polynucleotide of interest (such as a sheared target DNA) and simplifies the construction of a library of polynucleotides of interest.

In some embodiments, methods involving the nicked polynucleotide of interest include two parts. The first part can involve the preparation of a nicked linking polynucleotide with appropriate adaptors linked to it. In some embodiments, this step can be performed by various parties and can be included in a kit for making paired tags. In some embodiments, the second part involves the use the nicked linking polynucleotide to increase library workflow.

Linking Polynucleotide

In some embodiments, the first step (FIG. 22, Step 1) involves the selection of a small circular DNA 2000 as a linking polynucleotide for the polynucleotide of interest. Once linearized, this can be employed as the linking polynucleotide. Since there need be no bacterial transformation and/or amplification involved, the choice of the vector is flexible. In some embodiments, any polynucleotide can be used. Thus, the linking polynucleotide need not be a vector per se or derived from a vector. In some embodiments, the linking polynucleotide can be any circular vector that can be prepared and linearized. In some embodiments, a pUC19 plasmid is used.

In some embodiments, there are two relevant elements that can be considered in selecting a vector that can serve as a linking polynucleotide. First, in some embodiments, the size of the circular vector should be small, preferable in the 400 bp to 3 kb range, in order to accommodate target DNA inserts from 200 bp up to 15 kb. Second, while not required, in some embodiments, the circular vector can be modified with a binding moiety for subsequent purification. For example, in some embodiments, the binding moiety can include biotin, thereby allowing for a biotin-Streptavidin based purification scheme. In some embodiments, any receptor-ligand based affinity modification that allows isolation of paired tags can be used. In some embodiments, the isolation is specific to a specific linking polynucleotide.

Figure 22:
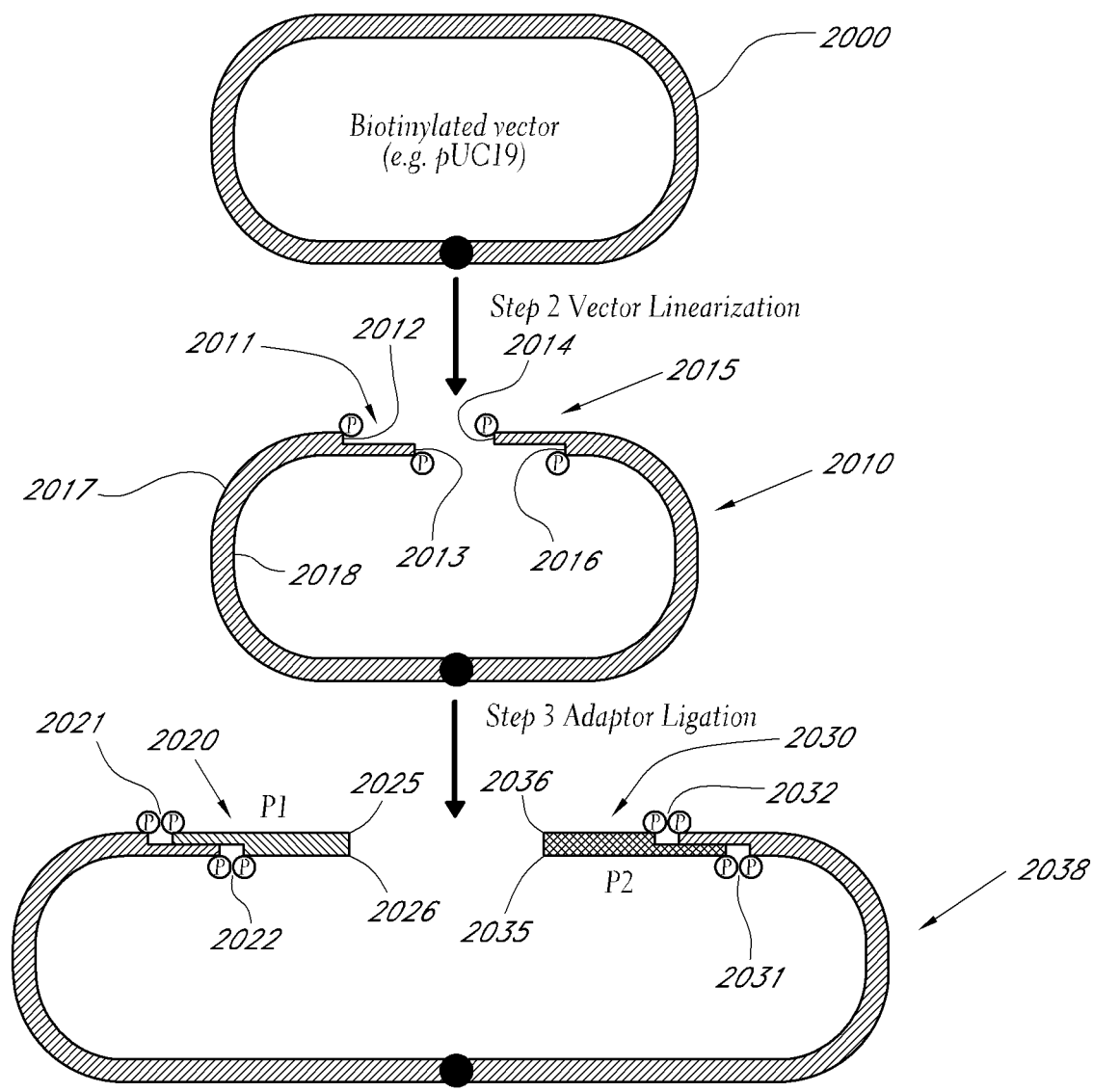
FIG. 22 depicts an embodiment of a nicked linking polynucleotide.

After the linking polynucleotide is selected, if need be, it is linearized 2010 (e.g. if a circularized vector is initially selected). In some embodiments, this is achieved with two unique restriction enzymes (FIG. 22, Step 2), each of which makes a unique cut on the linking polynucleotide. The larger fragment 2010 of the resulting two fragments contains two distinct sticky ends (2011 and 2015) and can be selected and purified. By using two different enzymes, the resulting product contains incompatible sticky ends (2011 and 2015) that prevent self-ligation. Other techniques that generate non-compatible ends on a linking polynucleotide can also be effective for this step. As shown in FIG. 22, the double cut linking polynucleotide's two ends (2011 and 2015) will have two 3' strand ends (2012 and 2016, that lack phosphates, and two 5' strand ends 2013 and 2014, that contain phosphate groups.

Following this, two double stranded adaptors, P1 (2020) and P2 (2030), are hybridized to the linking polynucleotide 2010 to form an adaptor hybridized linking polynucleotide 2038. In some embodiments, the sticky ends of P1 (2020) and P2 (2030) match their respective ends on the linking polynucleotide (2011 and 2015), ensuring the proper orientation and position of the P1 (2020) and P2 (2030).

Figure 23:
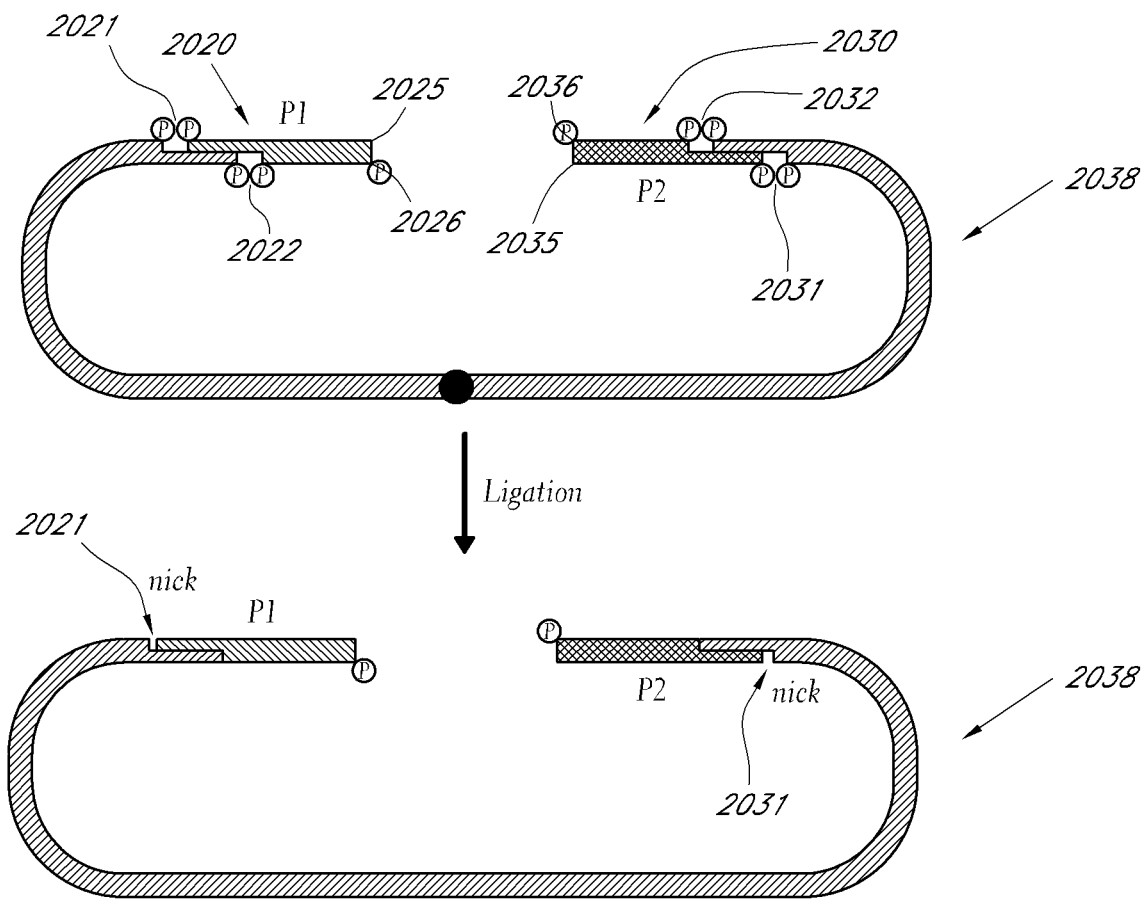
FIG. 23 depicts an embodiment of a nicked linking polynucleotide where the adaptors are ligated onto a linking polynucleotide.

In some embodiments, the P1 and P2 primer adaptors contain distinct features. In some embodiments, the "top" strands of the P1 primer adaptor 2025 (shown as the upper of the two P1 strands in FIG. 22) and P2 primer adaptor 2035 (shown as the lower of the two strands in FIG. 22) contain no phosphate groups at their 5'-end. In some embodiments, the bottom strands of both P1 and P2 primer adaptors (2026 and 2036 respectively) do contain a phosphate group at their 5' end (as shown in position 2022 and 2032). As a result of this configuration, only the "bottom" strands (2026 and 2036) of both adaptors are ligated to the linking polynucleotide, as shown in the nicked linking polynucleotide 2039 (FIG. 23). Because of the lack of the phosphate group at 5'-ends of the "top" strands, there will be two nicks 2021 and 2031 between the linking polynucleotide 2010 and the adaptors 2020 and 2030 (FIGS. 22 and 23). Thus, in some embodiments, the invention comprises a method of making and/or using the above linking polynucleotide.

In some embodiments, the invention comprises the nicked linking polynucleotide itself. In some embodiments, the nicked linking polynucleotide 2039 can a first adaptor (P1 2020) comprising a first adaptor strand 2025 that is hybridized to a second adaptor strand 2026. The first adaptor strand 2025 lacks a phosphate group on its 5' end. The nicked linking polynucleotide can further comprise a second adaptor 2030 comprising a third adaptor strand 2035 that is hybridized to a fourth adaptor strand 2036. The third adaptor strand 2035 lacks a phosphate group on its 5' end. The nicked linking polynucleotide can further comprise a linking polynucleotide 2010 that comprises a first linking strand 2017 hybridized to a second linking strand 2018. The linking polynucleotide comprises a first end 2011 and a second end 2015. The first adaptor (P1 2020) is attached to the first end 2011 of the linking polynucleotide 2010 such that a nick (and/or gap) 2021 is present where the first adaptor strand lacks a phosphate group on its 5' end. In addition, the second linking strand 2018 is attached to the second adaptor strand 2026. The second adaptor (P2 2030) is attached to the second end of the linking polynucleotide 2015 such that a nick (and/or gap) 2031 is present where the third adaptor strand 2035 of the second adaptor 2030 lacks a phosphate group on its 5' end. The first linking strand 2017 is attached to the fourth adaptor strand 2036. This embodiment is generally depicted in FIGS. 22 and 23 (in which the adaptors 2020 and 2030 have been ligated to the linking polynucleotide 2010 to form a nicked linking polynucleotide or nicked vector 2039).

Figure 24A:
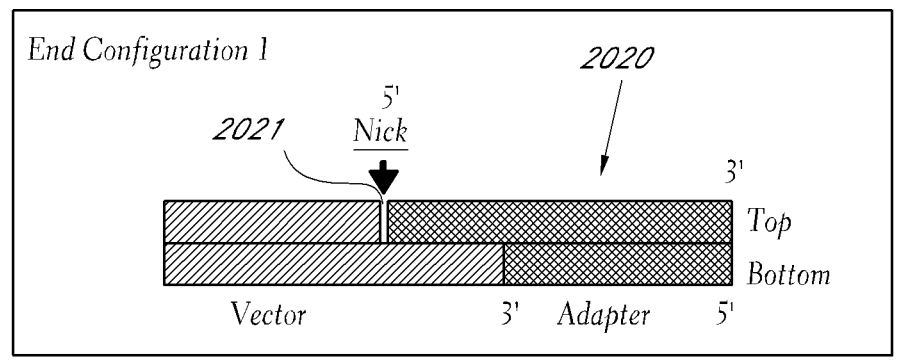
FIG. 24A depict an embodiments for the nick configurations between the adaptor and the linking polynucleotide.
Figure 24B:
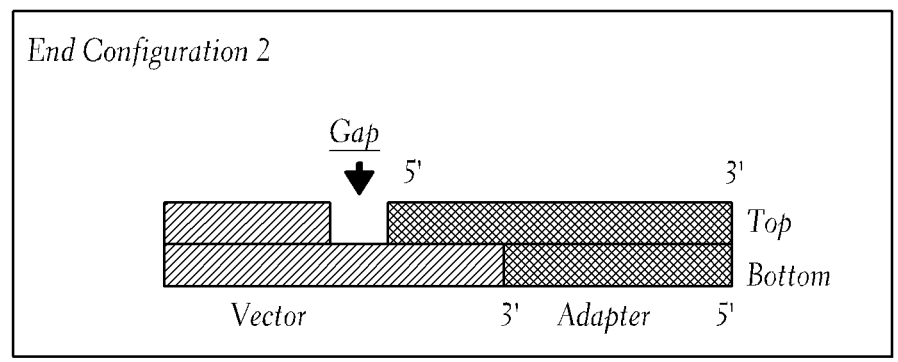
FIG. 24B depict an embodiments for the nick configurations between the adaptor and the linking polynucleotide.

In some embodiments, there are at least two possible arrangements for the regions where the adaptor is joined with the linking polynucleotide (the "joint region"), as shown in FIGS. 24A and 24B. In the first configuration (FIG. 24A), the overhang of the linking polynucleotide has a complete complementary end for the adaptor 2020. As a result of ligation and the lack of phosphate group of the top adaptor strand, there is a nick 2021 between the linking polynucleotide and the adaptor on the top strand. In the second configuration (FIG. 24B), the setup of the adaptors results in a one- or two-base gap (and in some embodiments a larger gap). Either configuration can work for the subsequent steps in the process. One should generally preserve the breakage on the top strand (the nick 2021 between 2020 and 2017 and the nick 2031 between 2035 and 2018) in order to allow a polymerase to extend the nick or gap into the polynucleotide of interest.

In some embodiments, the setup of the nick or gap in the nicked linking polynucleotide can be used to generate especially long paired tags, or "Long Paired Tags" ("LPT") libraries. However, the current invention is not limited to LPTs. For example, for typical EcoP15I based regular PT libraries, one can ligate both strands of the adaptors with EcoP15I sites completely to the linear vector without any of the aforementioned end configurations. In short, the above embodiment can generate both regular and long paired tag libraries with appropriate chemistries and properly modified adaptors for different paired tags.

Figure 25A:
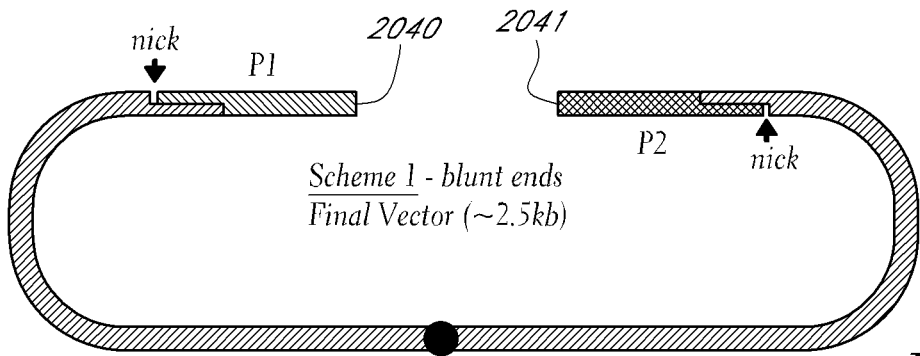
FIGS. 25A-25C depict three embodiments for various configurations of the adaptor ends.
Figure 25B:
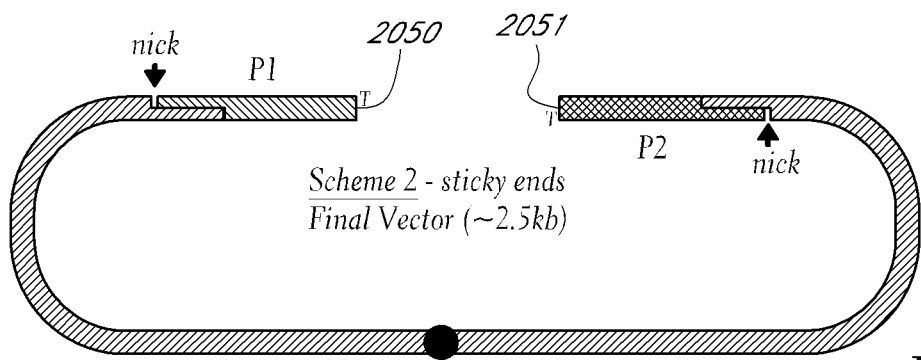
Figure 25C:
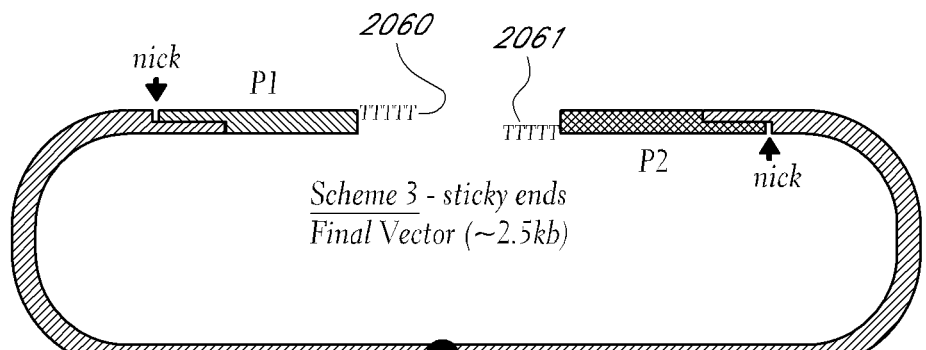

In some embodiments, there are additional possible configurations of adaptor ends (2020 and 2030) on the linking polynucleotide for capturing polynucleotides of interest, examples of which are shown in FIGS. 25A-25C. By adjusting the length and composition of the 5'-end of the top strand of the adaptors, one can have either a blunt end (2040 and 2041, FIG. 25A), a single thymine overhang sticky end (2050 and 2051, FIG. 25B), or a multiple thymine (or other base) overhang (2060 and 2061, FIG. 25C). Such nicked linking polynucleotides can be employed to capture blunt ended polynucleotides of interest, Taq polymerase modified polynucleotides of interest, or Terminal Transferase modified polynucleotides of interest, respectively. In some embodiments, these nicked linking polynucleotides are part of a kit for use in the construction of a library.

Library Preparation Workflow

Once the nicked linking polynucleotides are prepared, polynucleotides of interest, such as genomic DNA, can be sheared to a desired length. In some embodiments, the polynucleotides of interest are end-polished for appropriate use in a Support Oligo Ligation Detection (SOLiD™) based technique. Depending upon the choice of a nicked linking polynucleotide (as shown in FIGS. 25A-25C) for ligating with a polynucleotide of interest, sheared polynucleotides of interest can involve modification at the ends. For the linear vector with blunt end adaptors (FIG. 25A), no modification is necessary. For the nicked linking polynucleotide described in FIG. 25B, the polynucleotides of interest require the addition of an adenine base at the 3'-ends, which can be achieved, for example, by a polymerase such as Taq. For the nicked linking polynucleotide described in FIG. 25C, a terminal transferase can be used to add a short stretch of the same base so that it is complementary to the overhang in the nicked linking polynucleotide.

Figure 26:
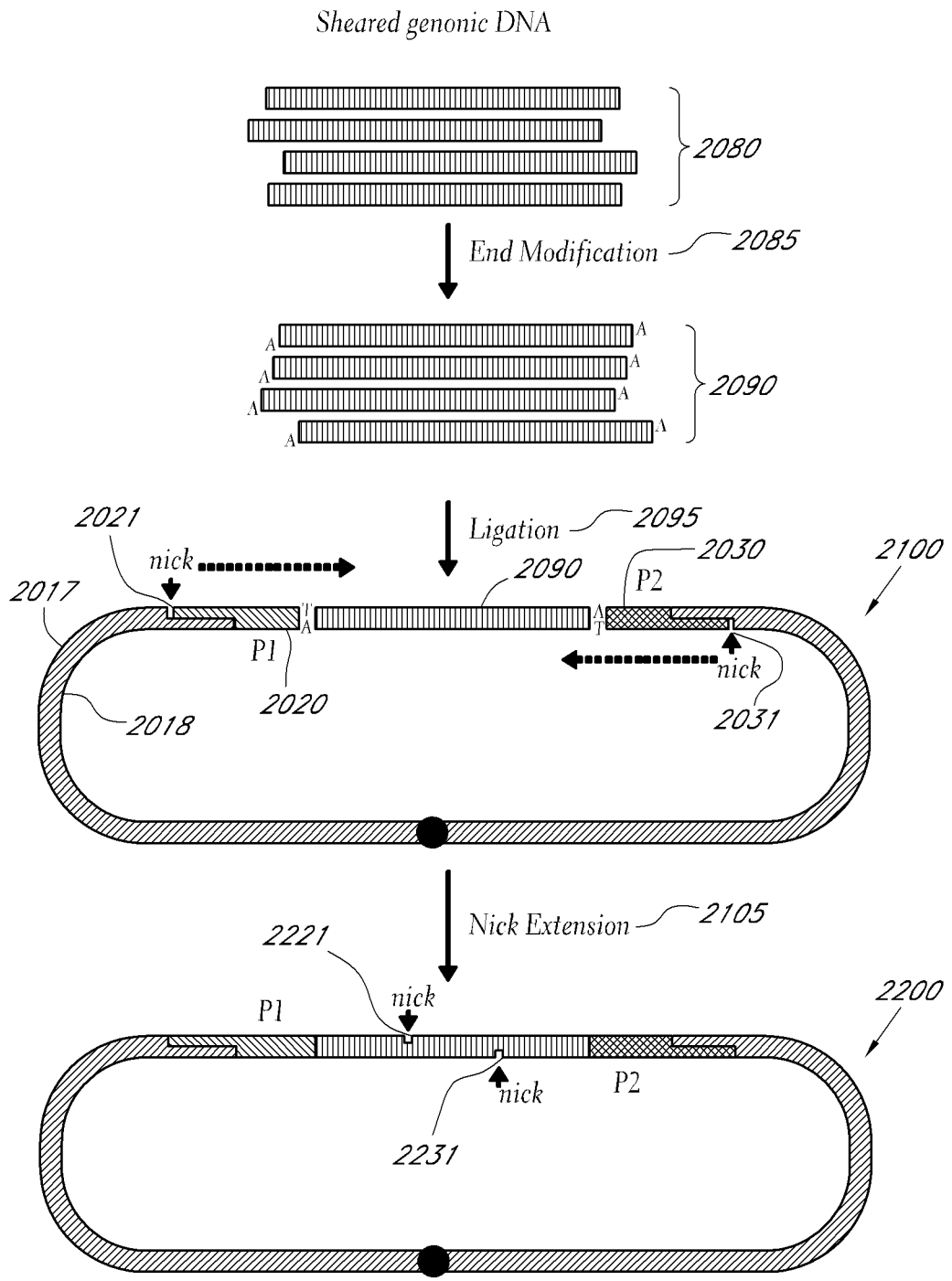
FIG. 26 depicts an embodiment of a method employing the nicked linking polynucleotide in FIG. 25B.

Once a nicked linking polynucleotide is selected, subsequent steps of the work flow can be similar for all three types of nicked linking polynucleotides. For the sake of simplicity, the subsequent steps are generally described only with regard to the nicked linking polynucleotide in FIG. 25A. As shown in FIG. 26, after the appropriate end modification 2085 of the polynucleotides of interest, the polynucleotides of interest are incubated with the nicked linking polynucleotide with the matching overhang for the ligation 2095.

After the ligation 2095, the circularized nicked linking polynucleotides (e.g. a circularized nucleic acid molecule) contains the two nicks (2021 and 2031) located close to the polynucleotide of interest 2090, as shown in structure 2100. Both nicks 2021 and 2031 are then extended into the polynucleotide of interest 2090 by process 2105. As noted above, this can occur via nick translation or any of the other noted embodiments for extending the 3' ends of the first and second linking polynucleotides 2017 and 2018 into the polynucleotide of interest 2090. In some embodiments, the extension is achieved by nick translation. In some embodiments, the degree of extension can be controlled so that the final break points (located at the nicks or where the molecule is single stranded) remain consistent.

In some embodiments, after the ligation reaction 2095, the un-ligated linear polynucleotide of interest and the remaining linear nicked linking polynucleotides can be eliminated or removed. In some embodiments, this is achieved by an enzyme that digests linear double stranded DNA, such as in a PLASMID-SAFE ATP-Dependent DNase kit (available from Epicentre).

In some embodiments, following the cleaning process noted above, the remaining circular species 2100 can then be cut at the new position of the extended 3' ends by process 2205 to release the paired tag. In embodiments in which the 3' ends are moved via nick translation, the cut sites will be at the new nick positions 2221 and 2231. The resulting released paired tag 2300, can include the linking polynucleotide 2010, the two adaptors 2020 and 2030, and can be flanked by polynucleotides of interest tags 2091 and 2092 of desired length (FIG. 27).

Figure 27:
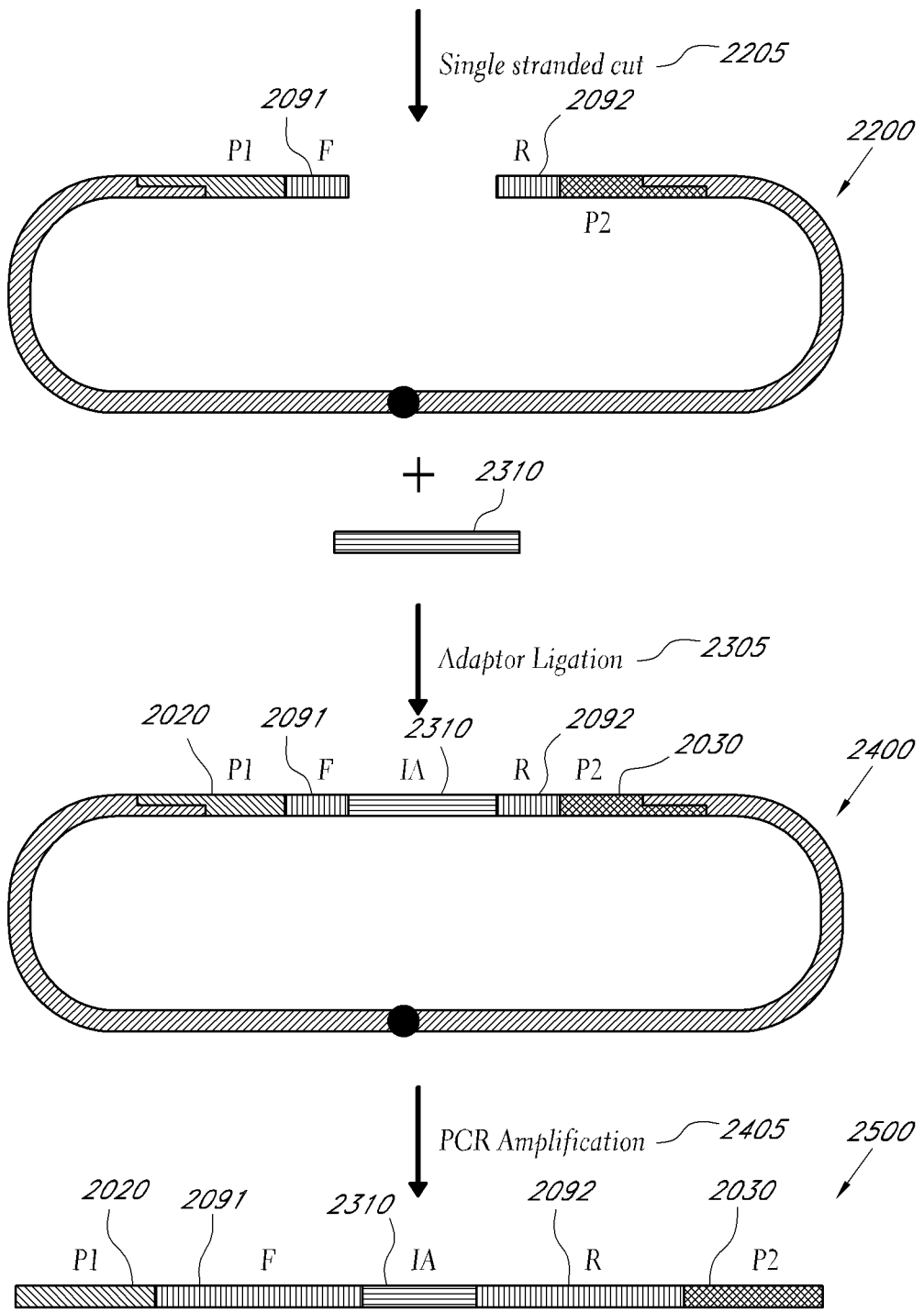
FIG. 27 depicts the continuation of the embodiment in FIG. 26.

In some embodiments, a SOLiD™ internal adaptor 2310 can be ligated to the released paired tag 2300 that is produced (as shown in FIG. 27) in process 2305 to create an internal adaptor containing paired tag 2400. After the ligation, the resulting internal adaptor containing paired tag 2400 (or population thereof) can become the library template with both polynucleotides of interest tags 2091 and 2092 properly oriented. In some embodiments, the library can serve as template for a large-scale PCR amplification using primers that can bind to one strand of the adaptors P1 2020 and P2 2030, as generally depicted in process 2405 in FIG. 27 (primers not depicted). The resulting PCR product 2500 can be single stranded and have P1 and P2 sequences located on each end of the product. In some embodiments, the primer sequences for the PCR amplification 2405 are those used in a SOLiD™ library. In some embodiments, when the resulting amplified linear product is a library, the library can then be used in an emulsion PCR for templated bead preparation.

Figure 28:
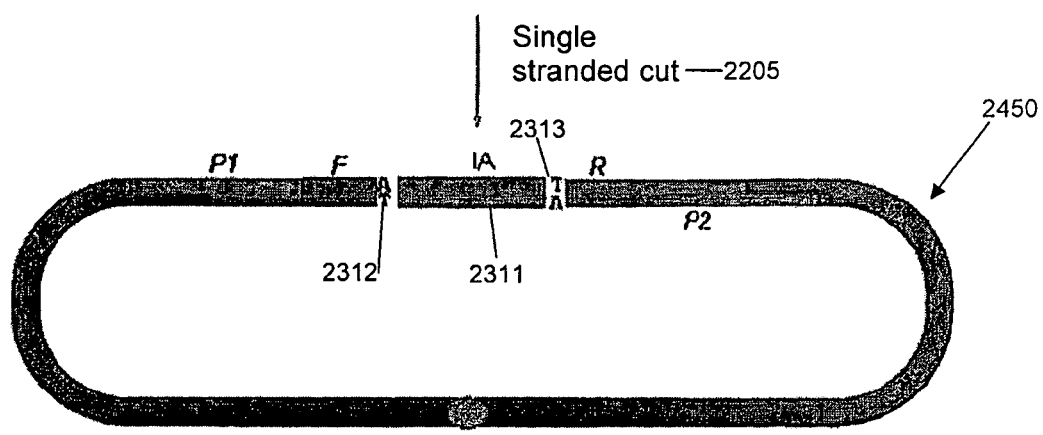
FIG. 28 depicts an alternative embodiment of an internal adaptor ligation.

While FIG. 27 depicts a blunt end internal adaptor 2310, in some embodiments, the ends of the released paired tag 2300 can be modified to prevent or reduce self-ligation, as shown in FIG. 28. For example, Taq polymerase can be employed to append an adenine base at the 3'-ends after the single stranded cut 2205 so that the resulting released paired tag can only be ligated to an internal adaptor 2311 that comprises a T overhand at its 5'-ends (FIG. 28).

While there are a number of different advantages for the above noted embodiments, in some embodiments, the use of a nicked linking polynucleotide can avoid or reduce the number of steps required in various paired tag library workflows. For example, some current SOLiD™ paired tag library workflows entail fourteen significant steps in creating libraries appropriate for sequencing on a SOLiD™ Analyzer. In some embodiments, the use of the nicked linking polynucleotide allows one to remove one or more steps from preparing a paired tag library workflow. In some situations, a typical workflow can include the following processes: 1) shearing DNA, 2) end repair of DNA, 3) methylating the gDNA at EcoP15I sites, 4) ligating in an adaptor, 5) size fractionation, 6) circularize via an internal adaptor, 7) Eco P15I digestion, 8) end repair, 9) adaptor ligation, 10) binding moiety binding, 11) nick translation, 12) large scale PCR, 13) gel purification and size selection, and 14) final quantitation of library. In some embodiments, by using one or more of the embodiments described herein, processes 4-6 can be compressed to simply ligating in a nicked linking polynucleotide. In addition, one or more of processes 9-11 can also be removed. Thus, in some embodiments one or more of processes 4-6 and 9-11 are removed and/or exchanged for one of the embodiments described herein. In some embodiments, a standard workflow can include the following processes: 1) shearing DNA, 2) end-repairing the DNA, 3) methylating the gDNA at EcoP15I sites, 4) ligating in an adaptor (e.g. CAP adaptors), 5) size selection, 6) DNA circularization via an internal adaptor, 7) Plasmid-safe™ DNase treatment, 8) Eco P15I digestion, 9) Klenow-mediated end-repair, 10) adaptor ligation, 11) binding moiety binding, 12) nick translation, 13) large scale PCR (e.g. library amplification), and 14) gel purification and size selection and quantitation of library. However, by using one or more of the embodiments disclosed herein, the workflow can simply include the following processes: 1) shearing DNA, 2) size select, 3) end-repair, 4) methylation of genomic EcoP15I sites, 5) LVA ligation, 6) PLASMID-SAFE™ DNase Treatment, 7) EcoP15I digestion, 8) end repair, 9) internal adaptor ligation, 10) library amplification, and 11) library purity QC & quantitation. Thus, in some embodiments, the workflow can be reduced to 11 processes from 14. Of course, the advantages disclosed herein are not limited to sequencing on a SOLiD™ system.

Some other paired tag libraries take approximately four days to construct, creating a bottleneck for SOLiD™ related workflow. In some embodiments, the time required to make a paired tag library by using a nicked linking polynucleotide is less than 4 days, for example, 3 days, 2 days, 1 day, less than 20 hours, less than 15 hours, or 10 hours. In addition, multiple steps increase the chance of experimental errors, and the loss of samples during each of those steps. The use of the nicked linking polynucleotide can expedite the workflow while improving sample recovery. In some embodiments, nicked linking polynucleotide based workflow method reduces the number of steps in the paired tag library workflow to six steps, and/or reduces the time required for the entire procedure to approximately 10 to 12 hours. In some embodiments, the experimental procedures are reduced from fourteen steps to less than 13, less than 12, less than 11, less than 10, less than 9, less than 8, less than 7, or 6 steps.

Figure 29A:
FIG. 29A depicts how some of the embodiments of the nicked linking polynucleotides result in all of the nicked linking polynucleotides being useful.
Figure 29B:
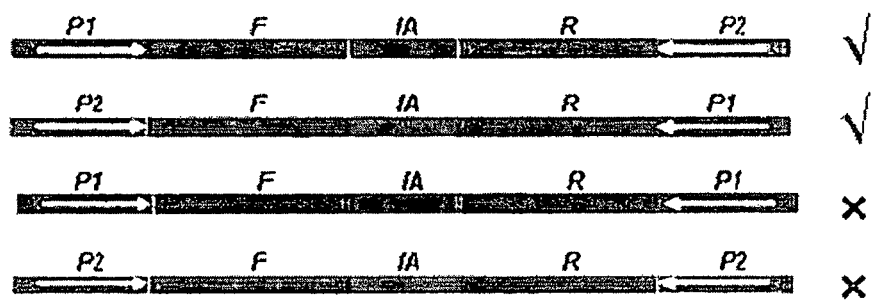
FIG. 29B depicts the numerous possible arrangements of less preferred nicked linking polynucleotides and how some of them result in less useful products.

In some embodiments, in contrast to other PT schemes, where 50% of the target DNA fragments ligated to adaptors are futile products, all of the target fragments ligated to linear vector would be productive for subsequently processing (see, e.g. FIG. 29A vs. FIG. 29B). While in the some PT methods, the circularization process with the internal adaptor can suffer significant sample loss due to the poor self-circularization efficiency, in some of the disclosed embodiments, polynucleotides of interest are already linked to the linking polynucleotide with the proper length, and are therefore already captured. Thus, more internal adaptor can be used to drive the maximal ligation efficiency in some embodiments. Furthermore, with the T/A overhang (e.g., FIG. 28), the self-ligation of linking polynucleotide and adaptor can be reduced.

In some embodiments, the nicked linking polynucleotide is able to handle smaller insert sizes, down to about 100 bp, whereas the existing PT library workflow does not work with insert sizes smaller than 600 bp. For instance, the presence of a linking polynucleotide effectively increases the length of the polynucleotides of interest so that polynucleotides of interest that may not have readily circularized because of their shorter length can now circularize. In some embodiments, this is especially advantageous when coupled with a sequencing chemistry for longer reads, such as a 50 bp sequencing chemistry; thereby allowing a polynucleotide of approximately 100 bp in size to be sequenced in its entirety. Thus, various embodiments described herein can provide the capability of 100 bp reads (50 bp for each tag) without making additional changes in sequencing chemistry. In some embodiments, the longer reads can allow for de novo sequencing.

In light of the numerous aspects outlined above, it is clear that the disclosed embodiments can address a significant bottleneck step in existing PT library creation while at the same time providing higher efficiency and superior sample recovery. FIGS. 29A and 29B further display some advantages of some of the herein disclosed embodiments (FIG. 29A) over various techniques for producing paired tag libraries using other techniques (depicted in FIG. 29B). While some embodiments described herein will result in useful products from all ligation reactions (FIG. 29A), other approaches for producing paired tag libraries result in useful products for only 50% of the ligation products (FIG. 29B).

In some embodiments, the various methods and parts described herein can be employed with respect to a Support Oligo Ligation Detection (SOLiD™) kit, which can be used in making paired tag libraries.

While the embodiments in many of the above figures have been depicted as including P1 and/or P2 primer adaptors, in some embodiments, the adaptors in these embodiments do not include a priming site. Thus, alternative embodiments where the P1 and P2 primer adaptors are replaced with generic adaptors are also contemplated and disclosed herein.

In some embodiments, the methods described herein allow for the production of paired tags that are not size constrained. In some embodiments, the methods allow for the production of paired tags that are not processed by type IIs or type III restriction enzymes. Thus, in some embodiments, the methods and/or kits will not include a type IIs or type III restriction enzyme. In some embodiments, this allows for the production of a paired tag that includes ends that have not been processed by type IIs or type III restriction enzymes. Thus, in some embodiments, one or more of the sequences on the ends of the paired tag are not sequences that would result from cleaving by a type IIs or type III restriction enzyme. This also includes type IIs or III cutting sites that are subsequently blunted or manipulated in another way. In some embodiments, the paired tag lacks a type IIs and/or type III restriction site.

While the above sets out the general concepts involved in various embodiments for the production of paired tags, the following sections describe various specific embodiments and put forth specific examples to provide further description of the technique.

Double Stranded Polynucleotide of Interest

The double stranded polynucleotide of interest can come from any source such as a cellular or tissue nucleic acid sample, a subclone of a previously cloned fragment, mRNA, chemically synthesized nucleic acid, genomic nucleic acid samples, nucleic acid molecules obtained from nucleic acid libraries, specific nucleic acid molecules, and mixtures of nucleic acid molecules. Some embodiments of the disclosed methods are particularly suited to producing libraries of cloned nucleic acid molecules starting with a complex mixture of nucleic acid molecules to be represented in the library. For example, cDNA can be produced from all of the mRNA in a cellular sample and used to make a cDNA library, or a library of genomic DNA can be produced from a genomic nucleic acid sample.

In some embodiments, the nucleic acid sequence to be characterized can be a genome. A genome is the genomic DNA of a cell or organism. In some embodiments, the genome can be of a prokaryote, eukaryote, plant, virus, fungus, or an isolated cell thereof. In other embodiments, the genome can be a known (previously characterized or sequenced) genome. In other embodiments, the genome can be an unknown (not previously characterized or sequenced) genome. In some embodiments, characterizing a genome can comprise karyotyping the genome. Karyotyping is the analysis of the genome of a cell or organism. In other embodiments, characterizing the genome comprises polymorphism discovery or genotyping to identify differences between two or more nucleic acid sequences derived from different sources.

The polynucleotide, nucleic acid or DNA of interest can be essentially any nucleic acid of known or unknown sequence. It can be, for example, a fragment of genomic DNA or cDNA. Sequencing can result in determination of the sequence of the whole, or a part of the molecule of interest. The molecules of interest can be derived from a primary nucleic acid sample that has been randomly fragmented. The molecules of interest can be processed into polynucleotide of interest fragments suitable for amplification by, for example, the placement of universal amplification sequences at the ends of each fragment of interest. The molecules of interest can also be obtained from a primary RNA sample by reverse transcription into cDNA.

In some embodiments, the polynucleotides of interest can originate in double-stranded DNA (dsDNA) form (e.g. genomic DNA fragments, PCR and amplification products and the like). In some embodiments, the polynucleotides can have originated in single-stranded form, as DNA or RNA, and been converted to dsDNA form. By way of example, mRNA molecules can be copied into double-stranded cDNAs suitable for use in the method of the invention using standard techniques well known in the art. The precise sequence of the primary polynucleotide molecules is generally not material to the invention, and may be known or unknown.

Paired tags or paired reads can be obtained on fragments of any length, for example PCR amplicons of 2-10 Kb or DNA clones isolated from bacteria or other biological sources. The targets can be the ends of phosmid molecules of around 40 kB or the ends of Bacterial artificial chromosomes (BACs) of around 100-200 kB. The ends of polynucleotides derived from such sources can be sequenced without fragmentation to obtain the reads from the ends of each unfragmented polynucleotide, or the polynucleotide can be fragmented. The fragmented polynucleotides can be size selected, for example by gel electrophoresis, to obtain a narrow size distribution on the target fragments. Paired reads spaced throughout the sample can be used as a tool for de-novo assembly of a previously unsequenced sample, as well as for resequencing a sample where a reference genome is available. In some embodiments, the methods described herein are suitable for use with nucleic acid molecules obtained from any source, where knowledge of the sequences at either end of the molecules is desired.

In some embodiments, the polynucleotides of interest can be DNA molecules. In some embodiments the polynucleotide of interest can represent the entire genetic complement of an organism, and can be genomic DNA molecules, which include both intron and exon sequences (coding sequence), as well as non-coding regulatory sequences such as promoter and enhancer sequences. In embodiments wherein genomic DNA molecules are used, genome-wide analysis or analysis of the entire genome can be achieved. It is, however, envisaged that particular sub-sets of polynucleotide sequences or genomic DNA could also be used, such as, for example, particular chromosomes. In some embodiments, the sequence of the polynucleotide of interest may not be known. In some embodiments, the polynucleotide of interest can be human genomic DNA molecules. The DNA molecule of interest can be treated chemically or enzymatically, either prior to, or subsequent to any random fragmentation processes, and prior to or subsequent to the ligation of the adaptor sequences. Random fragmentation refers to the fragmentation of a polynucleotide molecule in a non-ordered fashion by enzymatic, chemical or mechanical means. Such fragmentation methods are known in the art and utilize standard methods (Sambrook and Russell, Molecular Cloning, A Laboratory Manual, third edition). Random fragmentation is designed to produce fragments irrespective of the sequence identity or position of nucleotides comprising and/or surrounding the break. Random fragmentation can be achieved by mechanical means such as nebulisation or sonication can produce fragments of, for example, about 50 base pairs in length to about 3000 base pairs in length, more particularly 50-2000 base pairs in length, more particularly 50-1500 base pairs in length, more particularly 50-1000 base pairs in length, and still more particularly 50-700 base pairs in length. In some embodiments, the method can used to generate fragments of from about 1000-2000 base pairs in length. In some embodiments, the method can used to generate fragments of from about 500-1000 base pairs in length. In some embodiments, the method can used to generate fragments of from about 50-150 base pairs in length.

In some embodiments, the polynucleotides of interest can be subjected to a size selection method to select for polynucleotide fragments of a particular size. The size selection method can be any of a variety of size selection methods known in the art, including without limitation electrophoresis, such as gel electrophoresis, and chromatography, such as HPLC and size exclusion chromatography. In some embodiments, fragments of, for example, about 50 base pairs in length to about 3000 base pairs in length, more particularly 50-2000 base pairs in length, more particularly 50-1500 base pairs in length, more particularly 50-1000 base pairs in length, and still more particularly 50-700 base pairs in length are selected by the size selection method. In some embodiments, the method can used to select fragments of from about 1000-2000 base pairs in length. In some embodiments, the method can used to select fragments of from about 100-1000 base pairs in length. In some embodiments, the size selection method can used to select fragments of from about 50-150 base pairs in length.

In various embodiments described herein, methods for characterizing a nucleic acid sequence are provided that comprises fragmenting a nucleic acid sequence to produce a plurality of nucleic acid sequence fragments having a 5' end and a 3' end. Fragmentation of polynucleotide molecules by mechanical means (nebulization, sonication and Hydroshear for example) results in fragments with a heterogeneous mix of blunt and 3'- and 5'-overhanging ends. The fragment ends can be repaired using methods or kits (such as the Lucigen DNA terminator End Repair Kit) known in the art to generate ends that are optimal for ligation, for example, to adaptors having blunt ends. Various restriction endonucleases, such as, for example, SmaI, can be used to produce blunt ends. In some embodiments, the fragment ends of the population of nucleic acids are blunt ended.

In some embodiments, such as the one shown in FIG. 1, the polynucleotide of interest lacks a 5' phosphate residue at both the 5' and 3' end. Although the polynucleotide of interest depicted in FIG. 1 appears to have blunt ends, in other embodiments, the polynucleotide of interest can have one sticky end and one blunt end, two sticky ends, or two blunt ends. In some embodiments, the adaptor can have one sticky end and one blunt end, two sticky ends, or two blunt ends.

In some embodiments, the polynucleotides of interest are prepared with at least one end lacking a 5' phosphate residue. For example, 5' phosphate residues can be removed by activity of alkaline phosphatases that catalyze the removal of 5' phosphate groups from DNA, RNA, ribo- and deoxyribonucleoside triphosphates. Treatment of a polynucleotide fragment with alkaline phosphatase

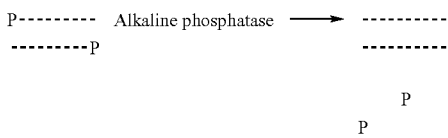

Thus, a 5' phosphate residue can be removed from the 5' end of a polynucleotide of interest. Examples of suitable alkaline phosphatases include calf intestinal alkaline phosphatase, bacterial alkaline phosphatase, shrimp alkaline phosphatase, antarctic phosphatase, and placental alkaline phosphatase. As will be appreciated by one of skill in the art, there are a variety of ways in which a nick can be introduced or result from the circularization of the polynucleotide of interest. All that is required from such techniques is that a nick be present in the circularized nucleic acid sequence.

In some embodiments, the ends of the polynucleotide of interest can be modified. For example, one or more adenines can be added when the adaptors that are to bind to the polynucleotides of interest include a one or more thymine. In some embodiments, the polynucleotides of interest retain their phosphate residues.

Adaptors, Circularization and Nick Introduction

In some embodiments, the polynucleotides of interest are modified to effectively remove the 5' phosphate from their exposed end by attaching one or more adaptors to an end of the polynucleotide. For example, an adaptor that lacks a 5' phosphate residue in one strand, can be ligated to the ends of the DNA fragment of interest. In some embodiments, the adaptor has at least one compatible end to an end of the polynucleotide of interest. In some embodiments the adaptor can have one blunt end, two blunt ends, two sticky ends, or two blunt ends. In some embodiments, the one end of the adaptor can be sticky and lack a 5' phosphate residue, and the other end of the adaptor can be blunt. In other embodiments, a first adaptor can be attached to the one end of the polynucleotide of interest, and a second adaptor having a different sequence from the first adaptor can be attached to the other end of the polynucleotide of interest. Either or both the first and second adaptors can lack a 5' phosphate residue in one strand. In some embodiments, the adaptors can be attached to the polynucleotide of interest by, for example, ligation.

As will be appreciated by one of skill in the art, in some embodiments, the adaptor can comprise any nucleotide sequence of any length. In some embodiments, the adaptors are configured so as to result in a nick or gap when ligated to a polynucleotide of interest or to another adaptor. In some embodiments, there will be a much greater concentration of the adaptor than the polynucleotide of interest when the adaptor is to be added to the polynucleotide of interest. In some embodiments, the adaptor is shorter than the polynucleotide of interest. In some embodiments, the adaptor is less than 500 bases, e.g., 400, 300, 200, 100, 50, or fewer bases in length.

In some embodiments, the adaptor comprises a bar code sequence. The adaptor bar code sequence can be detected by methods such as, for example, sequencing or hybridization. In some embodiments, bar code sequences can allow identification of different samples placed together in a single sequencing run. For example, 2, 3, 4, 5, 6, 7-10, 10-50, 50-100, 100-200, 200-500, 500-1000, or more different samples each having a unique bar code sequence can be placed together in a single sequencing run. The members of a paired tag can be identified using the unique bar code sequence associated with the particular adaptor of the paired tag. In some embodiments, the bar code is separate from the adaptor but still included in the paired tag. In some embodiments, the bar code is located between two adaptors. In some embodiments, the bar code is in more than one of the adaptors.

In some embodiments, the adaptor is coupled to a binding moiety.

In some embodiments, the adaptor (1, 2, 3, or all of the adaptors) does not include a restriction enzyme binding site. For example, in some embodiments, the adaptor (1 or more the adaptors in the circularized nucleic acid molecule) lacks a EcoP15I and MmeI restriction site. Thus, in some embodiments, adding a restriction enzyme that binds to a specific sequence, will not result in the cleavage of the circularized nucleic acid molecule.

Figure 7:
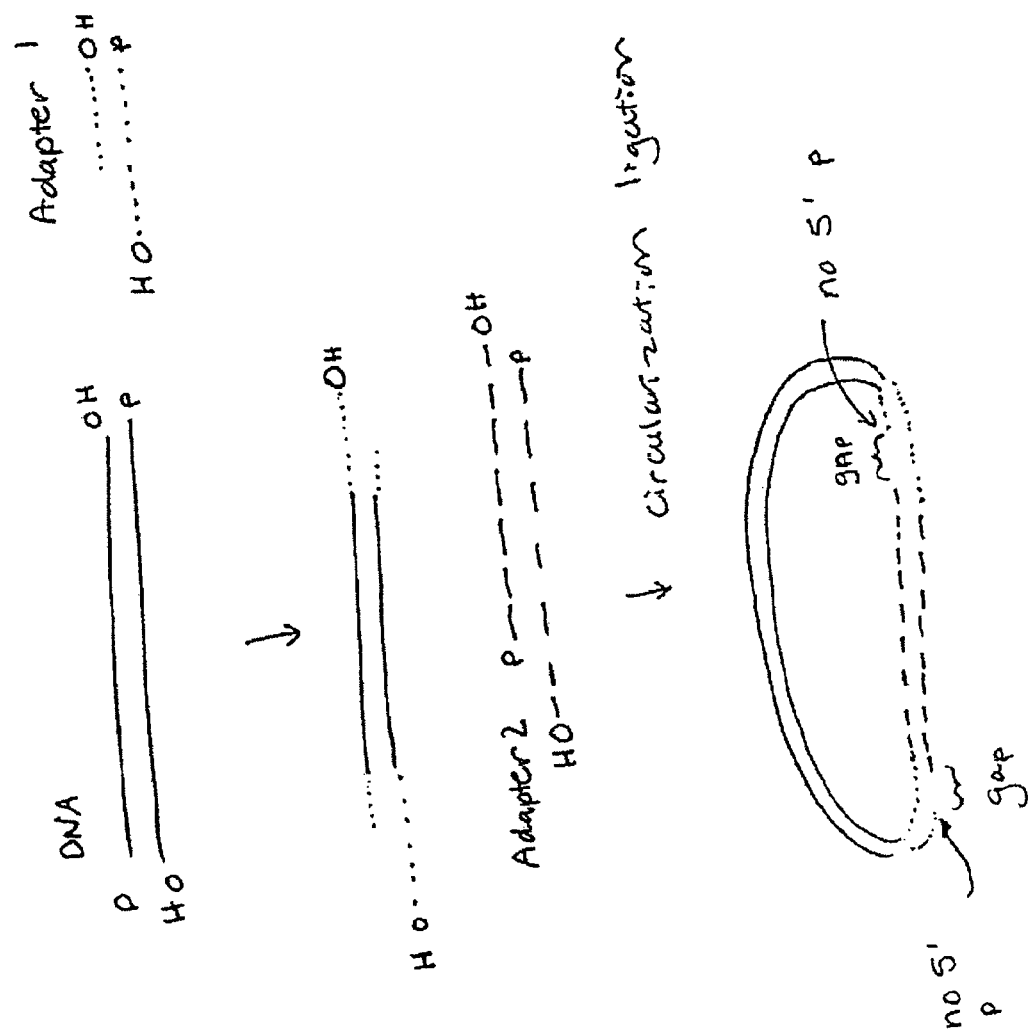
FIG. 7 depicts an embodiment for forming a gapped circular nucleic acid molecule.

In some embodiments, the attachment of the polynucleotide of interest to the adaptor can occur by, for example, ligation or annealing. In FIG. 1, the circular nucleic acid molecule has one nick on each of the different strands of the circular nucleic acid molecule. In the illustrated embodiment, the nick is initially located between the adaptor and the polynucleotide of interest. In some embodiments, the sequences of the ends of the polynucleotide and the adaptor can be such that upon attachment of the polynucleotide of interest to the adaptor, at least one gap can be formed between the polynucleotide of interest and the adaptor, as shown in FIG. 7. In some embodiments where there is a gap between the polynucleotide of interest and the adaptor, the 5' end of the polynucleotide strand flanking the gap can still have a 5' phosphate residue. This is because when a gap is introduced, the presence of a 5' phosphate residue does not affect the nick translation reaction. In some embodiments where there is a gap between the polynucleotide of interest and the adaptor, the 5' end of the polynucleotide strand flanking the gap can lack a 5' phosphate residue. In other words, the polynucleotide strand at the 3' end of the gap can lack a 5' phosphate residue, as shown in FIG. 7. It is not necessary that the polynucleotide strand at the 3' end of the gap lack a 5' phosphate residue. In some embodiments, the polynucleotide strand at the 3' end of the gap does not lack a 5' phosphate residue. In some embodiments the circular nucleic acid molecule can have one nick, one gap, two nicks on opposite strands, a nick on one strands and a gap on the opposite strand, or two gaps on opposite strands.

In some embodiments in the preparation of paired tag clones, a first set of adaptor sequences can be attached to a polynucleotide fragment of interest, as shown in FIG. 3. The attachment of the polynucleotide of interest to the adaptor can occur by, for example, ligation or annealing. In the embodiment shown in the figure, the polynucleotide of interest has blunt ends, which are ligated to the blunt end of adaptor 1. In other embodiments, one end of the polynucleotide of interest can be ligated to a first adaptor 1, and the other end of the polynucleotide of interest can be ligated to a second adaptor 1, and the first and second adaptor 1 can have the same or different sequences. In FIG. 3, adaptor 1 lacks a 5' phosphate residue at its sticky 5' end. The resulting molecule has sticky ends lacking 5' terminal phosphate residues. Next, both sticky ends of this molecule are ligated to the ends of adaptor 2, thereby forming a circular nucleic acid molecule having nicks on opposite strands, as shown in FIG. 3. The nicks are present between the end of the first adaptor and the second adaptor. In some embodiments, the sequences of adaptors 1 and adaptor 2 can be such that when adaptor 2 is ligated to adaptor 1, at least one gap is formed between adaptor 1 and adaptor 2. In some embodiments where there is a gap between adaptor 1 and adaptor 2, the 5' end of the polynucleotide strand flanking the gap can, but need not have a 5' phosphate residue. In other words, the polynucleotide strand at the 3' end of the gap can, but need not have a 5' phosphate residue. In some embodiments the circular nucleic can have one nick, one gap, two nicks on opposite strands, a nick on one strands and a gap on the opposite strand, or two gaps on opposite strands. In some embodiments, adaptor 1 can have one sticky end and one blunt end, two sticky ends, or two blunt ends. Adaptor 2 can have one sticky end and one blunt end, two sticky ends, or two blunt ends. A first adaptor 1 and a second adaptor 1 can both lack at least one 5' phosphate residue.

Figure 8:
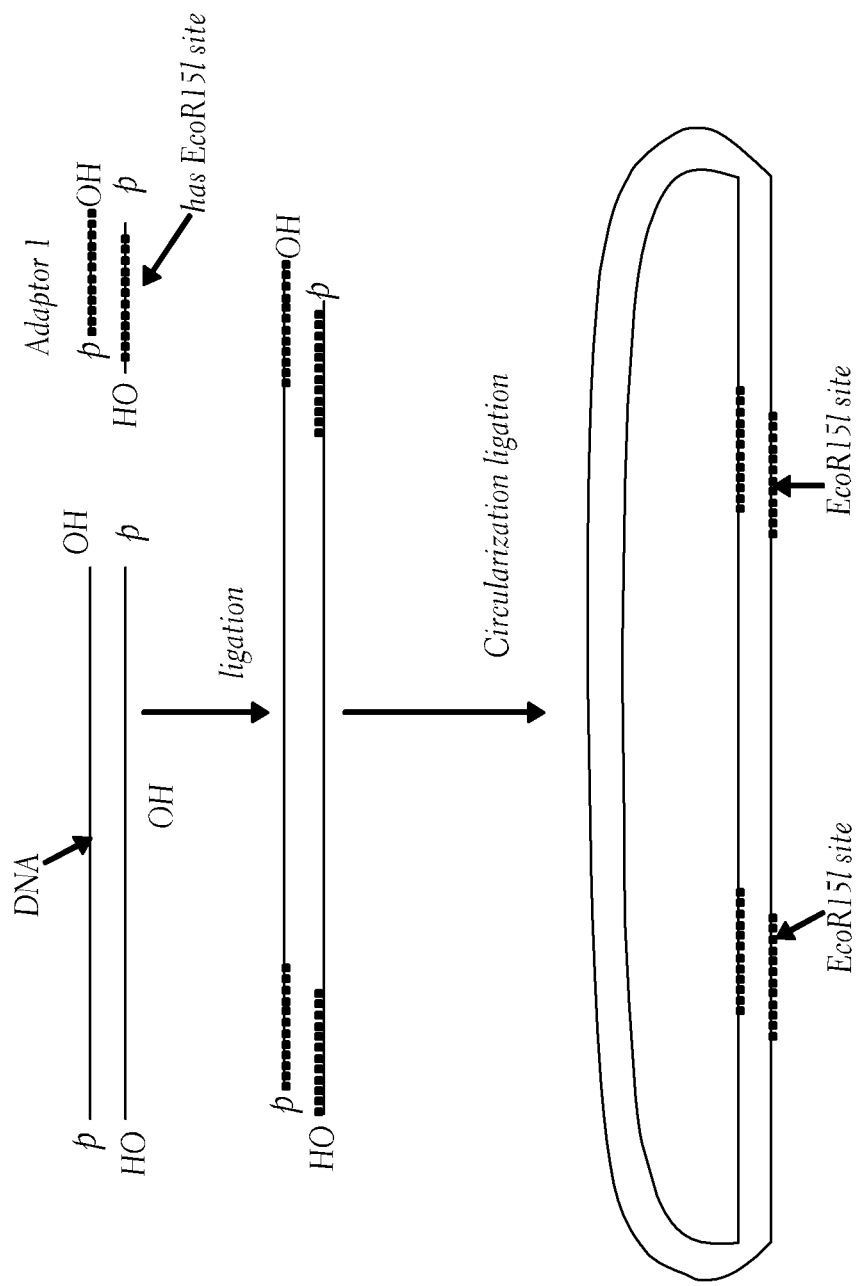
FIG. 8 depicts an embodiment for forming a circular nucleic acid molecule.
Figure 9:
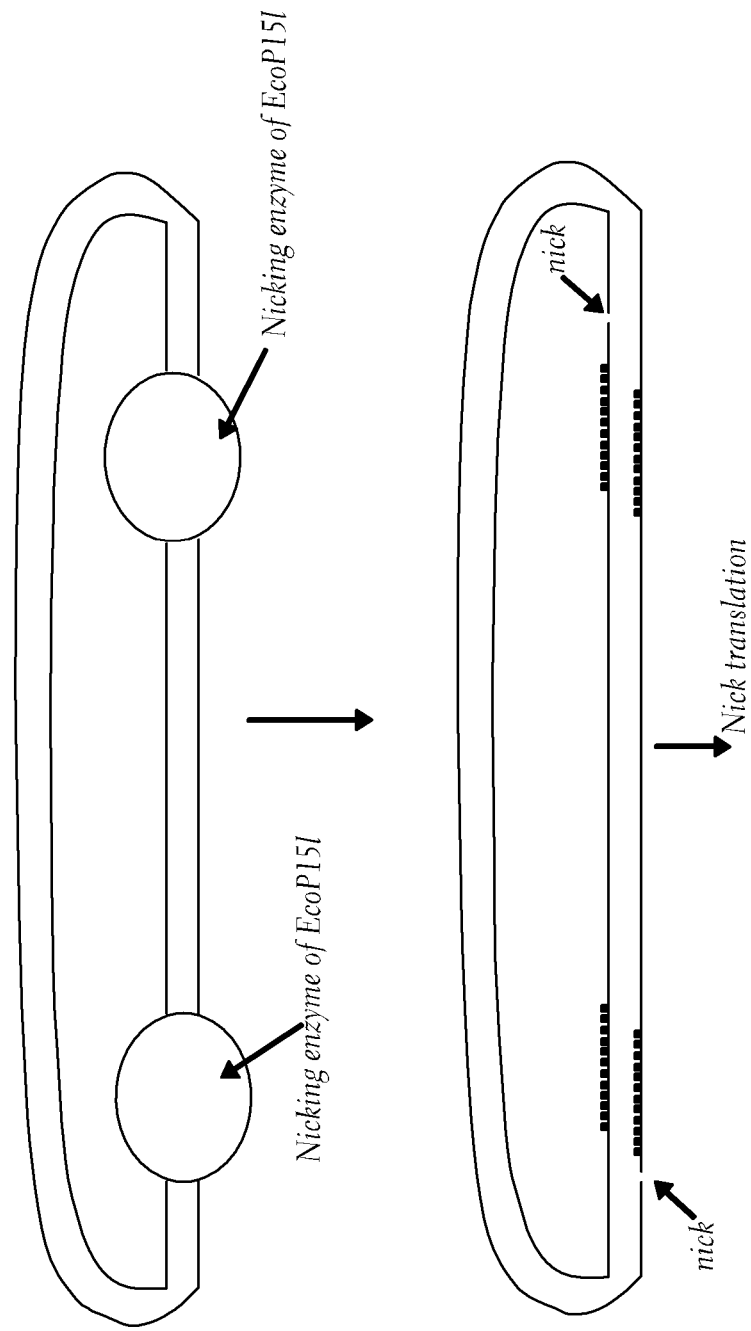
FIG. 9 depicts an embodiment for forming a nicked circular nucleic acid molecule.

In some embodiments, a nick is introduced to a circular nucleic acid molecule. In some embodiments, the location of nicks introduced to a circular nucleic acid molecule can be random. In some embodiments, the circular nucleic acid molecule can be designed to have recognition sites for a nicking restriction enzyme. In some embodiments, an adaptor containing a nicking restriction enzyme restriction site can be ligated to one or both ends of a polynucleotide of interest to create an adaptor modified polynucleotide of interest (FIG. 8). Next, the adaptor modified polynucleotide of interest can be circularized using another adaptor, as shown in FIG. 8. In other embodiments, an adaptor having nicking restriction enzyme sites at both ends can be ligated to both ends of a polynucleotide of interest to form a circular nucleic acid molecule. A nicking restriction enzyme specific for the sites introduced to the circular nucleic acid molecule can be used to produce a nick in one strand downstream of each nicking restriction enzyme site (FIG. 9).

Nicking restriction enzymes are known in the art and include, for example without limitation, EcoP15I, Nb.BbvCI, Nb.BsmI, Nb.BsrDI, Nb.BtsI, Nt.AlwI, Nt.BbvCI, Nt.BstNBI. Restriction enzymes such as EcoP15I and MmeI can be engineered into nicking enzymes using existing strategies. (Heiter, D F. et al, 2005, J. Mol. Biol., 348, 631-640; Samuelson, J. C., et al NAR, 32: 3661-3671; Zhu, Z. et al. 2004, J. Mol. Biol. 337: 573-583).

In some embodiments, in the preparation of paired tag clones, topoisomerase (Topo) can be used to improve circularization efficiency. Various topoisomerases can be used, including types IA, IB, II, etc. In some embodiments, the topoisomerase can be topoisomerase I. In some embodiments, adaptors having a Topo binding site can be employed ("Topo binding adaptors"). The Topo binding site sequence will depend on the particular topoisomerase used. In some embodiments, the Topo binding site is or comprises YCCTT, where Y can be C or T. In some embodiments, the adaptor can have a Topo binding site at the 3' end of one or both strands. In other embodiments, the Topo binding adaptor can have a Topo binding site at the 3' end of each strand of the adaptor. In some embodiments, the Topo binding adaptor has one or more extra bases extending beyond the Topo binding site at the 3' end of one or both strands. The Topo binding adaptor can have blunt ends, sticky ends, or one blunt end and one sticky end.

In some embodiments, the Topo binding adaptor has a gap or nick on one or both strands. An example of a Topo binding adaptor is depicted in FIG. 10. As shown in FIG. 10, a Topo binding adaptor having a gap or nick on opposite strands is formed by combining the four oligonucleotides, Topo-IA-A-1, Topo-IA-B-1, Topo-IA-A-2 and Topo-IA-B-2. Oligonucleotides Topo-IA-B-1 and Topo-IA-A-2 each have a Topo binding site at the 3' end and lack a 5' phosphate. In the depicted embodiment, Topo-IA-A-1 is coupled to a binding moiety, biotin. The resulting Topo binding adaptor (shown at bottom of FIG. 10) has Topo binding sites at the 3' end of both strands, nicks on opposite strands, gaps/nick and is coupled to biotin.

Addition of topoisomerase to the Topo binding adaptor can generate a topoisomerase-adaptor complex, as shown in FIG. 11. As will be appreciated by one of skill in the art, during complex formation, Topoisomerase I covalently binds to the adaptor at the Topo binding site. (See, e.g. Shuman, *Proc. Natl. Acad. Sci. USA, Vol.* 88, pp. 10104-10108, 1991.) The phosphodiester backbone after the 5'YCCTT site in a strand of the adaptor is broken, and a phosphotyrosil bond forms between the 3' phosphate of the cleaved strand and the Tyr274 residue of Topoisomerase I (FIG. 11). The phosphotyrosil bond can subsequently be attacked by the 5' hydroxyl group of a dephosphorylated polynucleotide (FIG. 12). In some embodiments, the DNA inserts (which can be used for library construction in some embodiments) can be dephosphorylated and 3' tailed with relevant nucleotide or nucleotides using Taq or any other appropriate method for generating overhangs. As will be appreciated by one of skill in the art, the specific bonding reaction between the topoisomerase and adaptor will vary depending on the particular topoisomerase used.

In some embodiments, a polynucleotide of interest can be dephosphorylated. Examples of dephosphorylation of a polynucleotide of interest are discussed above. In some embodiments, the dephosphorylated polynucleotide of interest is 3' tailed with a desired nucleotide. 3' tailing can be performed using a variety of methods for generating overhangs. In some embodiments, Taq is used to 3' tail the dephosphorylated polynucleotide of interest to generate overhangs. In some embodiments one or more nucleotides can be added to the 3' end of one or both strands of the polynucleotide of interest. In some embodiments a single nucleotide can be added to the 3' end of each strand of the polynucleotide of interest. In the embodiment depicted in FIG. 12, the dephosphorylated polynucleotide of interest has a single A overhang at the 3' end of each strand.

In some embodiments, the topoisomerase-adaptor complex is combined with a dephosophorylated polynucleotide of interest. The 5' hydroxyl groups of a dephosphorylated polynucleotide of interest can attack the phosphotyrosil bond of the topoisomerase-adaptor complex, as shown in FIG. 12. A circular nucleic acid molecule comprising the adaptor and the polynucleotide of interest is formed, as shown in FIG. 13. In some embodiments, the circular nucleic acid can have a nick on opposite strands within the adaptor.

As noted above, in some embodiments, more than one adaptor can be used. Furthermore, in some embodiments, a linking polynucleotide can be used to connect a first and a second adaptor and thereby form a nicked linking polynucleotide. In some embodiments, circularization is achieved via at least two adaptors. In some embodiments, an internal adaptor is also employed at a later point in the process (e.g., FIGS. 27 and 28).

As noted above, in some embodiments, a nick is present between an adaptor and a polynucleotide of interest. In some embodiments, the nick is present in a nicked vector. In some embodiments, the nick is not located between an adaptor and a polynucleotide of interest, but is located between an adaptor and a linking polynucleotide. In some embodiments, the nick can be expanded into a gap to allow for increased digestion efficiency by the single strand specific endonucleases (or exonucleases).

In some embodiments, the adaptors are modified to lack a phosphate group so that a nick and/or gap is formed when the adaptors are connected to the linking polynucleotide. In some embodiments, the nick and/or gap is between the polynucleotide of interest and an adaptor. In some embodiments, the nick and/or gap is between the linking polynucleotide and an adaptor. In some embodiments, the nick and/or gap is within the polynucleotide of interest. In some embodiments, the nick and/or gap is within the linking polynucleotide.

In some embodiments, circularization of a polynucleotide of interest can involve modifying the ends of the polynucleotide of interest and/or the adaptors. In some embodiments, the modification reduces the likelihood that a nicked linking polynucleotide can self-ligate. In some embodiments, the modification is the addition of one or more nucleotides (e.g., thymines) on the ends of the adaptor portions of the nicked linking polynucleotide. The additional nucleotides are selected such that they reduce the likelihood of self-ligation (e.g., the ends will not hybridize to one another). Of course, the polynucleotide of interest will be modified so that it will hybridize to the ends of the modified adaptors. In some embodiments, the ends of a released paired tag can also be modified (with the ends of an internal adaptor being modified appropriately as well).

In some embodiments, the nick is converted into a gap, as described herein, and then the process continues with a gap instead of a smaller nick. In some embodiments, this allows for more efficient cleaving at the single stranded section to release the paired tag.

Nick Translation and/or Extension of a 3' Side of a Nick

In various embodiments after formation of the circular nucleic acid molecule having at least one nick or gap, a nick translation reaction can be performed, as shown in FIG. 2 and FIG. 4. The nick translation reaction translocates at least one nick present in the circular nucleic acid molecule to a position within the polynucleotide of interest. FIG. 4 schematically depicts the results of a nick translation reaction performed on the circular nucleic acid molecule shown in FIG. 3. The nick translation reaction can translocate each of the nicks in the circular nucleic acid molecule through adaptor 1 to a position within the polynucleotide of interest, as shown in FIG. 4.

In some embodiments, the nick translation can be performed on a linear nucleic acid molecule. As such, a molecule does not have to be circular during the nick translation reaction.

Methods for performing nick translation reactions are known to those of skill in the art (Rigby, P. W. et al. (1977), J. Mol. Biol. 113, 237). A variety of suitable polymerase can be used to perform the nick translation reaction, including for example, E. Coli DNA polymerase I, Taq DNA polymerase, Vent DNA polymerase, Klenow DNA polymerase I, and phi29 DNA polymerase. Depending on the enzyme used, the nick translation can occur by 5' to 3' exonuclease activity, or by 5' to 3' strand displacement. When a gap is present in the circular nucleic acid molecule, the gap is first filled in with nucleotides by a 5' to 3' polymerase activity, thereby resulting in a nick. In some embodiments, a mutant enzyme with low activity is used for the nick translation reaction. The mutant enzyme can have, for example, low rates of extension, low 5' to 3' exonuclease activity, low 5' to 3' polymerase activity, low 5' to 3' strand displacement activity, or combinations thereof. In some embodiments, the mutant enzyme is sensitive to reaction conditions such as, for example, temperature or pH.

As will be appreciated by one of skill in the art, the reaction conditions can be varied to control the length of the nick translation product. For example, the length of the nick translation reaction product, i.e., the distance the nick is moved, can depend on the reaction conditions, such as reaction time, reaction temperature, the polymerase used, pH, ions present, salt conditions, etc. As discussed above, a mutant polymerase can be used, including temperature-sensitive polymerases. Thus, the method allows one to control the length of the sequence tag produced. In some embodiments, the nick translation is stopped prior to the cleavage step. As will be appreciated by one of skill in the art, the nick translation can be stopped or slowed by increasing the temperature, decreasing the temperature, altering the pH, altering the ions present, altering the salt conditions, addition of a chelating agent, etc.

In some embodiments, a nick translation reaction is performed using E. coli DNA polymerase I for 5 minutes at 0° C. In some embodiments, the nick translation reaction can proceed from about 1 to about 20 minutes. In some embodiments, the nick translation reaction is terminated by heating after the reaction has proceeded for about 1, 2, 3, 4, 5, 6, 7, 8, 9, 10, 11, 12, 13, 14, 15, 16, 17, 18, 19 or 20 minutes. In some embodiments, the nick translation reaction is performed at temperature from between about 0° C. to about 40° C. In some embodiments, the nick translation reaction is performed at about 0° C., 4° C., 30° C., room temperature or 37° C.

In some embodiments, the nick translation reaction can be allowed to continue for a desired length around the circularized nucleic acid, and then the reaction can be terminated. Termination can be performed by any of a number of suitable means, including, for example, by heating or by addition of an appropriate stop solution or buffer. In some embodiments at least one nick can be translated for at least 1 base e.g. at least 1, 2, 3, 4, 5, 6, 7, 8, 9, 10, 15, 16, 17, 18, 19, 20, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 800, 1000, 1500, and 2000 or more bases. In some embodiments, at least one nick can be translated between 10 and 2000 bases. In some embodiments, at least one nick can be translated between 10 and 500 bases. In some embodiments, at least one nick can be translated between 10 and 200 bases. In some embodiments, at least one nick can be translated between 10 and 100 bases. In some embodiments, at least one nick can be translated between 20 and 50 bases. In some embodiments, the lower boundary for any of the above ranges is 28 bases. In some embodiments, the upper boundary for any of the above ranges is 2000 bases. In other embodiments, the nick translation reaction can continue until two opposing nicks meet at one point, forming a break in the circular nucleic acid molecule.

In some embodiments, the end of the polynucleotide that comprises part of the nick and/or gap is simply moved or extended and need not be translated by a nick translation enzyme. In some embodiments, the 3' end of an adaptor is moved and/or extended off of (for example, as shown in FIGS. 16 and 17). In some embodiments, one or more of the adaptors is removed and then extension occurs off of one of the remaining adaptors (e.g. FIG. 20).

In some embodiments, the nick and/or gapped circularized nucleic acid can be exposed to an exonuclease digest (such as 5' to 3' exonuclease digest) (FIG. 16). This results in some or all of the double stranded polynucleotide of interest becoming single stranded (as well as optionally removing one or more of the strands of the adaptors). Following this, the resulting product can be extended from the remaining 3' ends or sides of the nick (for example via a DNA polymerase, as shown in FIG. 17). Effectively, this allows for the 3' end of the nick to be extended or moved, even though the 5' end that previously comprised the nick has been moved much further away (FIG. 17) or has been practically removed (FIG. 20). In some embodiments, this process can be considered to involve a very large gap structure. This process can also be described as simply extending or moving the 3' end or part of the nick.

In some embodiments, the part of the strand comprising the 5' side of the nick is digested prior to the extension. In some embodiments, the digestion starts at the part of the strand comprising the 5' side of the nick. In some embodiments, the strand comprising the 5' end is digested via a 5' to 3' exonuclease, such as T7 exonuclease or lambda exonuclease. In some embodiments, an exonuclease is not required. In some embodiments, for example, a helicase can be used to unwind DNA at the nick and/or gap. In some embodiments, the helicase unwinding and the polymerase 3' extension can happen in the same reaction tube at the same time. Other appropriate enzymes or processes that can displace the 5' end can also be employed.

Any of the herein described aspects relating to "nick translation," can also be applied, as appropriate, to the above noted extension process (e.g. the number of bases moved, etc.)

Nick Cleavage and Single Strand Cleavage

As noted above, the translocation of the nicks to within the polynucleotide of interest allows cleavage at a position within the polynucleotide of interest, thus allowing manipulation of base sequences of the polynucleotide sequences between the adaptor(s) and the nick. In some embodiments, the nick translation reaction can be terminated prior to cleavage. As shown in FIG. 5, cleavage of the polynucleotide strand opposite the nicks in a circular nucleic acid molecule after the nick translation reaction is terminated can "release" a paired tag clone comprising two tags from each end of the polynucleotide of interest. In some embodiments, the solution containing the released paired tag can include the paired tag, and the remaining section of the polynucleotide of interest that will be the section of the polynucleotide of interest, minus the two tag sequences, which are now part of the paired tag.

In some embodiments, the paired tag clone comprises at least one adaptor flanked by tags (a first and a second tag) from opposite ends of the polynucleotide of interest. The paired tag depicted in FIG. 5 comprises adaptor 2 flanked on both sides by adaptor 1. The end regions of the paired tag in FIG. 5 comprise sequence tags from opposite ends of the polynucleotide of interest. Cleavage of the strand opposite a nick can be performed by a variety of suitable nucleases, including, for example without limitation S1 nuclease, mung bean nuclease, nuclease P1, and nuclease BAL-31. In some embodiments, the polynucleotide strand opposite the nick can be cleaved.

When strand displacement enzymes are used to move the nicks into the polynucleotide of interest, the displaced strand can also be digested by S1 nuclease, mung bean nuclease, nuclease P1 or nuclease BAL-31.

In some embodiments, the circularized nucleic acid molecule is cleaved by allowing nick translation to occur around the nucleic acid molecule until it encounters the other nick; thereby resulting in a self cleaved molecule. As such, in some embodiments, the entire polynucleotide of interest can be on the paired tag, with approximately half in the first tag and the other half in the second tag. As will be appreciated by one of skill in the art, such paired tag could be relatively large, depending upon the initial size of the polynucleotide of interest. Thus, in some embodiments, if one desires to allow the nick translation step to produce the released paired tag, one can start with appropriately sized polynucleotides of interest. For example, one can start with polynucleotides of interest that are less than 1000, 900, 800, 700, 600, 500, 400, 300, 200, or 100 bases in length, thereby resulting in tags that are less than 500, 450, 400, 350, 300, 250, 200, 150, 100, or 50 bases in length.

As described herein, in some embodiments, rather than a single phosphodiester bond missing in the nick, there is a gap present. In some embodiments, this allows for more effective processing and cleaving to create the released paired tag. In some embodiments, the gap effectively extends to the end of the strand; and thus, the entire polynucleotide of interest is single stranded. In such embodiments, as the end is single stranded, exonucleases and/or endonucleases can be used to release the paired tags.

In some embodiments, cleaving the polynucleotide of interest to form the released paired tag does not require a separate cleaving enzyme. For example, as shown in the embodiments in FIGS. 19-21, in some embodiments, a 5' to 3' exonuclease can be allowed to digest the circularized molecule until it linearizes the circular molecule. In some embodiments, the single stranded polynucleotide of interest can still be removed by a single strand specific exonuclease (e.g., as shown in FIG. 21).

Further Processing of the Paired Tags

In some embodiments, the paired tag clones can be purified by a variety of methods known in the art to remove unwanted molecules. In some embodiments, the adaptor in the paired tag clone can be coupled to a binding moiety. The binding moiety can be any binding moiety that can be coupled to an adaptor, such as, for example, biotin. The binding moiety can be used for, for example, attaching paired tag clones to a solid support. The solid support can be, for example without limitation, an array or microarray. In some embodiments, the solid support is a bead on a microarray. Nucleic acid molecules incorporating a binding moiety can be purified by affinity capture using a number of methods known in the art, such as the use of a purifying moiety that binds to the binding moiety specifically, for example, streptavidin. Affinity capture methods typically involve the use of capture reagents attached to a substrate such as a solid surface, magnetic bead, or semisolid bead or resin.

In some embodiments, one or more primer adaptors can be attached to one or more ends of a paired tag clone. In FIG. 6, primer adaptors P1 and P2 are attached to the ends of the paired tag clone. The primer adaptors can be use for a variety of purposes. For example, the paired tag can be amplified using the primer adaptors. In some embodiments, amplification can be a clonal amplification such as, for example, emulsion polymerase chain reaction (emulsion PCR), bridge polymerase chain reaction (bridge PCR), or combinations thereof. In some embodiments, the primer adaptors can be used for sequencing at least a portion of the paired tag clone, as shown in FIG. 6.

In some embodiments, a subsequent or additional nick translations reaction can be performed on the paired tag clone. For example, if the primer adaptors were not phosphorylated, an additional nick translation can be performed after the primer adaptors are attached to the ends of the paired tag clone to, for example, facilitate subsequent PCR amplification.

As will be appreciated by one of skill in the art, the production of a paired tag clone from a polynucleotide of interest has many applications. For example, it can allow for the ready characterization of the polynucleotide of interest. In some embodiments, characterizing a nucleic acid sequence comprises sequencing the paired tags produced from the nucleic acid sequence. Sequencing methods are standard in the art, and include, for example, traditional sequencing using the Maxam and Gilbert technique or the Sanger method, or by hybridization to an array or microarray of known oligonucleotides on, for example, a chip. Alternative approaches include sequencing by synthesis methods in which primer-polynucleotide of interest complexes are immobilized, for example, to a substrate such as a polymer, a magnetic bead, or a solid surface, and are extended using a DNA polymerase or DNA ligase in the presence of labeled substrates such that the addition products can be characterized to determine the DNA sequence. In some embodiments, various embodiments for producing the paired tags can be beneficial in preparing a polynucleotide of interest, or a part thereof for Support Oligo Ligation Detection (SOLiD™) sequencing or other massively parallel sequencing techniques.

Further Embodiments

Methods for preparing paired tag libraries and the libraries themselves are contemplated. In some embodiments, the methods comprise fragmenting a nucleic acid sequence to produce a plurality of polynucleotide fragments having a 5' end and a 3' end. One or more adaptors can be joined to the ends of each polynucleotide fragment to produce a plurality of circular nucleic acid molecules, wherein a nick or gap is introduced between the adaptor and the polynucleotide fragment. In some embodiments, a nick or gap is present between each end of the polynucleotide fragment and an adaptor. In preparing the circular nucleic acid molecules for the paired tag library, any of the methods described above can be used. A nick translation reaction can be performed on the circular nucleic acid molecules to produce a plurality of circular nucleic acid molecules each having at least one nick present within its corresponding polynucleotide fragment. The resulting circular nucleic acid molecules can be cleaved at a point opposite a nick to release the paired tag clones, thereby producing a paired tag library.

In some embodiments, the libraries employ internal adaptors.

Kits

In some embodiments, kits are provided for making paired tags. The kits can comprise reagents for ligating a polynucleotide of interest to an adaptor to form a circular nucleic acid molecule having a first nick or gap between the first end of the polynucleotide of interest and the adaptor, and a second nick or gap between the second end of the polynucleotide of interest and the adaptor, and reagents performing a nick translation reaction. In some embodiments, the amplification reagents are not included. In addition, a set of instructions and genome assembly guides can be included. Such material can be, for example, in print or in digital form. In some embodiments, enzymes or ingredients are included to adjust the 5' or 3' end of the polynucleotide of interest or the adaptors in order to include the relevant nicks in the circularized nucleic acid molecule.

In some embodiments, the kits include a nicked linking polynucleotide, which includes the linking polynucleotide and two adaptors ligated thereto. In some embodiments, the kit includes these three sections, but the sections are not ligated together. In some embodiments, the kits include a binding moiety, such as biotin/streptavidin moieties, such as shown in FIG. 22-28 (or any other linking combination), to allow ready manipulation of the polynucleotides. In some embodiments, the kit includes primers for a SOLiD™ based process. In some embodiments, the SOLiD™ primers are complementary to at least a part of one of the strands in P1 and/or P2, as shown in FIGS. 22-28. In some embodiments, the kit includes one or more internal adaptors. In some embodiments, the kit includes one or more enzymes for ligation, nick translation, 3' end extension, the addition of sticky ends, a single strand cleaving enzyme (including endonucleases and exonucleases), PCR amplification, ingredients for emulsion PCR, and ingredients for SOLiD™ sequencing.

In some embodiments, the kits include any one or more of the enzymes and/or polynucleotides described herein.

In some embodiments, a computer program is included (or can be provided separately) that compares the results of sequencing of paired tag clones produced by the methods disclosed herein. In some embodiments, the program identifies and assembles the sequence information from paired tag clones from a paired tag library. In this manner, a single complete, highly accurate, sequence can be provided by the program. In some embodiments, the program performs any of the methods described herein.

EXAMPLES

Embodiments of the present teachings can be further understood in light of the following examples, which should not be construed as limiting the scope of the present teachings in any way.

Example 1

This Example illustrates one method of making of a paired tag clone.

Plasmid DNA pUC19 was linearized with restriction enzyme SmaI and used as a model DNA polynucleotide of interest. Adaptor 1 was ligated to the ends of the DNA polynucleotide of interest. The resulting construct was circularized by ligation with adaptor 2. Adaptor 2 was labeled with biotin to facilitate downstream purification. Half of the circular DNA was used in nick translation reaction using *E. Coli* DNA polymerase I for 5 minutes at 0° C. The other half of the circular DNA was saved as no-nick-translation control. The nick translated DNA and the no-nick-translation control were digested with S1 nuclease at 37° C. for 15 minutes. The S1 digested DNA was end repaired, then purified by binding to streptavidin magnetic beads, and ligated with P1 and P2 primer adaptors. The resulting DNA was PCR amplified with P1 and P2 primers.

The PCR products were analyzed on agarose gel. The PCR products of the nick translation reaction product were longer than the PCR products of the control reaction as expected. In addition, the PCR products of the nick translation reaction showed a smear, indicating a range of product lengths from about 100 bp to greater than 200 bp.

Example 2

This Example illustrates a method of making of a paired tag clone using pUC19.

pUC19 DNA was digested with SmaI and the linearized DNA was purified with QIAGEN™ MinElute Reaction Cleanup Kit.

Adaptor 1 was ligated to the linearized pUC19 DNA using NEB Quick Ligation Kit. Subsequently, the reaction was cleaned up with QIAGEN™ MinElute Reaction Cleanup Kit. The ligation product was agarose gel purified with QIAGEN™ MinElute Gel Extraction Kit.

The above ligation product was circularized by ligation with adaptor 2 using NEB Quick Ligation Kit. The reaction was then cleaned up with QIAGEN™ MinElute Reaction Cleanup Kit.

The above reaction products were digested with Epicenter Plasmid safe DNase to remove any linear DNA and then cleaned up with QIAGEN™ MinElute Reaction Cleanup Kit.

The circular DNA from above was nick translated using *E coli* DNA polymerase I for 5, 10, or 15 minutes at 0° C. The reaction was stopped by adding the ERC buffer from QIAGEN™ MinElute Kit. The reaction was then cleaned up with QIAGEN™ MinElute Reaction Cleanup Kit.

The nick translated DNA from above was digested with Invitrogen S1 nuclease at 37° C. for 15 minutes to release the paired tag DNA. The reaction was then cleaned up with QIAGEN™ MinElute Reaction Cleanup Kit.

The DNA from the above step was end repaired using Epicentre EndIt kit.

The paired tag DNA was purified by binding to streptavidin beads.

P1 and P2 primer adaptors were ligated to the paired tag DNA.

PCR amplification of the pUC19 paired tag clones was performed using P1 primer and P2 primer to amplify the pUC19 paired tag.

The PCR products of the paired tags generated by nick translation at 0° C. for 5, 10, and 15 minutes were analyzed in separate lanes on agarose gel. Each showed a smear, indicating a range of product lengths from about 100 bp to greater than 200 bp. The PCR products of the paired tag generated at 0° C. for 15 minutes were on average longer than the PCR products of the paired tag generated at 0° C. for 10 minutes, which were on average longer than the PCR products of the paired tag generated at 0° C. for 5 minutes.

Example 3

This Example illustrates a method of making of a paired tag clone library using DH10B genomic DNA. In this Example, 30 μg of DH10B genomic DNA was hydrosheared to produce polynucleotides of interest. The ends of the polynucleotides of interest produced by hydroshearing were repaired using the ENDIT™ kit. The polynucleotides of interest were then purified using QIAGEN™ MinElute Reaction Cleanup Kit.

Adaptor 1 was ligated to the ends of the polynucleotides of interest from above step with NEB Quick Ligation kit.

The reaction was cleaned up using the QIAGEN™ MinElute Reaction Cleanup Kit. Adaptor modified polynucleotides of interest from 2 kb to 3 kb in length were selected using DNA on agarose gel. The gel-selected adaptor modified polynucleotides of interest were purified using the QIAGEN™ MinElute Gel Extraction Kit.

The gel-selected adaptor modified polynucleotides of interest were circularized by ligation with adaptor 2. Adaptor 2 contained a biotin binding moiety.

The reaction was then cleaned up using QIAGEN™ MinElute Reaction Cleanup Kit.

The above reaction products were digested with Epicenter Plasmid safe DNase to remove any linear DNA and then cleaned up with QIAGEN™ MinElute Reaction Cleanup Kit.

The circular DNA from above step was nicked translated using *E coli* DNA polymerase I at 0° C. for 15 minutes. The reaction was stopped by adding the ERC buffer from QIAGEN™ MinElute Kit. The reaction was cleaned up using the QIAGEN™ MinElute Reaction Cleanup Kit.

The paired tag clones were released by S1 nuclease digestion at 37° C. for 15 minutes. The reaction was cleaned up using the QIAGEN™ MinElute Reaction Cleanup Kit.

The DNA from above step was end repaired with Epicentre EndIt kit. The resulting paired tag clones were purified by binding to streptavidin beads.

P1 and P2 primer adaptors were ligated to the paired tag clones.

Trial PCR amplification was performed with P1 primer and P2 primer to determine proper cycle number. Subsequently, large scale PCR was performed to amplify the paired tag clone library. The final paired tag clone library was selected using agarose gel electrophoresis.

The PCR products were analyzed on agarose gel as shown in FIG. 10. Lane 1 contains a 25 bp DNA ladder. Lane 2-9 contains the PCR products from a 2-fold serial dilution of templates.

Example 4

This Example illustrates another method of making of a paired tag clone.

In this Example, a blunt-ended polynucleotide of interest can be treated with alkaline phosphatase to remove the 5' phosphate residues from the ends. The polynucleotide is then circularized by ligation with adaptor as shown in FIG. 1. The adaptor can be labeled with biotin to facilitate downstream purification. The circular nucleic acid molecule has a first nick between the polynucleotide of interest and the adaptor on one strand of the polynucleotide duplex, and a second nick between the polynucleotide of interest and the adaptor on a different strand of the polynucleotide duplex. A nick translation reaction is performed as depicted schematically in FIG. 2. The nick translation reaction can be performed using, for example, *E. coli* DNA polymerase I for, for example, about 5 minutes at about 0° C. The nick translation reaction is terminated by heating. The nick translated polynucleotide is digested with, for example, S1 nuclease at, for example, 37° C. for about 15 minutes. The S1 digested DNA is purified by binding to streptavidin magnetic beads. Primer adaptors P1 and P2 are attached to the ends of the paired tag clone that is bound to the magnetic beads via the adaptor. The paired tag is clonally amplified with P1 and P2 primers. The amplified paired tag clone can be subsequently sequenced.

Example 5

This Example illustrates another method of making of a paired tag clone.

In this Example, adaptor 1 is ligated to both ends of a polynucleotide of interest as shown schematically in FIG. 3. The 5' end of adaptor 1 lacks a 5' phosphate residue. The resulting construct is then circularized by ligation with adaptor 2 as shown in FIG. 3. Adaptor 2 can be labeled with biotin to facilitate downstream purification. The circular nucleic acid molecule has a first nick between adaptor 1 and adaptor two on one strand of the polynucleotide duplex, and a second nick between adaptor 1 and adaptor 2 on a different strand of the polynucleotide duplex. A nick translation reaction is performed as depicted schematically in FIG. 4. The nick translation reaction can be performed using, for example, *E. coli* DNA polymerase I for, for example, about 5 minutes at about 0° C. The nick translation reaction is terminated by heating. The nick translated polynucleotide is with, for example, S1 nuclease at, for example, 37° C. for about 15 minutes. The S1 digested DNA is purified by binding to streptavidin magnetic beads. Primer adaptors P1 and P2 are attached to the ends of the paired tag clone that is bound to the magnetic beads via the adaptor as shown in FIG. 6. The paired tag is clonally amplified with P1 and P2 primers. The amplified paired tag clone can be subsequently sequenced.

Example 6

This Example illustrates another method of making of a paired tag clone.

In this Example, adaptor 1 is ligated to both ends of a polynucleotide of interest as shown schematically in FIG. 3.

The 5' end of adaptor 1 may or may not have a 5' phosphate residue. The resulting construct is then circularized by annealing with adaptor 2 as shown in FIG. 7. Adaptor 2 can be labeled with biotin to facilitate downstream purification. The circular nucleic acid molecule has a first gap between adaptor 1 and adaptor two on one strand of the polynucleotide duplex, and a second gap between adaptor 1 and adaptor 2 on a different strand of the polynucleotide duplex. A nick translation reaction is performed as depicted schematically in FIG. 4. The nick translation reaction can be performed using, for example, E. coli DNA polymerase I for, for example, about 5 minutes at about 0° C. The nick translation reaction is terminated by heating. The nick translated polynucleotide is with, for example, S1 nuclease at, for example, 37° C. for about 15 minutes. The S1 digested DNA is purified by binding to streptavidin magnetic beads. Primer adaptors P1 and P2 are attached to the ends of the paired tag clone that is bound to the magnetic beads via the adaptor as shown in FIG. 6. The paired tag is clonally amplified with P1 and P2 primers. The amplified paired tag clone can be subsequently sequenced.

Example 7

This Example illustrates another method of making of a paired tag library.

In this Example, nucleic acid sequence is fragmented to produce a plurality of polynucleotide fragments having a 5' end and a 3' end. The polynucleotide fragments are subjected to a size selection method to select fragments from about 2 kb to about 3 kb. The polynucleotide fragment ends are blunt-ended, then treated with alkaline phosphatase to remove 5' phosphate residues from the ends. Adaptors are joined to the ends of each polynucleotide fragment to produce a plurality of circular nucleic acid molecules, wherein a nick is introduced between the adaptor and the polynucleotide fragment. A nick translation reaction is performed on the circular nucleic acid molecules to produce a plurality of circular nucleic acid molecules each having at least one nick present within its corresponding polynucleotide fragment. The resulting circular nucleic acid molecules are cleaved at a point opposite a nick to release the paired tag clones, thereby producing a paired tag library. The paired tag clones of the paired tag library can be attached to a solid support, such as a micro array.

Example 8

This Example illustrates another method of making of a paired tag library.

In this Example, nucleic acid sequence is sheared to produce a plurality of polynucleotides of interest about 2 kb to about 3 kb in length. The ends of the polynucleotides of interest are blunt-ended. Adaptor 1 is attached to each end of the polynucleotides of interest, thereby forming a plurality of adaptor modified polynucleotides of interest. Both ends of the adaptor modified polynucleotides of interest are ligated to adaptor 2 to produce a plurality of circular nucleic acid molecules, wherein a nick is introduced between adaptor 2 and adaptor 1. A nick translation reaction is performed on the circular nucleic acid molecules to produce a plurality of circular nucleic acid molecules each having at least one nick present within its corresponding polynucleotide fragment. The resulting circular nucleic acid molecules are cleaved at a point opposite a nick to release the paired tag clones, thereby producing a paired tag library. The paired tag clones of the paired tag library can be attached to a solid support, such as a microarray.

Example 9

This Example illustrates another method of sequencing of a paired tag library.

In this Example, a nucleic acid sequence is fragmented to produce a plurality of polynucleotides of interest having a 5' end and a 3' end. The polynucleotide fragments are subjected to a size selection method to select polynucleotides of interest from about 2 kb to about 3 kb. The ends of the polynucleotides of interest are blunt-ended, and then treated with alkaline phosphatase to remove 5' phosphate residues from the ends. Adaptors are joined to the ends of each polynucleotides of interest to produce a plurality of circular nucleic acid molecules, wherein a nick is introduced between the adaptor and the polynucleotides of interest. A nick translation reaction is performed on the circular nucleic acid molecules to produce a plurality of circular nucleic acid molecules each having at least one nick present within its corresponding polynucleotide fragment. The resulting circular nucleic acid molecules are cleaved at a point opposite a nick to release the paired tag clones, thereby producing a paired tag library. The paired tag clones of the paired tag library are attached to a solid support, such as a microarray.

For sequencing the paired tag library, primer adaptors are attached to the ends of the paired tag clones attached to a solid support. The paired tag clones are clonally amplified by, for example, emulsion PCR, and subsequently sequenced by, for example, SOLiD™ sequencing.

Example 10

This Example illustrates another method of making a paired tag clone.

A DNA adaptor I that has an EcoP15I recognition site can be ligated to both ends of a polynucleotide of interest to form an adaptor modified polynucleotide of interest as shown in FIG. 8. The adaptor modified polynucleotide of interest can then be circularized (FIG. 8). A nicking restriction enzyme can be used to make a nick at one strand down stream of the EcoP15I site as shown in FIG. 9. A nick translation reaction can be performed, and the nicks can be translocated in the 5' to 3' direction into the polynucleotide of interest (FIG. 9).

Example 11

This Example illustrates one method of making a nicked circular nucleic acid.

In this Example, an adaptor having Topoisomerase I binding sites is employed to facilitate preparation of a circular nucleic acid. A Topo binding adaptor having a nick on opposite strands is formed by annealing the four oligonucleotides, Topo-IA-A-1, Topo-IA-B-1, Topo-IA-A-2 and Topo-IA-B-2 (FIG. 10). Oligonucleotides Topo-IA-B-1 and Topo-IA-A-2 each have a Topo binding site at the 3' end and lack a 5' phosphate. As shown in FIG. 10, Topo-IA-A-1 is coupled to a binding moiety, biotin. The resulting Topo binding adaptor has Topo binding sites at the 3' end of both strands, nicks on opposite strands, and is coupled to a biotin (FIG. 10).

Topoisomerase I is added to the Topo binding adaptor to generate a Topoisomerase I-adaptor complex, as shown in FIG. 11. Topoisomerase I covalently binds to the adaptor, forming phosphotyrosil bonds between the 3' phosphate of the cleaved strands and the Tyr274 residue of Topoisomerase I, forming the Topoisomerase I-adaptor complex (FIG. 11).

The Topoisomerase I-adaptor complex is combined with a dephosophorylated polynucleotide of interest (FIG. 12). The 5' hydroxyl groups of the dephosphorylated polynucleotide of interest attack the phosphotyrosil bond of the Topoisomerase I-adaptor complex, as shown in FIG. 12. A circular nucleic acid molecule comprising the adaptor and the polynucleotide of interest is formed, as shown in FIG. 13.

Example 12

This Example illustrates another method of making of a paired tag.

In this Example, polynucleotides of interest are circularized by ligating the polynucleotide of interest to one or more adaptors. The resulting nicked circular DNA molecules are nick translated. The nick translation reaction can be performed using *E. coli* DNA polymerase I. The circular nucleic acid molecule will have two nicks within the polynucleotide of interest. Single strand gaps on the circular DNA are formed as depicted in FIG. 15. The gaps are formed by digesting the nicked circular DNA molecule with T7 exonuclease. The resulting gaped circular DNA molecules are digested with S1 nuclease to release the paired DNA tags.

Example 13

This Example illustrates a method of making of a paired tag without nick translation.

In this Example, a polynucleotide of interest is initially circularized by ligating an adaptor to both ends of the polynucleotide of interest. The resulting circular nucleic acid molecule has a first nick between the polynucleotide of interest and the adaptor on one strand of the polynucleotide duplex, and a second nick between the polynucleotide of interest and the adaptor on a different strand of the polynucleotide duplex. A single stranded region of the polynucleotide of interest is formed by digesting the nicked circular DNA molecule with a 5' to 3' exonuclease. The resulting molecule then has its 3' ends extended with a DNA polymerase. The resulting molecule is then digested with S1 nuclease to release the paired DNA tags.

Example 14

This Example illustrates a method of making of a paired tag without nick translation. In this Example, nicked circular DNA molecules that include a double stranded polynucleotide of interest ligated to at least one adaptor are digested by a 5' to 3' exonuclease. This reaction is allowed to continue to completion so that the entireties of what had been the double stranded polynucleotides of interest are now single stranded. The resulting construct then has its 3' ends extended with a DNA polymerase as depicted in FIG. 20. The resulting construct is then digested with single strand specific exonuclease to release the paired tags.

Example 15

This Example illustrates the preparation of a vector used to construct a paired tag library. In this Example, a small circular DNA in the 2 kb to 3 kb range is selected as a vector for a population of polynucleotides of interest. The vector is modified with biotin for subsequent receptor-ligand based affinity purification. The vector is linearized with a method that generates incompatible sticky ends on the linearized vector so as to prevent vector self-ligation. Subsequently, two double stranded adaptors are ligated to the linearized vector as depicted in FIG. 23. The top strands of both adaptors contain no phosphate groups at their 5'-ends; in contrast, the bottom strands of both adaptors contain a phosphate group at their 5'-ends. As a result of such configuration, only the bottom strands of both adaptors are ligated to the linear vector and there is a nick between the linear vector and the adaptor.

Example 16

This Example illustrates a paired tag library preparation workflow. In this Example, polynucleotides of interest are first modified to have the appropriate end configurations to match the ends of a modified set of nicked linking polynucleotides. Then the polynucleotides of interest are incubated with the nicked linking polynucleotide and a ligation reaction is performed. After ligation, the circularized nicked linking polynucleotides contain two nicks located close to the polynucleotides of interest. The nicks are then extended into the polynucleotide of interest by nick translation. After the ligation reaction, un-ligated constructs are eliminated by digesting the linear polynucleotides. After purification and translation of the nicks, the circular population is then cut at the nick position, thereby releasing the paired tag.

Example 17

This example illustrates one set of further manipulations that can be performed on the released paired tag. The released paired tag of Example 16 is recircularized by ligating an internal adaptor between the two ends of the paired tag. Following this, a PCR amplification can be performed using primers that hybridize to the sequences in the two adaptor ends. The PCR amplified product can be a final paired tag library.

While the present teachings have been described in terms of these exemplary embodiments, the skilled artisan will readily understand that numerous variations and modifications of these exemplary embodiments are possible without undue experimentation. All such variations and modifications are within the scope of the current teachings.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein.

In this application, the use of the singular can include the plural unless specifically stated otherwise or unless, as will be understood by one of skill in the art in light of the present disclosure, the singular is the only functional embodiment. Thus, for example, "a" can mean more than one, and "one embodiment" can mean that the description applies to multiple embodiments. Additionally, in this application, "and/or" denotes that both the inclusive meaning of "and" and, alternatively, the exclusive meaning of "or" applies to the list. Thus, the listing should be read to include all possible combinations of the items of the list and to also include each item, exclusively, from the other items. The addition of this term is not meant to denote any particular meaning to the use of the terms "and" or "or" alone. The meaning of such terms will be evident to one of skill in the art upon reading the particular disclosure.

INCORPORATION BY REFERENCE

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

EQUIVALENTS

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A method of forming a paired tag comprising a first tag sequence and a second tag sequence that together comprise at least part of a polynucleotide of interest, said method comprising: (a) ligating a first end and a second end of a double stranded polynucleotide of interest to one or more double stranded nucleic acid adaptors to form a circular double stranded nucleic acid molecule having a first nick and a second nick on different strands of the circular nucleic acid molecule wherein a first strand of the first end of the double stranded polynucleotide of interest is joined to one strand of the one or more double stranded nucleic acid adaptors so as to form a first nick, and wherein a second strand of the second end of the double stranded polynucleotide of interest is joined to one strand of the one or more double stranded nucleic acid adaptors so as to form a second nick; and (b) performing a nick translation reaction to move the first and the second nick to new positions within the double stranded polynucleotide of interest.

2. The method of claim 1, further comprising: allowing the nick translation reaction to proceed for a specific time; and terminating the nick translation reaction.

3. The method of claim 1, wherein the first end and the second end of the double stranded polynucleotide of interest lack 5' phosphate residues.

4. The method of claim 1, further comprising terminating the nick translation reaction before the first nick and the second nick are translated past each other.

5. The method of claim 1, wherein the first nick and the second nick are translated more than 10 bases.

6. The method of claim 4, wherein the first nick and the second nick are translated less than 500 bases.

7. The method of claim 1, wherein at least one strand of the one or more double stranded adaptors lacks a 5' phosphate residue.

8. The method of claim 6, wherein the first nick and the second nick are translated less than 100 bases.

9. The method of claim 4, wherein the first nick and the second nick are translated between about 20 bases to about 50 bases.

10. The method of claim 1, wherein the first nick or the second nick is translated less than 500 bases.

11. The method of claim 9, wherein the first nick or the second nick is translated more than 27 bases and less than 500 bases.

12. The method of claim 10, wherein the first nick or the second nick is translated less than 200 bases.

13. The method of claim 1, wherein the first nick or the second nick is translated from 28 bases to about 50 bases.

14. The method of claim 1, wherein the circular nucleic acid molecule comprises a first adaptor ligated to a second adaptor and the first and second adaptors are ligated to the first end and the second end of the double stranded polynucleotide of interest.

15. The method of claim 14, wherein the circular nucleic acid molecule comprises a first nick between the first end of the double stranded polynucleotide of interest and the first adaptor and a second nick between the second end of the double stranded polynucleotide of interest and the second adaptor.

16. The method of claim 13, wherein the circular nucleic acid sequence comprises a gap that is filled in with nucleotides when the nick translation reaction is performed, thereby resulting in a nick.

17. The method of claim 1, wherein the polynucleotide of interest comprises from 50 to 2500 nucleotides.

18. The method of claim 16, wherein the polynucleotide of interest is subjected to a size selection technique to select for polynucleotides comprising from 50 to 2500 nucleotides prior to the ligating step.

19. The method of claim 1, wherein the one or more double stranded nucleic acid adaptors comprise a binding moiety.

20. The method of claim 1, wherein the nick translation reaction is performed using an enzyme selected from the group consisting of *E. Coli* DNA polymerase I, Taq DNA polymerase, Vent DNA polymerase, Klenow DNA polymerase I, and phi29 DNA polymerase and any combination thereof.

21. The method of claim 1, wherein the nick translation reaction is performed using a DNA polymerase having 5' to 3' exonuclease activity.

22. The method of claim 1, wherein the nick translation reaction comprises removal of nucleotides by 5' to 3' exonuclease activity.

23. The method of claim 1, wherein the nick translation reaction occurs by strand displacement.

24. The method of claim 1, further comprising cleaving the circular nucleic acid molecule at a first translated nick, thereby forming a linear polynucleotide comprising a first tag sequence and a second tag sequence separated by the one or more double stranded nucleic acid adaptors, wherein the first tag sequence and the second tag sequence are derived from the polynucleotide of interest.

25. The method of claim 23, further comprising cleaving the circular nucleic acid molecule at a second translated nick.

26. The method of claim 23, wherein the circular nucleic acid molecule is cleaved by an enzyme selected from the group consisting of S1 nuclease, mung bean nuclease, nuclease P1, nuclease BAL-31, and any combination thereof.

27. The method of claim 23, further comprising amplifying the linear polynucleotide.

28. The method of claim 1, wherein the one or more double stranded nucleic acid adaptors comprise a binding moiety that comprises biotin.

29. The method of claim 28, further comprising the step of using streptavidin to purify the paired tag.

30. The method of claim 1, further comprising treating the polynucleotide of interest with an alkaline phosphatase prior to ligation, wherein a 5'-phosphate is removed from both the first end and the second end of the polynucleotide of interest.

31. The method of claim 29, wherein the alkaline phosphatase is selected from the group consisting of calf intestinal alkaline phosphatase, bacterial alkaline phosphatase, shrimp alkaline phosphatase, and some combination thereof.

32. The method of claim 1, wherein the circular double stranded nucleic acid molecule comprises a first and a second adaptor, wherein the second adaptor is positioned adjacent to each other.

33. The method of claim 31, wherein one strand of the first adaptor and one strand of the second adaptor lack a 5' phosphate.

34. The method of claim 1, wherein each step is performed in the order listed in claim 1.

35. A method of forming a released paired tag from a DNA fragment of interest, comprising: ligating a first adaptor to a first end of a DNA fragment of interest and ligating a second adaptor to a second end of the DNA fragment of interest, thereby producing an adaptor modified fragment, circularizing the adaptor modified fragment by attaching a third adaptor to the adaptor modified fragment, thereby forming a circular nucleic acid molecule wherein a first nick is present between the third adaptor and the first adaptor and a second nick is present between the second adaptor and the third adaptor, wherein the circular nucleic acid molecule comprises a first strand and a second strand of DNA, and wherein the first nick and the second nick are not present on the same strand of the circular nucleic acid molecule; performing a nick translation reaction wherein a nick on each strand of the circular nucleic acid molecule is translated into the DNA fragment of interest, and cleaving the circular nucleic acid molecule at a position at a translated nick, thereby forming a released paired tag.

36. The method of claim 35, further comprising: allowing the nick translation reaction to proceed for a specific time; and terminating the nick translation reaction.

37. The method of claim 36, further comprising terminating the nick translation reaction prior to cleaving the polynucleotide strand at each position at a translated nick.

38. The method of claim 35, further comprising attaching primer adaptors to the ends of the paired tag.

39. The method of claim 38, further comprising amplifying the paired tag with primers for the primer adaptors.

40. The method of claim 39, wherein the amplification is a clonal amplification.

41. The method of claim 40, wherein the clonal amplification comprises emulsion polymerase chain reaction (emulsion PCR).

42. The method of claim 40, wherein the clonal amplification comprises bridge polymerase chain reaction (bridge PCR).

43. The method of claim 35, wherein the third adaptor comprises a binding moiety, and further comprising binding the binding moiety to a solid support.

44. The method of claim 42, wherein the solid support is an array.

45. The method of claim 35, further comprising sequencing a portion of the paired tag.

46. A method of forming a paired tag comprising a first tag sequence and a second tag sequence that together comprise at least part of a polynucleotide of interest, said method comprising: ligating a first end of a double stranded polynucleotide of interest to at least one adaptor; ligating a second end of the double stranded polynucleotide of interest to at least one adaptor; forming a circular nucleic acid molecule comprising the double stranded polynucleotide of interest, a first nick comprising a first 3' end on a first strand of the circular nucleic acid molecule and a second nick comprising a second 3' end on a second strand of the circular nucleic acid molecule, wherein the first nick and the second nick are on different strands of the circular nucleic acid molecule; extending the first 3' end of the first strand of the circular nucleic acid molecule into a sequence of the double stranded polynucleotide of interest; and extending the second 3' end of the second strand of the circular nucleic acid molecule into a sequence of the double stranded polynucleotide of interest.

47. The method of claim 46, wherein prior to extending the first 3' end, the first nick is located between the first end of the double stranded polynucleotide of interest and the at least one adaptor and the second nick is located between the second end of the double stranded polynucleotide of interest and the at least one adaptor.

48. The method of claim 47, wherein the first and second ends of the double stranded polynucleotide of interest are connected to a same adaptor.

49. The method of claim 46, wherein the adaptor comprises a first and a second adaptor, wherein the first adaptor is located on the first end of the double stranded polynucleotide of interest and wherein the second adaptor is located on the second end of the double stranded polynucleotide of interest upon formation of the circular nucleic acid molecule.

50. The method of claim 49, wherein the first adaptor is connected to the second adaptor through a linking polynucleotide.

51. The method of claim 50, wherein upon formation of the circular nucleic acid molecule, the first nick is located at an end of the first adaptor that is distal to an end of the first adaptor that is connected to the double stranded polynucleotide of interest and the second nick is located at an end of the second adaptor that is distal to an end of the second adaptor that is connected to the double stranded polynucleotide of interest.

52. The method of claim 51, wherein the adaptors are ligated to a linking polynucleotide before the adaptors are ligated to the double stranded polynucleotide of interest.

53. The method of claim 46, further comprising digesting at least a part of the first strand of the circular nucleic acid molecule and digesting at least a part of the second strand of the circular nucleic acid molecule, wherein the digesting results in at least a portion of the double stranded polynucleotide of interest becoming single stranded, wherein the digesting occurs before the extending of the first and second 3' ends.

54. The method of claim 53, wherein a 5' to 3' exonuclease is used to digest said nicked circular nucleic acid molecule.

55. The method of claim 53, wherein the digestion is halted before the double stranded polynucleotide of interest becomes single stranded in its entirety.

56. The method of claim 53, wherein the entire double stranded polynucleotide of interest is digested to a single stranded polynucleotide of interest.

57. The method of claim 53, wherein a DNA polymerase is used to extend said nicked circular nucleic acid molecule.

58. The method of claim 46, further comprising digesting at least a part of the first strand of the circular nucleic acid molecule and digesting at least a part of the second strand of the circular nucleic acid molecule, wherein the digesting results in at least a portion of the double stranded polynucleotide of interest becoming single stranded, wherein the digesting occurs at the same time as the extending of the first and second 3' ends.

59. The method of claim 58, wherein the digesting and the extending take place in the same reaction tube.

60. The method of claim 46, wherein the extending of the first 3' end of the first strand of the circular nucleic acid molecule into a sequence of the double stranded polynucleotide of interest is achieved by nick translation.

61. The method of claim 60, wherein the extending of the second 3' end of the second strand of the circular nucleic acid molecule into a sequence of the double stranded polynucleotide of interest is achieved by nick translation.

62. The method of claim 61, wherein the first and second nicks are expanded into a first gap and second gap respectively.

63. The method of claim 62, wherein an exonuclease is used to expand the first and second nicks into the first gap and second gap respectively.

64. The method of claim 63, wherein the exonuclease comprises a T7 exonuclease.

65. The method of claim 46, further comprising performing a single strand dependent digest to release the paired DNA tag.

66. A method of preparing a paired tag, said method comprising: providing a nicked linking polynucleotide comprising: a first adaptor comprising a first adaptor strand that is hybridized to a second adaptor strand, wherein the first adaptor strand lacks a phosphate group on its 5' end; a second adaptor comprising a third adaptor strand that is hybridized to a fourth adaptor strand, wherein the third adaptor strand lacks a phosphate group on its 5' end; and a linking polynucleotide comprising a first linking strand hybridized to a second linking strand, wherein the linking polynucleotide comprises a first end and a second end, wherein the first adaptor is attached to the first end of the linking polynucleotide such that a nick is present where the first adaptor strand lacks a phosphate group on its 5' end, wherein the second linking strand is attached to the second adaptor strand, wherein the second adaptor is attached to the second end of the linking polynucleotide such that a nick is present where the third adaptor strand of the second adaptor lacks a phosphate group on its 5' end, wherein the second strand of the linking polynucleotide is attached to the fourth adaptor strand; ligating a first end of a double stranded polynucleotide of interest to the first adaptor and ligating a second end of the double stranded polynucleotide of interest to the second adaptor; and moving the first and second nicks into the double stranded polynucleotide of interest.

67. The method of claim 66, further comprising a single strand dependent digest to linearize the nicked linking polynucleotide.

68. The method of claim 66, further comprising ligating an internal adaptor into the linearized nicked linking polynucleotide.

69. The method of claim 68, further comprising amplifying at least one strand of the double stranded polynucleotide of interest.

70. The method of claim 69, wherein the amplification is a PCR based amplification.

71. The method of claim 1, wherein the circular nucleic acid molecule comprises a first adaptor ligated to the first end and the second end of a double stranded polynucleotide of interest.

72. The method of claim 71, wherein the circular nucleic acid molecule comprises a first nick between the first end of the double stranded polynucleotide of interest and the first adaptor and a second nick between the second end of the double stranded polynucleotide of interest and the first adaptor.

* * * * *